(12) United States Patent
Wold et al.

(10) Patent No.: US 6,627,190 B2
(45) Date of Patent: Sep. 30, 2003

(54) RECOMBINANT ADENOVIRUS VECTORS THAT ARE REPLICATION-COMPETENT IN TERT-EXPRESSING CELLS

(75) Inventors: William S. M. Wold, Chesterfield, MO (US); Karoly Toth, St. Louis, MO (US); Konstantin Doronin, Moscow (RU); Ann E. Tollefson, St. Louis, MO (US); Mohan Kuppuswamy, Ballwin, MO (US)

(73) Assignee: Saint Louis University, Saint Louis, MO (US)

( * ) Notice: Subject to any disclaimer, the term of this patent is extended or adjusted under 35 U.S.C. 154(b) by 0 days.

(21) Appl. No.: 09/956,335

(22) Filed: Sep. 19, 2001

(65) Prior Publication Data

US 2002/0028785 A1 Mar. 7, 2002

Related U.S. Application Data

(63) Continuation-in-part of application No. 09/351,778, filed on Jul. 12, 1999.
(60) Provisional application No. 60/233,872, filed on Sep. 20, 2000.

(51) Int. Cl.[7] .......................... A01N 63/00; A61K 48/00

(52) U.S. Cl. ................... 424/93.2; 435/320.1; 435/455; 435/456

(58) Field of Search ............................. 435/320.1, 455, 435/456; 514/44; 424/93.2

(56) References Cited

U.S. PATENT DOCUMENTS

| | | | |
|---|---|---|---|
| 5,677,178 A | 10/1997 | McCormick | ................. 435/325 |
| 5,846,945 A | 12/1998 | McCormick | ................. 514/44 |
| 5,851,806 A | * 12/1998 | Kovesdi et al. | .......... 435/91.41 |
| 6,197,293 B1 | 3/2001 | Henderson et al. | ......... 424/93.2 |
| 6,254,862 B1 | 7/2001 | Little et al. | ................. 424/93.2 |

FOREIGN PATENT DOCUMENTS

| | | |
|---|---|---|
| WO | WO98/39465 | 9/1998 |
| WO | WO 02/24640 A2 * | 3/2003 |

OTHER PUBLICATIONS

RG Vile et al., Gene Therapy, (2000), 7, pp. 2–8.*
Stem Cells, Jun. 2001, http://www.nih.gov/news/stemcell/scireport.htm, ES–1–ES–10.*
Masahiro Takakura et al., Cancer Research, 59, pp. 551–557, Feb. 1, 1999, pp. 551–557.*
Shoji Koga et al., Human Gene Therapy, 11: pp. 1397–1406, Jul. 1, 2000.*
Taro Kanaya et al., Clinical Cancer Research, vol. 6, pp. 1239–1247, Apr. 2000.*
Gabor M. Rubanyi, Molecular Aspects of Medicine, 22 (2001), pp. 113–142.*
Bett, et al., DNA Sequence of the Deletion/Insertion in Early Region 3 of AD5 dl309. Virus Research, 1995, vol. 39, pp. 75–82.
Anderson, Nature, vol. 392, Human gene therapy, pp. 25–30, 1998.
Anderson et al., Adenovirus–mediated tissue–targeted expression of the HSVtk gene for the treatment of breast cancer, Gene Therapy 6:854–864 (1999).
Arai et al., Gene transfer of Fas ligand induces tumor regression in vivo, Proc. Natl. Acad. Sci. USA 94:13862–13867 (1997).
Bischoff et al., An Adenovirus Mutant that Replicates Selectivety in p53–Deficient Human Tumor Cells, Science 274:373–376 (1996).
Chakravarti et al., A Viral Mechanism for Inhibition of p300 and PCAF Acetyltransferase Activity, Cell 96:393–403 (1999).
Curiel, Strategies to Adapt Adenoviral Vectors for Targeted Delivery, Curiel: Gene Therapy Strategies, pp. 158–171, date unknown.
Doronin et al., Journal of Virology vol. 74, No. 13, XP–002162706, Tumor–Specific, Replication–Competent Adenovirus Vectors Overexpressing the Adenovirus Death Protein, pp. 6147–6155, Jul., 2000.
De–Chao et al., The addition of Adenovirus Type 5 Region E3 Enables Calydon Virus 787 to Eliminate Distant Prostate Tumor Xenografts, Cancer Research 59:4200–4203 (1999).
Elshami et al., Human Gene Therapy, vol. 7, Treatment of Pleural Mesothelioma in an Immunocompetent Rat Model Utilizing Adenoviral Transfer of the Herpes Simplex Virus Thymidine Kinase Gene, pp. 141–148, 1996.
Felzmann et al., Characterization of the antitumor immune response generated by treatment of murine tumors with recombinant adenovirus expressing HSVtk, IL–2, IL–6 or B7–1, Gene Ther. 4:1322–1329 (1997).
Freytag et al., Human Gene Therapy, vol. 9, A Novel Three–Pronged Approach to Kill Cancer Cells Selectively: Concomitant Viral, Double Suicide Gene, and Radiotherapy, p. 1323–1333, 1998.
Gomez–Navarro et al., European Journal of Cancer, vol. 35, No. 6, Gene Therapy for Cancer, pp. 867–885, 1999.
Greenberg et al., Liver–specific expression of the human factor VII gene, Proc. Natl. Acad. Sci. USA 92:12347–12351 (1995).

(List continued on next page.)

Primary Examiner—Scott D. Priebe
Assistant Examiner—Brian Whiteman
(74) Attorney, Agent, or Firm—Thompson Coburn, LLP

(57) ABSTRACT

Novel adenovirus vectors which overexpress an adenovirus death protein and which are replication-competent in and, preferably, replication-restricted to cells expressing telomerase. One embodiment provides for efficient destruction and removal of viral-infected host cells expressing telomerase. Still further, another embodiment provides for additional restriction and safety by disrupting E1A's ability to bind p300 and/or members of the Rb family members. Compositions of the novel vectors and methods for promoting death of cells expressing telomerase with these vectors are also disclosed.

11 Claims, 18 Drawing Sheets-

OTHER PUBLICATIONS

Hallenbeck et al., A Novel Tumor–Specific Replication–Restricted Adenoviral Vector for Gene Therapy of Hepatocellular Carcinoma, *Human Gene Therapy* 10:1721–1733 (1999).

Hamamori et al., Regulation of Histone Acetyltransferases p300 and PCAF by thge bHLH Protein Twist and Adenoviral Oncoprotein E1A, *Cell* 96:405–413 (1999).

Harada et al., p53–Independent and –Dependent Requirements for E1B–55K in Adenovirus Type 5 Replication, *J. Virol* 73:5333–5344 (1999).

Harrod et al., Lung–Specific Expression of Adenovirus E3–14.7K in Transgenic Mice Attenuates Adenoviral Vector–Mediated Lung Inflammation and Enhances Transgene Expression, *Human Gene Therapy* 9:1885–1898 (1998).

Hausmann et al., Virology, vol. 244, XP–0021162709, Adenovirus Death Protein, a Transmembrane Protein Encoded in the E3 Region, Is Palmitoylated at the Cytoplasmic Tail, pp. 343–351, 1998.

Heise et al., Onyx–015, an E1B gene–attenuated adenovirus, causes tumor–specific cytolysis and antitumoral efficacy that can be augmented by standard chemotherapeutic agents, *Nature Med.* 3:639–645 (1997).

Hobbs et al., Proc. Natl. Acad. Sci., vol. 95, Regulation of transport pathways in tumor vessels: Role of tumor type and microenvironment, pp. 4610–4612, 1998.

Howe et al., Retinoblastoma growth suppressor and a 300–kDa protein appear to regulate cellular DNA synthesis, *Proc. Natl. Acad. Sci.* 87:5883–5887 (1990).

Jain, Journal of Controlled Release, vol. 53, Delivery of molecular and cellular medicin to solid tumors, pp. 49–67, 1998.

Jones et al., Isolation of Adenovirus Type 5 Host Range Deletion Mutants Defective for transformation of Rat Embryo Cells, *Cell* 17:683–689 (1979).

Lazzaro et al., The transcription factor TTF–1 is expressed at the onset of thyroid and lunc morphogenesis and in restricted regions of the foetal brain, *Development* 113:1093–1104 (1991).

Li et al., Cancer Research, vol. 59, Loss of Adenoviral Receptor Expression in Human Bladder Cancer Cells: A Potential Impact on the Efficacy of Gene Therapy, pp. 325–330, 1999.

Li et al., Clinical Cancer Research, vol. 5, Variability of Adenovirus Receptor Density Influences Gene Transfer Efficiency and Therapeutic Response in Head and Neck Cancer, pp. 4175–4181, 1999.

Li et al., Control of apoptosis and mitotic spindle checkpoint by survivin, *Nature* 396:580–584 (1998).

Lubeck et al., Immunogenicity of Recombinant Adenovirus–Human Immunodeficiency Virus Vaccines in Chimpanzees Following Intranasal Administration, *AIDS Res. Hum. Retroviruses* 10:1443–1449 (1994).

Massie et al., Inducible Overexpression of a Toxic Protein by an Adenovirus Vector with a Tetracycline–Rugulatable Expression Cassett, *J. of Virol.* 72:2289–2296 (1998).

Miller et al., Progress in Transcriptionally Targeted and Regulatable Vectors for Genetic Therapy, *Human Gene Therapy* 8:803–815 (1997).

Niiler, Nature Biotechnology, vol. 18, Researchers consider first transgenic fish, pp. 143–144, 2000.

Putzer et al., Interleukin 12 and B7–1 costimulatory molecule expressed by an adenovirus vector act synergistically to facilitate tumor regression, *Proc. Natl. Acad. Sci. USA* 94:10889–10894 (1997).

Rodriguez et al., Prostate Attenuated Replication Competent Adenovirus (ARCA) CN706: A Selective Cytotoxic for Prostate–specific Antigen–positive Prostate Cancer Cells, *Cancer Res.* 57:2559–2563 (1997).

Rudinger, Peptide Hormones, Characteristics of the amino acids as components of a peptide hormone sequence, pp. 1–7, 1976.

Scaria et al., The E3–11.6K Protein of Adenovirus is an Asn–Glycosylated Integral Membrane Protein That Localizes to the Nuclear Membrane, *Virology* 191:743–753 (1992).

Sparer et al., The Role of Human Adenovirus Early Region 3 Proteins (gp19K, 10.4K, 14.5K, and 14.7K) in a Murine Pneumonia Model, *J. Virol.* 70:2431–2439 (1996).

Tollefson et al., Journal of Virology, The Adenovirus Death Protein (E3–11.6K) Is Required at Very Late Statges of Infection for Efficient Cell Lysis and Release of Adenovirus form Infected Cells, pp. 2296–2306, 1996.

Tollefson et al., Forced degradation of Fas inhibits apoptosis in adenovirus–infected cells, *Nature* 392:726–730 (1998).

Tollefson et al., The E3–11.6–kDa Adenovirus Death Protein (AdP) Is Required for Efficient Cell Death: Characterization of Cells Infected with adp Mutants, *Virol.* 220:152–162 (1996).

Tollefson et al., The Adenovirus Death Protein (E3–11.6K) Is Required at Very Late Stages of Infection for Efficient Cell Lysis and Release of Adenovirus from Infected Cells, *J. Virol.* 70l:2296–2306 (1996).

Topf et al., Regional 'pro–drug' gene therapy: intravenous administration of an adenoviral vector expressing the *E. coli* cytosine deaminase gene and systemic administration of 5–fluorocytosine suppresses growth of hepatic metastasis of colon carcinoma, *Gene Ther.* 5:507–513 (1998).

Verma et al., Nature, vol. 389, Gene therapy–promises, problems and prospects, pp. 289–242, 1997.

Wildner et al., Therapy of Colon Cancer with Oncolytic Adenovirus Is Enhanced by the Addition of Herpes Simplex Virus–*thymidine kinase*, *Cancer Res.* 59:410–413 (1999).

Wildner et al., Adenoviral vectors capable of replication improve the efficacy of HSVtk/GCV suicide gene therapy of cancer, *Gene Therapy* 6:57–62 (1999).

Wold et al., Adenovirus E3 Proteins: 14.7K, RID, and gp19K Inhibit Immune–Induced Cell Death; Adenovirus Death Protein Promotes Cell Death, *Semin. Virol.* 8:515–523 (1998).

Wold et al., Evidence that Aguauaugaa and CCaagauga Initiate Translation in the Same mRNA in Region E3 of Adenovirus, *Virology* 148:168–180 (1986).

Yan et al., Upstream Enhancer Activity in the Human Surfactant Protein B Gene Is Mediated by Thyroid Transcription Factor 1, *J. Biol. Chem.* 270:24852–24857 (1995).

Ramachandra et al., Nature Biotechnology, vol. 19, Re–engineering adenovirus regulatory pathways to enhance oncolytic specificity and efficacy, pp. 1035–1041, Nov. 2001(accompanied by a commentary by R. Viles, Vironcology–not yet, but soon? pp. 1020–1022).

* cited by examiner

SW480

Mock

GZ3

GZ3-TERT

LNCaP

Mock

GZ3

GZ3-TERT

HeLa: GZ3

E1A

HeLa: GZ3-TERT

E1A

ORF3

ORF3

HeLa: GZ3

DBP

HeLa: GZ3-TERT

DBP

Fiber

Fiber

A549: GZ3

E1A

A549: GZ3-TERT

E1A

ORF3

ORF3

A549: GZ3

DBP

A549: GZ3-TERT

DBP

Fiber

Fiber

Hep3B: GZ3

E1A

Hep3B: GZ3-TERT

E1A

ORF3

ORF3

Hep3B: GZ3

DBP

Hep3B: GZ3-TERT

DBP

Fiber

Fiber

A549

SW480

LS513

SEQUENCE LISTING

```
<160> NUMBER OF SEQ ID NOS: 3

<210> SEQ ID NO 1
<211> LENGTH: 35978
<212> TYPE: DNA
<213> ORGANISM: Adenovirus

<400> SEQUENCE: 1
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgtttttg     180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tatttgtcta gggccgcggg     360
```

-continued

```
gactttgacc gtttacgtgg agactcgccc aggtgttttt ctcaggtgtt ttccgcgttc    420
cgggtcaaag ttggcgtttt attattatag tcagctgacg tgtagtgtat ttatacccgg    480
tgagttcctc aagaggccac tcttgagtgc cagcgagtag agttttctcc tccgagccgc    540
tccgacaccg ggactgaaaa tgagacatat tatctgccac ggaggtgtta ttaccgaaga    600
aatggccgcc agtcttttgg accagctgat cgaagaggta ctggctgata atcttccacc    660
tcctagccat tttgaaccac ctacccttca cgaactgtat gatttagacg tgacggcccc    720
cgaagatccc aacgaggagg cggtttcgca gatttttccc gactctgtaa tgttggcggt    780
gcaggaaggg attgacttac tcactttttcc gccggcgccc ggttctccgg agccgcctca    840
cctttcccgg cagcccgagc agccggagca gagagccttg ggtccggttt ctatgccaaa    900
ccttgtaccg gaggtgatcg atcttacctg ccacgaggct ggctttccac ccagtgacga    960
cgaggatgaa gagggtgagg agtttgtgtt agattatgtg gagcacccccg ggcacggttg   1020 caggtcttgt cattatcacc ggaggaatac gggggaccca gatattatgt gttcgctttg   1080
ctatatgagg acctgtggca tgtttgtcta cagtaagtga aaattatggg cagtgggtga   1140
tagagtggtg ggtttggtgt ggtaatttt ttttttaattt ttacagtttt gtggtttaaa   1200
gaattttgta ttgtgatttt tttaaaaggt cctgtgtctg aacctgagcc tgagcccgag   1260
ccagaaccgg agcctgcaag acctacccgc cgtcctaaaa tggcgcctgc tatcctgaga   1320
cgcccgacat cacctgtgtc tagagaatgc aatagtagta cggatagctg tgactccggt   1380
ccttctaaca cacctcctga gatacacccg gtggtcccgc tgtgccccat taaaccagtt   1440
gccgtgagag ttggtgggcg tcgccaggct gtggaatgta tcgaggactt gcttaacgag   1500
cctgggcaac ctttggactt gagctgtaaa cgccccaggc cataaggtgt aaacctgtga   1560
ttgcgtgtgt ggttaacgcc tttgtttgct gaatgagttg atgtaagttt aataaagggt   1620
gagataatgt ttaacttgca tggcgtgtta aatgggggcgg ggcttaaagg gtatataatg   1680
cgccgtgggc taatcttggt tacatctgac ctcatggagg cttgggagtg tttggaagat   1740
ttttctgctg tgcgtaactt gctggaacag agctctaaca gtacctcttg gttttggagg   1800
tttctgtggg gctcatccca ggcaaagtta gtctgcagaa ttaaggagga ttacaagtgg   1860
gaatttgaag agcttttgaa atcctgtggt gagctgtttg attctttgaa tctgggtcac   1920
caggcgcttt tccaagagaa ggtcatcaag actttggatt tttccacacc ggggcgcgct   1980
gcggctgctg ttgctttttt gagttttata aaggataaat ggagcgaaga aacccatctg   2040 agcgggggt acctgctgga ttttctggcc atgcatctgt ggagagcggt tgtgagacac   2100
aagaatcgcc tgctactgtt gtcttccgtc cgcccggcga taataccgac ggaggagcag   2160
cagcagcagc aggaggaagc caggcggcgg cggcaggagc agagcccatg gaacccgaga   2220
gccggcctgg accctcggga atgaatgttg tacaggtggc tgaactgtat ccagaactga   2280
gacgcatttt gacaattaca gaggatgggc agggctaaa gggggtaaag agggagcggg    2340
gggcttgtga ggctacagag gaggctagga atctagcttt tagcttaatg accagacacc   2400
gtcctgagtg tattactttt caacagatca aggataattg cgctaatgag cttgatctgc   2460
tggcgcagaa gtattccata gagcagctga ccacttactg gctgcagcca ggggatgatt   2520 tgaggaggc tattagggta tatgcaaagg tggcacttag gccagattgc aagtacaaga   2580
tcagcaaact tgtaaatatc aggaattgtt gctacatttc tgggaacggg gccgaggtgg   2640
agatagatac ggaggatagg gtggcccttta gatgtagcat gataaatatg tggccggggg   2700
tgcttggcat ggacgggtg gttattatga atgtaaggtt tactggcccc aatttttagcg   2760
```

```
gtacggtttt cctggccaat accaacctta tcctacacgg tgtaagcttc tatgggttta    2820
acaatacctg tgtggaagcc tggaccgatg taagggttcg gggctgtgcc ttttactgct    2880
gctggaaggg ggtggtgtgt cgccccaaaa gcagggcttc aattaagaaa tgcctctttg    2940
aaaggtgtac cttgggtatc ctgtctgagg gtaactccag ggtgcgccac aatgtggcct    3000
ccgactgtgg ttgcttcatg ctagtgaaaa gcgtggctgt gattaagcat aacatggtat    3060
gtggcaactg cgaggacagg gcctctcaga tgctgacctg ctcggacggc aactgtcacc    3120
tgctgaagac cattcacgta gccagccact ctcgcaaggc ctggccagtg tttgagcata    3180
acatactgac ccgctgttcc ttgcatttgg gtaacaggag ggggtgttc ctaccttacc    3240 aatgcaattt gagtcacact aagatattgc ttgagcccga gcatgtcc aaggtgaacc    3300 tgaacggggt gtttgacatg accatgaaga tctggaaggt gctgaggtac gatgagaccc    3360
gcaccaggtg cagaccctgc gagtgtggcg gtaaacatat taggaaccag cctgtgatgc    3420
tggatgtgac cgaggagctg aggcccgatc acttggtgct ggcctgcacc cgcgctgagt    3480
ttggctctag cgatgaagat acagattgag gtactgaaat gtgtgggcgt ggcttaaggg    3540
tgggaaagaa tatataaggt gggggtctta tgtagttttg tatctgtttt gcagcagccg    3600
ccgccgccat gagcaccaac tcgtttgatg gaagcattgt gagctcatat ttgacaacgc    3660
gcatgccccc atgggccggg gtgcgtcaga atgtgatggg ctccagcatt gatggtcgcc    3720
ccgtcctgcc cgcaaactct actaccttga cctacgagac cgtgtctgga acgccgttgg    3780
agactgcagc ctccgccgcc gcttcagccg ctgcagccac cgcccgcggg attgtgactg    3840
actttgcttt cctgagcccg cttgcaagca gtgcagcttc ccgttcatcc gcccgcgatg    3900
acaagttgac ggctcttttg gcacaattgg attctttgac ccgggaactt aatgtcgttt    3960
ctcagcagct gttggatctg cgccagcagg tttctgccct gaaggcttcc tcccctccca    4020
atgcggttta aaacataaat aaaaaccag actctgtttg gatttggatc aagcaagtgt    4080
cttgctgtct ttatttaggg gttttgcgcg cgcggtaggc ccgggaccag cggtctcggt    4140
cgttgagggt cctgtgtatt ttttccagga cgtggtaaag gtgactctgg atgttcagat    4200
acatgggcat aagcccgtct ctggggtgga ggtagcacca ctgcagagct tcatgctgcg    4260
gggtggtgtt gtagatgatc cagtcgtagc aggagcgctg ggcgtggtgc ctaaaaatgt    4320 cttttcagtag caagctgatt gccaggggca ggcccttggt gtaagtgttt acaaagcggt    4380
taagctggga tgggtgcata cgtggggata tgagatgcat cttggactgt attttaggt    4440 tggctatgtt cccagccata tccctccggg gattcatgtt gtgcagaacc accagcacag    4500
tgtatccggt gcacttggga aatttgtcat gtagcttaga aggaaatgcg tggaagaact    4560
tggagacgcc cttgtgacct ccaagatttt ccatgcattc gtccataatg atggcaatgg    4620
gcccacgggg ggcggcctgg gcgaagatat ttctgggatc actaacgtca tagttgtgtt    4680
ccaggatgag atcgtcatag gccatttta caaagcgcgg gcggagggtg ccagactgcg    4740
gtataatggt tccatccggc ccaggggcgt agttaccctc acagatttgc atttcccacg    4800
ctttgagttc agatgggggg atcatgtcta cctgcgggc gatgaagaaa acggtttccg    4860
gggtagggga gatcagctgg gaagaaagca ggttcctgag cagctgcgac ttaccgcagc    4920
cggtgggccc gtaaatcaca cctattaccg ggtgcaactg gtagttaaga gagctgcagc    4980
tgccgtcatc cctgagcagg ggggccactt cgttaagcat gtccctgact cgcatgtttt    5040
ccctgaccaa atccgccaga aggcgctcgc cgcccagcga tagcagttct tgcaaggaag    5100
```

-continued

| | |
|---|---|
| caaagttttt caacggtttg agaccgtccg ccgtaggcat gctttgagc gtttgaccaa | 5160 |
| gcagttccag gcggtcccac agctcggtca cctgctctac ggcatctcga tccagcatat | 5220 |
| ctcctcgttt cgcgggttgg ggcggctttc gctgtacggc agtagtcggt gctcgtccag | 5280 |
| acgggccagg gtcatgtctt ccacggggcg caggtcctc gtcagcgtag tctgggtcac | 5340 |
| ggtgaagggg tgcgctccgg gctgcgcgct ggccagggtg cgcttgaggc tggtcctgct | 5400 |
| ggtgctgaag cgctgccggt cttcgccctg cgcgtcggcc aggtagcatt tgaccatggt | 5460 |
| gtcatagtcc agccctccg cggcgtggcc cttggcgcgc agcttgccct ggaggaggc | 5520 |
| gccgcacgag gggcagtgca gacttttgag ggcgtagagc ttgggcgcga gaaataccga | 5580 |
| ttccggggag taggcatccg cgccgcaggc cccgcagacg gtctcgcatt ccacgagcca | 5640 |
| ggtgagctct ggccgttcgg ggtcaaaaac caggtttccc ccatgctttt tgatgcgttt | 5700 |
| cttacctctg gtttccatga gccggtgtcc acgctcggtg acgaaaaggc tgtccgtgtc | 5760 |
| cccgtataca gacttgagag gcctgtcctc gagcggtgtt ccgcggtcct cctcgtatag | 5820 |
| aaactcggac cactctgaga caaaggctcg cgtccaggcc agcacgaagg aggctaagtg | 5880 |
| ggagggtag cggtcgttgt ccactagggg gtccactcgc tccagggtgt gaagacacat | 5940 |
| gtcgccctct tcggcatcaa ggaaggtgat tggtttgtag gtgtaggcca cgtgaccggg | 6000 |
| tgttcctgaa gggggctat aaaaggggt ggggcgcgt tcgtcctcac tctcttccgc | 6060 |
| atcgctgtct gcgagggcca gctgttgggg tgagtactcc ctctgaaaag cgggcatgac | 6120 |
| ttctgcgcta agattgtcag tttccaaaaa cgaggaggat ttgatattca cctggcccgc | 6180 |
| ggtgatgcct ttgagggtgg ccgcatccat ctggtcagaa agacaatct ttttgttgtc | 6240 |
| aagcttggtg gcaaacgacc cgtagagggc gttggacagc aacttggcga tggagcgcag | 6300 |
| ggtttggttt ttgtcgcgat cggcgcgctc cttggccgcg atgtttagct gcacgtattc | 6360 |
| gcgcgcaacg caccgccatt cgggaaagac ggtggtgcgc tcgtcgggca ccaggtgcac | 6420 |
| gcgccaaccg cggttgtgca gggtgacaag gtcaacgctg gtggctacct ctccgcgtag | 6480 |
| gcgctcgttg gtccagcaga ggcggccgcc cttgcgcgag cagaatggcg gtaggggtc | 6540 |
| tagctgcgtc tcgtccgggg ggtctgcgtc cacggtaaag accccgggca gcaggcgcgc | 6600 |
| gtcgaagtag tctatcttgc atccttgcaa gtctagcgcc tgctgccatg cgcgggcggc | 6660 |
| aagcgcgcgc tcgtatgggt tgagtggggg accccatggc atgggtggg tgagcgcgga | 6720 |
| ggcgtacatg ccgcaaatgt cgtaaacgta gaggggctct ctgagtattc caagatatgt | 6780 |
| agggtagcat cttccaccgc ggatgctggc gcgcacgtaa tcgtatagtt cgtgcgaggg | 6840 |
| agcgaggagg tcgggaccga ggttgctacg ggcgggctgc tctgctcgga agactatctg | 6900 |
| cctgaagatg gcatgtgagt tggatgatat ggttggacgc tggaagacgt tgaagctggc | 6960 |
| gtctgtgaga cctaccgcgt cacgcacgaa ggaggcgtag gagtcgcgca gcttgttgac | 7020 |
| cagctcggcg gtgacctgca cgtctagggc gcagtagtcc agggtttcct tgatgatgtc | 7080 |
| atacttatcc tgtccctttt ttttccacag ctcgcggttg aggacaaact cttcgcggtc | 7140 |
| tttccagtac tcttggatcg gaaacccgtc ggcctccgaa cggtaagagc ctagcatgta | 7200 |
| gaactggttg acggcctggt aggcgcagca tcccttttct acgggtagcg cgtatgcctg | 7260 |
| cgcggccttc cggagcgagg tgtgggtgag cgcaaaggtg tccctgacca tgactttgag | 7320 |
| gtactggtat ttgaagtcag tgtcgtcgca tccgccctgc tcccagagca aaaagtccgt | 7380 |
| gcgcttttttg gaacgcggat ttggcaggc gaaggtgaca tcgttgaaga gtatcttttcc | 7440 |
| cgcgcgaggc ataaagttgc gtgtgatgcg gaagggtccc ggcacctcgg aacggttgtt | 7500 |

-continued

```
aattacctgg gcggcgagca cgatctcgtc aaagccgttg atgttgtggc ccacaatgta      7560
aagttccaag aagcgcggga tgcccttgat ggaaggcaat tttttaagtt cctcgtaggt      7620
gagctcttca ggggagctga gcccgtgctc tgaaagggcc cagtctgcaa gatgagggtt      7680
ggaagcgacg aatgagctcc acaggtcacg ggccattagc atttgcaggt ggtcgcgaaa      7740
ggtcctaaac tggcgaccta tggccatttt ttctggggtg atgcagtaga aggtaagcgg      7800
gtcttgttcc cagcggtccc atccaaggtt cgcggctagg tctcgcgcgg cagtcactag      7860
aggctcatct ccgccgaact tcatgaccag catgaagggc acgagctgct tcccaaaggc      7920
ccccatccaa gtataggtct ctacatcgta ggtgacaaag agacgctcgg tgcgaggatg      7980
cgagccgatc gggaagaact ggatctcccg ccaccaattg gaggagtggc tattgatgtg      8040
gtgaaagtag aagtccctgc gacgggccga acactcgtgc tggcttttgt aaaaacgtgc      8100
gcagtactgc cagcggtgca cggctgtac atcctgcacg aggttgacct gacgaccgcg       8160
cacaaggaag cagagtggga atttgagccc ctcgcctggc gggtttggct ggtggtcttc      8220
tacttcggct gcttgtcctt gaccgtctgg ctgctcgagg ggagttacgg tggatcggac      8280
caccacgccg cgcgagccca aagtccagat gtccgcgcgc ggcggtcgga gcttgatgac      8340
aacatcgcgc agatgggagc tgtccatggt ctggagctcc cgcggcgtca ggtcaggcgg      8400
gagctcctgc aggtttacct cgcatagacg ggtcagggcg cgggctagat ccaggtgata      8460
cctaatttcc aggggctggt tggtggcggc gtcgatggct tgcaagaggc cgcatccccg      8520
cggcgcgact acggtaccgc gcggcgggcg gtgggccgcg ggggtgtcct tggatgatgc      8580
atctaaaagc ggtgacgcgg gcgagccccc ggaggtaggg ggggctccgg acccgccggg      8640 agaggggggca ggggcacgtc ggcgccgcgc gcgggcagga gctggtgctg cgcgcgtagg     8700
ttgctggcga acgcgacgac gcggcggttg atctcctgaa tctggcgcct ctgcgtgaag      8760
acgacgggcc cggtgagctt gagcctgaaa gagagttcga cagaatcaat ttcggtgtcg      8820 ttgacgcgg cctggcgcaa aatctcctgc acgtctcctg agttgtcttg ataggcgatc       8880
tcggccatga actgctcgat ctcttcctcc tggagatctc cgcgtccggc tcgctccacg      8940
gtggcggcga ggtcgttgga aatgcgggcc atgagctgcg agaaggcgtt gaggcctccc     9000
tcgttccaga cgcggctgta gaccacgccc ccttcggcat cgcgggcgcg catgaccacc      9060
tgcgcgagat tgagctccac gtgccgggcg aagacgcgt agtttcgcag gcgctgaaag      9120
aggtagttga gggtggtggc ggtgtgttct gccacgaaga agtacataac ccagcgtcgc      9180
aacgtggatt cgttgatatc ccccaaggcc tcaaggcgct ccatggcctc gtagaagtcc      9240
acggcgaagt tgaaaaactg ggagttgcgc gccgacacgg ttaactcctc ctccagaaga     9300
cggatgagct cggcgacagt gtcgcgcacc tcgcgctcaa aggctacagg ggcctcttct      9360
tcttcttcaa tctcctcttc cataaggcc tccccttctt cttcttctgg cggcggtggg      9420
ggagggggga cacggcggcg acgacggcgc accgggaggc ggtcgacaaa gcgctcgatc      9480
atctccccgc ggcgacggcg catggtctcg gtgacgcgc ggccgttctc gcgggggcgc      9540
agttggaaga cgccgcccgt catgtcccgg ttatgggttg gcgggggct gccatgcggc       9600 agggatacgg cgctaacgat gcatctcaac aattgttgtg taggtactcc gccgccgagg      9660
gacctgagcg agtccgcatc gaccggatcg gaaaacctct cgagaaaggc gtctaaccag      9720
tcacagtcgc aaggtaggct gagcaccgtg gcggcggca gcgggcggcg gtcgggggttg      9780 tttctggcgg aggtgctgct gatgatgtaa ttaaagtagg cggtcttgag acggcggatg      9840
```

-continued

```
gtcgacagaa gcaccatgtc cttgggtccg gcctgctgaa tgcgcaggcg gtcggccatg    9900
ccccaggctt cgttttgaca tcggcgcagg tctttgtagt agtcttgcat gagcctttct    9960
accggcactt cttcttctcc ttcctcttgt cctgcatctc ttgcatctat cgctgcggcg   10020
gcggcggagt ttggccgtag gtggcgccct cttcctccca tgcgtgtgac cccgaagccc   10080
ctcatcggct gaagcagggc taggtcggcg acaacgcgct cggctaatat ggcctgctgc   10140
acctgcgtga gggtagactg gaagtcatcc atgtccacaa agcggtggta tgcgcccgtg   10200
ttgatggtgt aagtgcagtt ggccataacg gaccagttaa cggtctggtg acccggctgc   10260
gagagctcgg tgtacctgag acgcgagtaa gccctcgagt caaatacgta gtcgttgcaa   10320
gtccgcacca ggtactggta tcccaccaaa aagtgcggcg gcggctggcg gtagaggggc   10380
cagcgtaggg tggccggggc tccggggggcg agatcttcca acataaggcg atgatatccg   10440
tagatgtacc tggacatcca ggtgatgccg gcggcggtgg tggaggcgcg cggaaagtcg   10500
cggacgcggt tccagatgtt gcgcagcggc aaaaagtgct ccatggtcgg gacgctctgg   10560
ccggtcaggc gcgcgcaatc gttgacgctc tagaccgtgc aaaaggagag cctgtaagcg   10620
ggcactcttc cgtggtctgg tggataaatt cgcaagggta tcatggcgga cgaccggggt   10680
tcgagccccg tatccggccg tccgccgtga tccatgcggt taccgcccgc gtgtcgaacc   10740
caggtgtgcg acgtcagaca acgggggagt gctccttttg gcttccttcc aggcgcggcg   10800
gctgctgcgc tagcttttt ggccactggc cgcgcgcagc gtaagcggtt aggctggaaa   10860
gcgaaagcat taagtggctc gctccctgta gccggagggt tattttccaa gggttgagtc   10920
gcgggacccc cggttcgagt ctcggaccgg ccggactgcg gcgaacgggg gtttgcctcc   10980
ccgtcatgca agacccgct tgcaaattcc tccggaaaca gggacgagcc ccttttttgc   11040
tttttcccaga tgcatccggt gctgcggcag atgcgccccc ctcctcagca gcggcaagag   11100
caagagcagc ggcagacatg cagggcaccc tcccctcctc ctaccgcgtc aggaggggcg   11160
acatccgcgg ttgacgcggc agcagatggt gattacgaac cccgcggcg ccgggcccgg   11220
cactacctgg acttggagga gggcgagggc ctggcgcggc taggacgcc ctctcctgag   11280
cggtacccaa gggtgcagct gaagcgtgat acgcgtgagg cgtacgtgcc gcggcagaac   11340
ctgtttcgcg accgcgaggg agaggagccc gaggagatgc gggatcgaaa gttccacgca   11400
gggcgcgagc tgcggcatgg cctgaatcgc gagcggttgc tgcgcgagga ggactttgag   11460
cccgacgcgc gaaccgggat tagtcccgcg cgcgcacacg tggcggccgc cgacctggta   11520
accgcatacg agcagacggt gaaccaggag attaactttc aaaaaagctt taacaaccac   11580
gtgcgtacgc ttgtggcgcg cgaggaggtg gctataggac tgatgcatct gtgggacttt   11640
gtaagcgcgc tggagcaaaa cccaaatagc aagccgctca tggcgcagct gttccttata   11700
gtgcagcaca gcagggacaa cgaggcattc agggatgcgc tgctaaacat agtagagccc   11760
gagggccgct ggctgctcga tttgataaac atcctgcaga gcatagtggt gcaggagcgc   11820
agcttgagcc tggctgacaa ggtggccgcc atcaactatt ccatgcttag cctgggcaag   11880
ttttacgccc gcaagatata ccatacccct tacgttccca tagacaagga ggtaaagatc   11940
gagggggttct acatgcgcat ggcgctgaag gtgcttacct tgagcgacga cctgggcgtt   12000
tatcgcaacg agcgcatcca aaggccgtg agcgtgagcc ggcggcgcga gctcagcgac   12060
cgcgagctga tgcacagcct gcaaagggcc ctggctggca cgggcagcgg cgatagagag   12120
gccgagtcct actttgacgc gggcgctgac ctgcgctggg cccaagccg acgcgccctg   12180
gaggcagctg gggccggacc tgggctggcg gtggcacccg cgcgcgctgg caacgtcggc   12240
```

```
ggcgtggagg aatatgacga ggacgatgag tacgagccag aggacggcga gtactaagcg    12300
gtgatgtttc tgatcagatg atgcaagacg caacggaccc ggcggtgcgg gcggcgctgc    12360
agagccagcc gtccggcctt aactccacgg acgactggcg ccaggtcatg gaccgcatca    12420
tgtcgctgac tgcgcgcaat cctgacgcgt tccggcagca gccgcaggcc aaccggctct    12480
ccgcaattct ggaagcggtg gtcccggcgc gcgcaaaccc cacgcacgag aaggtgctgg    12540
cgatcgtaaa cgcgctggcc gaaaacaggg ccatccggcc cgacgaggcc ggcctggtct    12600
acgacgcgct gcttcagcgc gtggctcgtt acaacagcgg caacgtgcag accaacctgg    12660
accggctggt gggggatgtg cgcgaggccg tggcgcagcg tgagcgcgcg cagcagcagg    12720
gcaacctggg ctccatggtt gcactaaacg ccttcctgag tacacagccc gccaacgtgc    12780
cgcggggaca ggaggactac accaactttg tgagcgcact gcggctaatg gtgactgaga    12840
caccgcaaag tgaggtgtac cagtctgggc cagactattt tttccagacc agtagacaag    12900
gcctgcagac cgtaaacctg agccaggctt tcaaaaactt gcagggctg tgggggtgc      12960 gggctcccac aggcgaccgc gcgaccgtgt ctagcttgct gacgcccaac tcgcgcctgt    13020
tgctgctgct aatagcgccc ttcacggaca gtggcagcgt gtcccgggac atacctag     13080 gtcacttgct gacactgtac cgcgaggcca taggtcaggc gcatgtggac gagcatactt    13140
tccaggagat tacaagtgtc agccgcgcgc tggggcagga ggacacgggc agcctggagg    13200
caaccctaaa ctacctgctg accaaccggc ggcagaagat cccctcgttg cacagtttaa    13260
acagcgagga ggagcgcatt ttgcgctacg tgcagcagag cgtgagcctt aacctgatgc    13320 gcgacgggg aacgcccagc gtggcgctgg acatgaccgc gcgcaacatg gaaccgggca    13380
tgtatgcctc aaaccggccg tttatcaacc gcctaatgga ctacttgcat cgcgcggccg    13440
ccgtgaaccc cgagtatttc accaatgcca tcttgaaccc gcactggcta ccgcccctg     13500 gtttctacac cgggggattc gaggtgcccg agggtaacga tggattcctc tgggacgaca    13560
tagacgacag cgtgttttcc ccgcaaccgc agaccctgct agagttgcaa cagcgcgagc    13620
aggcagaggc ggcgctgcga aaggaaagct tccgcaggcc aagcagcttg tccgatctag    13680
gcgctgcggc cccgcggtca gatgctagta gcccattcc aagcttgata gggtctctta    13740
ccagcactcg caccacccgc ccgcgcctgc tgggcgagga ggagtaccta aacaactcgc    13800
tgctgcagcc gcagcgcgaa aaaaacctgc ctccggcatt tcccaacaac gggatagaga    13860
gcctagtgga caagatgagt agatggaaga cgtacgcgca ggagcacagg gacgtgccag    13920
gcccgcgccc gcccaccgt cgtcaaaggc acgaccgtca gcggggtctg tgtgggagg      13980 acgatgactc ggcagacgac agcagcgtcc tggatttggg agggagtggc aacccgtttg    14040
cgcaccttcg ccccaggctg gggagaatgt tttaaaaaaa aaaagcatg atgcaaaata    14100 aaaaactcac caaggccatg gcaccgagcg ttggttttct tgtattcccc ttagtatgcg    14160
gcgcgcggcg atgtatgagg aaggtcctcc tccctcctac gagagtgtgg tgagcgcggc    14220
gccagtggcg gcggcgctgg gttctcccctt cgatgctccc ctggacccgc gtttgtgcc    14280 tccgcggtac ctgcggccta ccggggggag aaacagcatc cgttactctg agttggcacc    14340
cctattcgac accaccgtgt gtacctggt ggacaacaag tcaacggatg tggcatccct    14400
gaactaccag aacgaccaca gcaactttct gaccacggtc attcaaaaaca atgactacag    14460 cccgggggag gcaagcacac agaccatcaa tcttgacgac cggtcgcact ggggcggcga    14520
cctgaaaacc atcctgcata ccaacatgcc aaatgtgaac gagttcatgt ttaccaataa    14580
```

```
gtttaaggcg cgggtgatgg tgtcgcgctt gcctactaag gacaatcagg tggagctgaa    14640
atacgagtgg gtggagttca cgctgcccga gggcaactac tccgagacca tgaccataga    14700
ccttatgaac aacgcgatcg tggagcacta cttgaaagtg ggcagacaga acggggttct    14760
ggaaagcgac atcggggtaa agtttgacac ccgcaacttc agactggggt ttgaccccgt    14820
cactggtctt gtcatgcctg gggtatatac aaacgaagcc ttccatccag acatcatttt    14880
gctgccagga tgcggggtgg acttcaccca cagccgcctg agcaacttgt tgggcatccg    14940
caagcggcaa cccttccagg agggctttag gatcacctac gatgatctgg agggtggtaa    15000
cattcccgca ctgttggatg tggacgccta ccaggcgagc ttgaaagatg acaccgaaca    15060 gggcggggt ggcgcaggcg gcagcaacag cagtggcagc ggcgcggaag agaactccaa    15120
cgcggcagcc gcggcaatgc agccggtgga ggacatgaac gatcatgcca ttcgcggcga    15180
cacctttgcc acacgggctg aggagaagcg cgctgaggcc gaagcagcgg ccgaagctgc    15240
cgcccccgct gcgcaacccg aggtcgagaa gcctcagaag aaaccggtga tcaaaccccc    15300
gacagaggac agcaagaaac gcagttacaa cctaataagc aatgacagca ccttcaccca    15360
gtaccgcagc tggtaccttg catacaacta cggcgaccct cagaccggaa tccgctcatg    15420
gaccctgctt tgcactcctg acgtaacctg cggctcggag caggtctact ggtcgttgcc    15480
agacatgatg caagaccccg tgaccttccg ctccacgcgc cagatcagca actttccggt    15540
ggtgggcgcc gagctgttgc ccgtgcactc caagagcttc tacaacgacc aggccgtcta    15600
ctcccaactc atccgccagt ttacctctct gacccacgtg ttcaatcgct ttcccgagaa    15660
ccagattttg gcgcgcccgc cagccccac catcaccacc gtcagtgaaa acgttcctgc    15720
tctcacagat cacgggacgc taccgctgcg caacagcatc ggaggagtcc agcgagtgac    15780
cattactgac gccagacgcc gcacctgccc ctacgtttac aaggccctgg gcatagtctc    15840
gccgcgcgtc ctatcgagcc gcactttttg agcaagcatg tccatcctta tatcgcccag    15900
caataacaca ggctggggcc tgcgcttccc aagcaagatg tttggcgggg ccaagaagcg    15960
ctccgaccaa cacccagtgc gcgtgcgcgg gcactaccgc gcgccctggg gcgcgcacaa    16020
acgcggccgc actgggcgca ccaccgtcga tgacgccatc acgcgcgtgg tggaggaggc    16080
gcgcaactac acgcccacgc cgccaccagt gtccacagtg gacgcggcca ttcagaccgt    16140
ggtgcgcgga gcccggcgct atgctaaaat gaagagacgg cggaggcgcg tagcacgtcg    16200
ccaccgccgc cgaccggca ctgccgccca acgcgcggcg gcggccctgc ttaaccgcgc    16260
acgtcgcacc ggccgacggg cggccatgcg ggccgctcga aggctggccg cgggtattgt    16320
cactgtgccc cccaggtcca ggcgacgagc ggccgccgca gcagccgcgg ccattagtgc    16380
tatgactcag ggtcgcaggg gcaacgtgta ttgggtcgcg gactcggtta gcggcctgcg    16440
cgtgcccgtg cgcacccgcc cccgcgcaa ctagattgca agaaaaaact acttagactc    16500
gtactgttgt atgtatccag cggcggcggc gcgcaacgaa gctatgtcca agcgcaaaat    16560
caaagaagag atgctccagg tcatcgcgcc ggagatctat ggccccccga agaaggaaga    16620
gcaggattac aagccccgaa agctaaagcg ggtcaaaaag aaaagaaag atgatgatga    16680 tgaacttgac gacgaggtgg aactgctgca cgctaccgcg cccaggcgac gggtacagtg    16740
gaaaggtcga cgcgtaaaac gtgttttgcg acccggcacc accgtagtct ttacgcccgg    16800
tgagcgctcc acccgcacct acaagcgcgt gtatgatgag gtgtacgcg acgaggacct    16860 gcttgagcag gccaacgagc gcctcgggga gtttgcctac ggaaagcggc ataaggacat    16920
gctggcgttg ccgctggacg agggcaaccc aacacctagc ctaaagcccg taacactgca    16980
```

-continued

```
gcaggtgctg cccgcgcttg caccgtccga agaaaagcgc ggcctaaagc gcgagtctgg    17040
tgacttggca cccaccgtgc agctgatggt acccaagcgc cagcgactgg aagatgtctt    17100
ggaaaaaatg accgtggaac ctgggctgga gcccgaggtc cgcgtgcggc caatcaagca    17160
ggtggcgccg ggactggggcg tgcagaccgt ggacgttcag atacccacta ccagtagcac    17220
cagtattgcc accgccacag agggcatgga gacacaaacg tccccggttg cctcagcggt    17280
ggcggatgcc gcggtgcagg cggtcgctgc ggccgcgtcc aagacctcta cggaggtgca    17340 aacgacccg tggatgtttc gcgtttcagc cccccgcgc ccgcgcggtt cgaggaagta    17400
cggcgccgcc agcgcgctac tgcccgaata tgccctacat ccttccattg cgcctacccc    17460
cggctatcgt ggctacacct accgcccag aagacgagca actacccgac gccgaaccac    17520
cactggaacc cgccgccgcc gtcgccgtcg ccagcccgtg ctggccccga tttccgtgcg    17580
cagggtggct cgcgaaggag gcaggaccct ggtgctgcca acagcgcgct accacccccag    17640 catcgtttaa aagccggtct ttgtggttct tgcagatatg ccctcacct gccgcctccg    17700 tttcccggtg ccgggattcc gaggaagaat gcaccgtagg aggggcatgg ccggccacgg    17760
cctgacgggc ggcatgcgtc gtgcgcacca ccggcggcgg cgcgcgtcgc accgtcgcat    17820
gcgcggcggt atcctgcccc tccttattcc actgatcgcc gcggcgattg gcgccgtgcc    17880
cggaattgca tccgtggcct tgcaggcgca gagacactga ttaaaaacaa gttgcatgtg    17940
gaaaaatcaa aataaaagt ctggactctc acgctcgctt ggtcctgtaa ctattttgta    18000
gaatggaaga catcaacttt gcgtctctgg ccccgcgaca cggctcgcgc ccgttcatgg    18060
gaaactggca agatatcggc accagcaata tgagcggtgg cgccttcagc tggggctcgc    18120
tgtggagcgg cattaaaaat ttcggttcca ccgttaagaa ctatggcagc aaggcctgga    18180
acagcagcac aggccagatg ctgagggata agttgaaaga gcaaaatttc caacaaaagg    18240
tggtagatgg cctggcctct ggcattagcg gggtggtgga cctggccaac caggcagtgc    18300
aaaataagat taacagtaag cttgatcccc gccctcccgt agaggagcct ccaccggccg    18360
tggagacagt gtctccagag gggcgtggcg aaaagcgtcc gcgccccgac agggaagaaa    18420
ctctggtgac gcaaatagac gagcctcccc cgtacgagga ggcactaaag caaggcctgc    18480
ccaccacccg tcccatcgcg cccatggcta ccggagtgct gggccagcac acacccgtaa    18540
cgctggacct gcctccccc gccgacaccc agcagaaacc tgtgctgcca ggcccgaccg    18600
ccgttgttgt aaccgtcct agccgcgcgt ccctgcgccg cgccgccagc ggtccgcgat    18660
cgttgcggcc cgtagccagt ggcaactggc aaagcacact gaacagcatc gtgggtctgg    18720
gggtgcaatc cctgaagcgc cgacgatgct tctgaatagc taacgtgtcg tatgtgtgtc    18780
atgtatgcgt ccatgtcgcc gccagaggag ctgctgagcc gccgcgcgcc cgctttccaa    18840
gatggctacc ccttcgatga tgccgcagtg gtcttacatg cacatctcgg ccaggacgc    18900 ctcggagtac ctgagccccg ggctggtgca gtttgcccgc gccaccgaga cgtacttcag    18960
cctgaataac aagtttagaa accccacggt ggcgcctacg cacgacgtga ccacagaccg    19020
gtcccagcgt ttgacgctgc ggttcatccc tgtggaccgt gaggatactg cgtactcgta    19080
caaggcgcgg ttcaccctag ctgtgggtga taacgtgtg ctggacatgg cttccacgta    19140
ctttgacatc cgcggcgtgc tggacagggg ccctacttt aagccctact ctggcactgc    19200
ctacaacgcc ctggctccca aggtgcccc aaatccttgc gaatgggatg aagctgctac    19260
tgctcttgaa ataaacctag aagaagagga cgatgacaac gaagacgaag tagacgagca    19320
```

-continued

```
agctgagcag caaaaaactc acgtatttgg gcaggcgcct tattctggta taaatattac    19380
aaaggagggt attcaaatag gtgtcgaagg tcaaacacct aaatatgccg ataaaacatt    19440
tcaacctgaa cctcaaatag gagaatctca gtggtacgaa actgaaatta atcatgcagc    19500
tgggagagtc cttaaaaaga ctaccccaat gaaaccatgt tacggttcat atgcaaaacc    19560
cacaaatgaa aatggagggc aaggcattct tgtaaagcaa caaatgaaa agctagaaag    19620 tcaagtggaa atgcaatttt tctcaactac tgaggcgacc gcaggcaatg gtgataactt    19680
gactcctaaa gtggtattgt acagtgaaga tgtagatata gaaacccag acactcatat    19740 ttcttacatg cccactatta aggaaggtaa ctcacgagaa ctaatgggcc aacaatctat    19800
gcccaacagg cctaattaca ttgcttttag ggacaatttt attggtctaa tgtattacaa    19860
cagcacgggt aatatgggtg ttctggcggg ccaagcatcg cagttgaatg ctgttgtaga    19920
tttgcaagac agaaacacag agctttcata ccagcttttg cttgattcca ttggtgatag    19980
aaccaggtac ttttctatgt ggaatcaggc tgttgacagc tatgatccag atgttagaat    20040
tattgaaaat catggaactg aagatgaact tccaaattac tgctttccac tgggaggtgt    20100
gattaataca gagactctta ccaaggtaaa acctaaaaca ggtcaggaaa atggatggga    20160 aaagatgct acagaatttt cagataaaaa tgaaataaga gttggaaata attttgccat    20220
ggaaatcaat ctaaatgcca acctgtggag aaatttcctg tactccaaca tagcgctgta    20280
tttgcccgac aagctaaagt acagtccttc caacgtaaaa atttctgata acccaaacac    20340
ctacgactac atgaacaagc gagtggtggc tcccgggtta gtggactgct acattaacct    20400
tggagcacgc tggtcccttg actatatgga caacgtcaac ccatttaacc accaccgcaa    20460
tgctggcctg cgctaccgct caatgttgct ggcaatggt cgctatgtgc ccttccacat    20520
ccaggtgcct cagaagttct ttgccattaa aaacctcctt ctcctgccgg gctcatacac    20580
ctacgagtgg aacttcagga aggatgttaa catggttctg cagagctccc taggaaatga    20640
cctaagggtt gacggagcca gcattaagtt tgatagcatt tgcctttacg ccaccttctt    20700
ccccatggcc cacaacaccg cctccacgct tgaggccatg cttagaaacg acaccaacga    20760
ccagtccttt aacgactatc tctccgccgc caacatgctc taccctatac ccgccaacgc    20820
taccaacgtg cccatatcca tccctcccg caactgggcg ctttccgcg ctgggcctt    20880 cacgcgcctt aagactaagg aaaccccatc actgggctcg ggctacgacc ttattacac    20940 ctactctggc tctataccct acctagatgg aacctttac ctcaaccaca cctttaagaa    21000
ggtggccatt accttttgact cttctgtcag ctggcctggc aatgaccgcc tgcttacccc    21060
caacgagttt gaaattaagc gctcagttga cggggagggt tacaacgttg cccagtgtaa    21120
catgaccaaa gactggttcc tggtacaaat gctagctaac tacaacattg gctaccaggg    21180
cttctatatc ccagagagct acaaggaccg catgtactcc ttctttagaa acttccagcc    21240
catgagccgt caggtggtgg atgatactaa atacaaggac taccaacagg tgggcatcct    21300
acaccaacac aacaactctg gatttgttgg ctaccttgcc cccaccatgc gcgaaggaca    21360
ggcctaccct gctaacttcc cctatccgct tataggcaag accgcagttg acagcattac    21420
ccagaaaaag tttctttgcg atcgcaccct ttggcgcatc ccattctcca gtaactttat    21480
gtccatgggc gcactcacag acctgggcca aaaccttctc tacgccaact ccgcccacgc    21540
gctagacatg acttttgagg tggatcccat ggacgagccc acccttcttt atgttttgtt    21600
tgaagtcttt gacgtggtcc gtgtgcaccg gccgcaccg ggcgtcatcg aaaccgtgta    21660
cctgcgcacg cccttctcgg ccggcaacgc cacaacataa agaagcaagc aacatcaaca    21720
```

-continued

```
acagctgccg ccatgggctc cagtgagcag gaactgaaag ccattgtcaa agatcttggt    21780
tgtgggccat attttttggg cacctatgac aagcgctttc caggctttgt ttctccacac    21840
aagctcgcct gcgccatagt caatacgccc ggtcgcgaga ctgggggcgt acactggatg    21900
gcctttgcct ggaacccgca ctcaaaaaca tgctacctct ttgagcccct tggcttttct    21960
gaccagcgac tcaagcaggt ttaccagttt gagtacgagt cactcctgcg ccgtagcgcc    22020
attgcttctt cccccgaccg ctgtataacg ctggaaaagt ccacccaaag cgtacagggg    22080
cccaactcgg ccgcctgtgg actattctgc tgcatgtttc tccacgcctt tgccaactgg    22140
ccccaaactc ccatggatca aaccccacc atgaaccttta ttaccggggt acccaactcc    22200
atgctcaaca gtccccaggt acagcccacc ctgcgtcgca accaggaaca gctctacagc    22260
ttcctggagc gccactcgcc ctacttccgc agccacagtg cgcagattag gagcgccact    22320
tctttttgtc acttgaaaaa catgtaaaaa taatgtacta gagacacttt caataaaggc    22380
aaatgctttt atttgtacac tctcgggtga ttatttaccc ccaccttgc cgtctgcgcc    22440 gtttaaaaat caaagggggtt ctgccgcgca tcgctatgcg ccactggcag ggacacgttg    22500
cgatactggt gtttagtgct ccacttaaac tcaggcacaa ccatccgcgg cagctcggtg    22560
aagttttcac tccacaggct gcgcaccatc accaacgcgt ttagcaggtc gggcgccgat    22620
atcttgaagt cgcagttggg gcctccgccc tgcgcgcgcg agttgcgata cacagggttg    22680
cagcactgga acactatcag cgccgggtgg tgcacgctgg ccagcacgct cttgtcggag    22740
atcagatccg cgtccaggtc ctccgcgttg ctcagggcga acggagtcaa ctttggtagc    22800
tgccttccca aaaagggcgc gtgcccaggc tttgagttgc actcgcaccg tagtggcatc    22860
aaaaggtgac cgtgcccggt ctgggcgtta ggatacagcg cctgcataaa agccttgatc    22920
tgcttaaaag ccacctgagc cttttgcgcct tcagagaaga acatgccgca agacttgccg    22980
gaaaactgat tggccggaca ggccgcgtcg tgcacgcagc accttgcgtc ggtgttggag    23040
atctgcacca catttcggcc ccaccggttc ttcacgatct tggccttgct agactgctcc    23100
ttcagcgcgc gctgcccgtt ttcgctcgtc acatccattt caatcacgtg ctccttattt    23160
atcataatgc ttccgtgtag acacttaagc tcgccttcga tctcagcgca gcggtgcagc    23220
cacaacgcgc agcccgtggg ctcgtgatgc ttgtaggtca cctctgcaaa cgactgcagg    23280
tacgcctgca ggaatcgccc catcatcgtc acaaaggtct tgttgctggt gaaggtcagc    23340
tgcaacccgc ggtgctcctc gttcagccag gtcttgcata cggccgccag agcttccact    23400
tggtcaggca gtagtttgaa gttcgccttt agatcgttat ccacgtggta cttgtccatc    23460
agcgcgcgcg cagcctccat gcccttctcc cacgcagaca cgatcggcac actcagcggg    23520
ttcatcaccg taatttcact ttccgcttcg ctgggctctt cctcttcctc ttgcgtccgc    23580
ataccacgcg ccactgggtc gtcttcattc agccgccgca ctgtgcgctt acctcctttg    23640
ccatgcttga ttagcaccgg tgggttgctg aaacccacca tttgtagcgc cacatcttct    23700 cttcttcct cgctgtccac gattacctct ggtgatggcg ggcgctcggg cttgggagaa    23760
gggcgcttct ttttcttctt gggcgcaatg gccaaatccg ccgccgaggt cgatggccgc    23820
gggctgggtg tgcgcggcac cagcgcgtct tgtgatgagt cttcctcgtc ctcggactcg    23880
atacgccgcc tcatccgctt ttttgggggc gcccggggag gcggcggcga cggggacggg    23940
gacgacacgt cctccatggt tgggggacgt cgcgccgcac cgcgtccgcg ctcggggtg    24000 gtttcgcgct gctcctcttc ccgactggcc atttccttct cctataggca gaaaaagatc    24060
```

```
atggagtcag tcgagaagaa ggacagccta accgcccct ctgagttcgc caccaccgcc    24120
tccaccgatg ccgccaacgc gcctaccacc ttccccgtcg aggcaccccc gcttgaggag    24180
gaggaagtga ttatcgagca ggacccaggt tttgtaagcg aagacgacga ggaccgctca    24240
gtaccaacag aggataaaaa gcaagaccag acaacgcag aggcaaacga ggaacaagtc     24300
gggcgggggg acgaaaggca tggcgactac ctagatgtgg gagacgacgt gctgttgaag    24360
catctgcagc gccagtgcgc cattatctgc gacgcgttgc aagagcgcag cgatgtgccc    24420
ctcgccatag cggatgtcag ccttgcctac gaacgccacc tattctcacc gcgcgtaccc    24480
cccaaacgcc aagaaaacgg cacatgcgag cccaacccgc gcctcaactt ctaccccgta    24540
tttgccgtgc cagaggtgct tgccacctat cacatctttt tccaaaactg caagataccc    24600
ctatcctgcc gtgccaaccg cagccgagcg acaagcagc tggccttgcg gcagggcgct     24660
gtcatacctg atatcgcctc gctcaacgaa gtgccaaaaa tctttgaggg tcttggacgc    24720
gacgagaagc gcgcggcaaa cgctctgcaa caggaaaaca gcgaaaatga aagtcactct    24780
ggagtgttgg tggaactcga gggtgacaac gcgcgcctag ccgtactaaa acgcagcatc    24840
gaggtcaccc actttgccta cccggcactt aacctacccc ccaaggtcat gagcacagtc    24900
atgagtgagc tgatcgtgcg ccgtgcgcag cccctggaga gggatgcaaa tttgcaagaa    24960
caaacagagg agggcctacc cgcagttggc gacgagcagc tagcgcgctg gcttcaaacg    25020
cgcgagcctg ccgacttgga ggagcgacgc aaactaatga tggccgcagt gctcgttacc    25080
gtggagcttg agtgcatgca gcggttcttt gctgacccgg agatgcagcg caagctagag    25140
gaaacattgc actacacctt tcgacagggc tacgtacgcc aggcctgcaa gatctccaac    25200
gtggagctct gcaacctggt ctcctacctt ggaattttgc acgaaaaccg ccttgggcaa    25260
aacgtgcttc attccacgct caagggcgag gcgcgccgcg actacgtccg cgactgcgtt    25320
tactatttc tatgctacac ctggcagacg gccatgggcg tttggcagca gtgcttggag     25380
gagtgcaacc tcaaggagct gcagaaactg ctaaagcaaa acttgaagga cctatggacg    25440
gccttcaacg agcgctccgt ggccgcgcac ctggcggaca tcatttttcc cgaacgcctg    25500
cttaaaaccc tgcaacaggg tctgccagac ttcaccagtc aaagcatgtt gcagaacttt    25560
aggaactta tcctagagcg ctcaggaatc ttgcccgcca cctgctgtgc acttcctagc     25620
gactttgtgc ccattaagta ccgcgaatgc cctccgccgc tttggggcca ctgctacctt    25680
ctgcagctag ccaactacct tgcctaccac tctgacataa tggaagacgt gagcggtgac    25740
ggtctactgg agtgtcactg tcgctgcaac ctatgcaccc cgcaccgctc cctggtttgc    25800
aattcgcagc tgcttaacga aagtcaaatt atcggtacct tgagctgca gggtccctcg     25860
cctgacgaaa gtccgcggc tccggggttg aaactcactc cggggctgtg acgtcggct      25920
taccttcgca aatttgtacc tgaggactac cacgcccacg agattaggtt ctacgaagac    25980
caatcccgcc cgccaaatgc ggagcttacc gcctgcgtca ttacccaggg ccacattctt    26040
ggccaattgc aagccatcaa caagcccgc caagagtttc tgctacgaaa gggacggggg     26100
gtttacttgg accccagtc cggcgaggag ctcaacccaa tcccccgcc gccgcagccc     26160
tatcagcagc agccgcgggc ccttgcttcc caggatggca cccaaaaaga agctgcagct    26220
gccgccgcca cccacggacg aggaggaata ctgggacagt caggcagagg aggttttgga    26280
cgaggaggag gaggacatga tggaagactg ggagagccta gacgaggaag cttccgaggt    26340
cgaagaggtg tcagacgaaa caccgtcacc ctcggtcgca ttccctcgc ggcgccccca     26400
gaaatcggca accggttcca gcatggctac aacctccgct cctcaggcgc cgccggcact    26460
```

-continued

```
gcccgttcgc cgacccaacc gtagatggga caccactgga accagggccg gtaagtccaa  26520
gcagccgccg ccgttagccc aagagcaaca acagcgccaa ggctaccgct catggcgcgg  26580
gcacaagaac gccatagttg cttgcttgca agactgtggg ggcaacatct ccttcgcccg  26640
ccgctttctt ctctaccatc acggcgtggc cttccccgt aacatcctgc attactaccg  26700
tcatctctac agcccatact gcaccggcgg cagcggcagc ggcagcaaca gcagcggcca  26760
cacagaagca aaggcgaccg gatagcaaga ctctgacaaa gcccaagaaa tccacagcgg  26820
cggcagcagc aggaggagga gcgctgcgtc tggcgcccaa cgaacccgta tcgacccgcg  26880
agcttagaaa caggattttt cccactctgt atgctatatt tcaacagagc aggggccaag  26940
aacaagagct gaaaataaaa aacaggtctc tgcgatccct cacccgcagc tgcctgtatc  27000
acaaaagcga agatcagctt cggcgcacgc tggaagacgc ggaggctctc ttcagtaaat  27060
actgcgcgct gactcttaag gactagtttc gcgccctttc tcaaatttaa gcgcgaaaac  27120
tacgtcatct ccagcggcca cacccggcgc cagcacctgt cgtcagcgcc attatgagca  27180
aggaaattcc cacgccctac atgtggagtt accagccaca aatgggactt gcggctggag  27240
ctgcccaaga ctactcaacc cgaataaact acatgagcgc gggaccccac atgatatccc  27300
gggtcaacgg aatccgcgcc caccgaaacc gaattctctt ggaacaggcg gctattacca  27360
ccacacctcg taataacctt aatccccgta gttggcccgc tgccctggtg taccaggaaa  27420
gtcccgctcc caccactgtg gtacttccca gagacgccca ggccgaagtt cagatgacta  27480
actcaggggc gcagcttgcg ggcggctttc gtcacagggt gcggtcgccc gggcagggta  27540
taactcacct gacaatcaga gggcgaggta ttcagctcaa cgacgagtcg gtgagctcct  27600
cgcttggtct ccgtccggac gggacatttc agatcggcgg cgccggccgt ccttcattca  27660
cgcctcgtca ggcaatccta actctgcaga cctcgtcctc tgagccgcgc tctggaggca  27720
ttggaactct gcaatttatt gaggagtttg tgccatcggt ctactttaac cccttctcgg  27780
gacctcccgg ccactatccg gatcaattta ttcctaactt tgacgcggta aaggactcgg  27840
cggacggcta cgactgaatg ttaagtggag aggcagagca actgcgcctg aaacacctgg  27900
tccactgtcg ccgccacaag tgctttgccc gcgactccgg tgagttttgc tactttgaat  27960
tgcccgagga tcatatcgag ggcccggcgc acggcgtccg gcttaccgcc cagggagagc  28020
ttgcccgtag cctgattcgg gagtttaccc agcgcccct gctagttgag cgggacaggg  28080
gaccctgtgt tctcactgtg atttgcaact gtcctaacct tggattacat caagatcttt  28140
gttgccatct ctgtgctgag tataataaat acagaaatta aaatatactg gggtccctat  28200
cgccatcctg taaacgccac cgtcttcacc cgcccaagca aaccaaggcg aaccttacct  28260 ggtacttta acatctctcc ctctgtgatt tacaacagtt tcaacccaga cggagtgagt  28320
ctacgagaga acctctccga gctcagctac tccatcagaa aaaacaccac cctccttacc  28380
tgccgggaac gtacgagtgc gtcaccggcc gctgcaccac acctaccgcc tgaccgtaaa  28440
ccagactttt tccggacaga cctcaataac tctgtttacc agaacaggag gtgagcttag  28500 aaaacccttta gggtattagg ccaaaggcgc agctactgtg gggtttatga acaattcaag  28560
caactctacg ggctattcta attcaggttt ctctagaagt caggcttcct ggatgtcagc  28620
atctgacttt ggccagcacc tgtcccgcgg atttgttcca gtccaactac agcgacccac  28680
cctaacagag atgaccaaca caaccaacgc ggccgccgct accggactta catctaccac  28740
aaatacaccc caagtttctg cctttgtcaa taactgggat aacttgggca tgtggtggtt  28800
```

-continued

```
ctccatagcg cttatgtttg tatgccttat tattatgtgg ctcatctgct gcctaaagcg    28860
caaacgcgcc cgaccaccca tctatagtcc catcattgtg ctacacccaa acaatgatgg    28920
aatccataga ttggacggac tgaaacacat gttcttttct cttacagtat gattaaatga    28980
gatctagaaa tggacggaat tattacagag cagcgcctgc tagaaagacg cagggcagcg    29040
gccgagcaac agcgcatgaa tcaagagctc aagacatgg ttaacttgca ccagtgcaaa     29100 agggggtatct tttgtctggt aaagcaggcc aaagtcacct acgacagtaa taccaccgga   29160
caccgcctta gctacaagtt gccaaccaag cgtcagaaat tggtggtcat ggtgggagaa    29220
aagcccatta ccataactca gcactcggta gaaaccgaag gctgcattca ctcaccttgt    29280
caaggacctg aggatctctg caccctttatt aagaccctgt gcggtctcaa agatcttatt   29340 cccttttaact aataaaaaaa aataataaag catcacttac ttaaaatcag ttagcaaatt   29400
tctgtccagt ttattcagca gcacctcctt gccctcctcc cagctctggt attgcagctt    29460
cctcctggct gcaaactttc tccacaatct aaatggaatg tcagtttcct cctgttcctg    29520
tccatccgca cccactatct tcatgttgtt gcagatgaag cgcgcaagac cgtctgaaga    29580
taccttcaac cccgtgtatc catatgacac ggaaaccggt cctccaactg tgccttttct    29640
tactcctccc tttgtatccc ccaatgggtt tcaagagagt cccctgggg tactctcttt     29700 gcgcctatcc gaacctctag ttacctccaa tggcatgctt gcgctcaaaa tgggcaacgg    29760
cctctctctg gacgaggccg gcaaccttac ctcccaaaat gtaaccactg tgagcccacc    29820
tctcaaaaaa accaagtcaa acataaacct ggaaatatct gcacccctca cagttacctc    29880
agaagcccta actgtggctg ccgccgcacc tctaatggtc gcgggcaaca cactcaccat    29940
gcaatcacag gccccgctaa ccgtgcacga ctccaaactt agcattgcca cccaaggacc    30000
cctcacagtg tcagaaggaa agctagccct gcaaacatca ggccccctca ccaccaccga    30060
tagcagtacc cttactatca ctgcctcacc ccctctaact actgccactg gtagcttggg    30120
cattgacttg aaagagccca tttatacaca aaatggaaaa ctaggactaa agtacgggc     30180 tcctttgcat gtaacagacg acctaaacac tttgaccgta gcaactggtc caggtgtgac    30240
tattaataat acttccttgc aaactaaagt tactggagcc ttgggttttg attcacaagg    30300
caatatgcaa cttaatgtag caggaggact aaggattgat tctcaaaaca gacgccttat    30360
acttgatgtt agttatccgt ttgatgctca aaaccaacta aatctaagac taggacaggg    30420
ccctcttttt ataaactcag cccacaactt ggatattaac tacaacaaag gcctttactt   30480
gtttacagct tcaaacaatt ccaaaaagct tgaggttaac ctaagcactg ccaagggggtt   30540 gatgtttgac gctacagcca tagccattaa tgcaggagat gggcttgaat ttggttcacc    30600
taatgcacca aacacaaatc ccctcaaaac aaaaattggc catggcctag aatttgattc    30660
aaacaaggct atggttccta aactaggaac tggccttagt tttgacagca caggtgccat    30720
tacagtagga aacaaaaata atgataagct aactttgtgg accacaccag ctccatctcc    30780
taactgtaga ctaaatgcag agaaagatgc taaactcact ttggtcttaa caaaatgtgg    30840
cagtcaaata cttgctacag tttcagtttt ggctgttaaa ggcagtttgg ctccaatatc    30900
tggaacagtt caaagtgctc atcttattat aagatttgac gaaaatggag tgctactaaa    30960
caattccttc ctggacccag aatattggaa ctttagaaat ggagatctta ctgaaggcac    31020
agcctataca aacgctgttg gatttatgcc taacctatca gcttatccaa aatctcacgg    31080
taaaactgcc aaaagtaaca ttgtcagtca agttactta aacggagaca aaactaaacc    31140
tgtaacacta accattacac taaacggtac acaggaaaca ggagacacaa ctccaagtgc    31200
```

```
atactctatg tcattttcat gggactggtc tggccacaac tacattaatg aaatatttgc    31260
cacatcctct tacactttt catacattgc ccaagaataa agaatcgttt gtgttatgtt    31320
tcaacgtgtt tattttcaa ttgcagaaaa tttcaagtca tttttcattc agtagtatag    31380
ccccaccacc acatagctta tacagatcac cgtaccttaa tcaaactcac agaaccctag    31440
tattcaacct gccacctccc tcccaacaca cagagtacac agtcctttct ccccggctgg    31500
ccttaaaaag catcatatca tgggtaacag acatattctt aggtgttata ttccacacgg    31560
tttcctgtcg agccaaacgc tcatcagtga tattaataaa ctccccgggc agctcactta    31620
agttcatgtc gctgtccagc tgctgagcca caggctgctg tccaacttgc ggttgcttaa    31680
cgggcggcga aggagaagtc cacgcctaca tgggggtaga gtcataatcg tgcatcagga    31740
tagggcggtg gtgctgcagc agcgcgcgaa taaactgctg ccgccgccgc tccgtcctgc    31800
aggaatacaa catggcagtg gtctcctcag cgatgattcg caccgcccgc agcataaggc    31860
gccttgtcct ccgggcacag cagcgcaccc tgatctcact taaatcagca cagtaactgc    31920
agcacagcac cacaatattg ttcaaaatcc cacagtgcaa ggcgctgtat ccaaagctca    31980
tggcggggac cacagaaccc acgtggccat cataccacaa gcgcaggtag attaagtggc    32040 gaccctcat aaacacgctg gacataaaca ttacctcttt tggcatgttg taattccacca    32100 cctcccggta ccatataaac ctctgattaa acatggcgcc atccaccacc atcctaaacc    32160
agctggccaa aacctgcccg ccggctatac actgcaggga accggactg gaacaatgac    32220 agtggagagc ccaggactcg taaccatgga tcatcatgct cgtcatgata tcaatgttgg    32280
cacaacacag gcacacgtgc atacacttcc tcaggattac aagctcctcc cgcgttagaa    32340
ccatatccca gggaacaacc cattcctgaa tcagcgtaaa tcccacactg cagggaagac    32400
ctcgcacgta actcacgttg tgcattgtca aagtgttaca ttcgggcagc agcggatgat    32460
cctccagtat ggtagcgcgg gtttctgtct caaaaggagg tagacgatcc ctactgtacg    32520
gagtgcgccg agacaaccga gatcgtgttg gtcgtagtgt catgccaaat ggaacgccgg    32580
acgtagtcat atttcctgaa gcaaaaccag gtgcgggcgt gacaaacaga tctgcgtctc    32640
cggtctcgcc gctagatcg ctctgtgtag tagttgtagt atatccactc tctcaaagca    32700
tccaggcgcc ccctggcttc gggttctatg taaactcctt catgcgccgc tgccctgata    32760
acatccacca ccgcagaata agccacaccc agccaaccta cacattcgtt ctgcgagtca    32820
cacacgggag gagcgggaag agctggaaga accatgtttt ttttttatt ccaaaagatt    32880 atccaaaacc tcaaaatgaa gatctattaa gtgaacgcgc tcccctccgg tggcgtggtc    32940
aaactctaca gccaaagaac agataatggc atttgtaaga tgttgcacaa tggcttccaa    33000
aaggcaaacg gccctcacgt ccaagtggac gtaaaggcta aacccttcag ggtgaatctc    33060
ctctataaac attccagcac cttcaaccat gcccaaataa ttctcatctc gccaccttct    33120
caatatatct ctaagcaaat cccgaatatt aagtccggcc attgtaaaaa tctgctccag    33180
agcgccctcc accttcagcc tcaagcagcg aatcatgatt gcaaaaattc aggttcctca    33240
cagacctgta taagattcaa aagcggaaca ttaacaaaaa taccgcgatc ccgtaggtcc    33300
cttcgcaggg ccagctgaac ataatcgtgc aggtctgcac ggaccagcgc ggccacttcc    33360
ccgccaggaa ccttgacaaa agaacccaca ctgattatga cacgcatact cggagctatg    33420
ctaaccagcg tagcccccgat gtaagctttg ttgcatgggc ggcgatataa aatgcaaggt    33480
gctgctcaaa aaatcaggca aagcctcgcg caaaaaagaa agcacatcgt agtcatgctc    33540
```

-continued

| | | | | |
|---|---|---|---|---|
| atgcagataa | aggcaggtaa | gctccggaac | caccacagaa | aaagcacca ttttctctc 33600 |
| aaacatgtct | gcgggtttct | gcataaacac | aaaataaaat | aacaaaaaaa catttaaaca 33660 |
| ttagaagcct | gtcttacaac | aggaaaaaca | acccttataa | gcataagacg gactacggcc 33720 |
| atgccggcgt | gaccgtaaaa | aaactggtca | ccgtgattaa | aaagcaccac cgacagctcc 33780 |
| tcggtcatgt | ccggagtcat | aatgtaagac | tcggtaaaca | catcaggttg attcatcggt 33840 |
| cagtgctaaa | aagcgaccga | aatagcccgg | gggaatacat | acccgcaggc gtagagacaa 33900 |
| cattacagcc | cccataggag | gtataacaaa | attaatagga | gagaaaaaca cataaacacc 33960 |
| tgaaaaaccc | tcctgcctag | gcaaaatagc | accctcccgc | tccagaacaa catacagcgc 34020 |
| ttcacacgcg | cagcctaaca | gtcagcctta | ccagtaaaaa | agaaaaccta ttaaaaaaac 34080 |
| accactcgac | acggcaccag | ctcaatcagt | cacagtgtaa | aaaagggcca agtgcagtaa 34140 |
| tcagcgctgc | ctgaaactcg | cgccgcgagg | agagggcggg | gccgcggaaa ggaaggggag 34200 |
| gggctgggag | ggcccggagg | gggctgggcc | ggggacccgg | gaggggtcgg gacggggcgg 34260 |
| ggtccgcgcg | gaggaggcgg | agctggaagg | tgaaggggca | ggacgggtgc ccgggtcccc 34320 |
| agtccctccg | ccacgtggga | agcgcggtcc | tgggcgtctg | tgcccgcgaa tccactggga 34380 |
| gcccggcctg | gccccgacag | cgcagctgct | ccgggcggac | ccgggggtct gggccgcgct 34440 |
| tccccgcccg | cgcgccgctc | gcgctcccag | ggtgcaggga | cgccagcgag ggccccagcg 34500 |
| gagagaggtc | gaatcggcct | aggctgtggg | gtaacccgag | ggaggggcca tgatgtggag 34560 |
| gccctgggaa | caggtgcgtg | cggcgaccct | ttggccgctg | gcctgatccg gagacccagg 34620 |
| gctgcctcca | ggtccggacg | cggggcgtcg | ggctccgggc | accacgaatg ccggacgtga 34680 |
| aggggaggac | ggaggcgcgt | agacgcggct | ggggacgaac | ccgaggacgc attgctccct 34740 |
| ggacgggcac | gcgggacctc | ccggagtgcc | tccctgcaac | acttccccgc gacttgggct 34800 |
| ccttgacaca | ggcccgtcat | ttctctttgc | aggttctcag | gcggcgaggg gtccccacca 34860 |
| tgagcaaacc | accccaaatc | tgttaatcac | ccaccggggc | ggtcccgtcg agaaagggtg 34920 |
| ggaaatggag | ccaggcgctc | ctgctggccg | cgcaccgggc | gcctcacacc agccacaacg 34980 |
| gccttgaccc | tgggccccgg | cactctgtct | ggcagatgag | gccaacatct ggtcacatcc 35040 |
| cgcccgcaca | gggtggaggg | cagcctcggg | gtccaggcac | ctggctccaa gcctcggact 35100 |
| gcagagctag | gaggcccgac | ttccagccca | gcagtagaag | ccacacggcc actggtcccc 35160 |
| tccagacctg | ggccccggc | acaaccgcag | gacagctgag | gacttcccag gaatccagac 35220 |
| tccgggttgc | tcaagtttgg | atctaagggg | cgagaaactt | ctgggtctcc cgaggccttg 35280 |
| cagggatgct | gtagctgagg | tcggcaaaca | ctgaaatgct | aacaaacgca accttaaatg 35340 |
| taacctttcc | tactttcaga | aactgccgga | ggaaattgct | ttatttatgg agctagcatt 35400 |
| tgaacaggcc | tcgcaccctc | cctgggctgt | cacgctcgct | ggaggttagc ctcgtcttgt 35460 |
| aaatacttag | gattacgggt | cgctcttcta | gaaatcccct | tagtgatccc taagcctttt 35520 |
| taaagggctg | tgtttgtgaa | ttgtctctgc | cactagggca | aagggcggt ttggaaaatt 35580 |
| tgttccaaca | aaagttaagt | tgtagcttac | actggttctc | tgcagagaag ccaacataga 35640 |
| aaacacaatt | ttaaagagg | gaagagaaga | aatggaagca | gaagattatg ctggagtaat 35700 |
| taacaccatg | tgcatggcga | ggaaacgcct | cccggcattc | aatgaagatc gctgataccc 35760 |
| agaagacacc | ccagtattat | gggtgcagtt | agtgtgtctt | tgaaaagctg atgattactt 35820 |
| cccattttaa | gaaaactaca | attcccaaca | catacaagtt | actccgccct aaaacctacg 35880 |
| tcacccgccc | cgttcccacg | ccccgcgcca | cgtcacaaac | tccacccct cattatcata 35940 |

-continued ttggcttcaa tccaaaataa ggtatattat tgatgatg                                35978

<210> SEQ ID NO 2
<211> LENGTH: 35871
<212> TYPE: DNA
<213> ORGANISM: Adenovirus

<400> SEQUENCE: 2

| | | | | | |
|---|---|---|---|---|---|
| catcatcaat | aatatacctt | attttggatt | gaagccaata | tgataatgag | ggggtggagt | 60 |
| ttgtgacgtg | gcgcggggcg | tgggaacggg | gcgggtgacg | tagtagtgtg | gcggaagtgt | 120 |
| gatgttgcaa | gtgtggcgga | acacatgtaa | gcgacggatg | tggcaaaagt | gacgttttg | 180 |
| gtgtgcgccg | gtgtacacag | gaagtgacaa | ttttcgcgcg | gttttaggcg | gatgttgtag | 240 |
| taaatttggg | cgtaaccgag | taagatttgg | ccattttcgc | gggaaaactg | aataagagga | 300 |
| agtgaaatct | gaataatttt | gtgttactca | tagcgcgtaa | tatttgtcta | gggccgcggg | 360 |
| gactttgacc | gtttacgtgg | agactcgccc | aggtgttttt | ctcaggtgtt | ttccgcgttc | 420 |
| cgggtcaaag | ttggcgtttt | attattatag | tcagctgacg | tgtagtgtat | ttatacccgg | 480 |
| tgagttcctc | aagaggccac | tcttgagtgc | cagcgagtag | agttttctcc | tccgagccgc | 540 |
| tccgacaccg | ggactgaaaa | tgagacatga | ggtactggct | gataatcttc | cacctcctag | 600 |
| ccattttgaa | ccacctaccc | ttcacgaact | gtatgattta | gacgtgacgg | cccccgaaga | 660 |
| tcccaacgag | gaggcggttt | cgcagatttt | tcccgactct | gtaatgttgg | cggtgcagga | 720 |
| agggattgac | ttactcactt | ttccgccggc | gcccggttct | ccggagccgc | ctcaccttc | 780 |
| ccggcagccc | gagcagccgg | agcagagagc | cttgggtccg | gtttgccacg | aggctggctt | 840 |
| tccacccagt | gacgacgagg | atgaagaggg | tgaggagttt | gtgttagatt | atgtggagca | 900 |
| ccccgggcac | ggttgcaggt | cttgtcatta | tcaccggagg | aatacggggg | acccagatat | 960 |
| tatgtgttcg | ctttgctata | tgaggacctg | tggcatgttt | gtctacagta | agtgaaaatt | 1020 |
| atgggcagtg | ggtgatagag | tggtgggttt | ggtgtggtaa | tttttttttt | aattttaca | 1080 |
| gttttgtggt | ttaaagaatt | ttgtattgtg | attttttaa | aaggtcctgt | gtctgaacct | 1140 |
| gagcctgagc | ccgagccaga | accggagcct | gcaagaccta | cccgccgtcc | taaaatggcg | 1200 |
| cctgctatcc | tgagacgccc | gacatcacct | gtgtctagag | aatgcaatag | tagtacggat | 1260 |
| agctgtgact | ccggtccttc | taacacacct | cctgagatac | accggtggt | cccgctgtgc | 1320 |
| cccattaaac | cagttgccgt | gagagttggt | gggcgtcgcc | aggctgtgga | atgtatcgag | 1380 |
| gacttgctta | cgagcctggg | caaccttg | gacttgagct | gtaaacgccc | caggccataa | 1440 |
| ggtgtaaacc | tgtgattgcg | tgtgtggtta | acgcctttgt | ttgctgaatg | agttgatgta | 1500 |
| agtttaataa | agggtgagat | aatgttaac | ttgcatggcg | tgttaaatgg | ggcggggctt | 1560 |
| aaagggtata | taatgcgccg | tgggctaatc | ttggttacat | ctgacctcat | ggaggcttgg | 1620 |
| gagtgtttgg | aagatttttc | tgctgtgcgt | aacttgctgg | aacagagctc | taacagtacc | 1680 |
| tcttggtttt | ggaggtttct | gtggggctca | tcccaggcaa | agttagtctg | cagaattaag | 1740 |
| gaggattaca | agtgggaatt | tgaagagctt | ttgaaatcct | gtggtgagct | gtttgattct | 1800 |
| ttgaatctgg | gtcaccaggc | gcttttccaa | gagaaggtca | tcaagacttt | ggattttcc | 1860 |
| acaccggggc | gcgctgcggc | tgctgttgct | ttttgagtt | ttataaagga | taaatggagc | 1920 |
| gaagaaaccc | atctgagcgg | ggggtacctg | ctggattttc | tggccatgca | tctgtgggaga | 1980 |
| gcggttgtga | gacacaagaa | tcgcctgcta | ctgttgtctt | ccgtccgccc | ggcgataata | 2040 |

-continued

```
ccgacggagg agcagcagca gcagcaggag gaagccaggc ggcggcggca ggagcagagc    2100
ccatggaacc cgagagccgg cctggaccct cgggaatgaa tgttgtacag gtggctgaac    2160
tgtatccaga actgagacgc attttgacaa ttacagagga tgggcagggg ctaaagggg     2220 taaagaggga gcggggggct tgtgaggcta cagaggaggc taggaatcta gcttttagct    2280
taatgaccag acaccgtcct gagtgtatta cttttcaaca gatcaaggat aattgcgcta    2340
atgagcttga tctgctggcg cagaagtatt ccatagagca gctgaccact tactggctgc    2400
agccagggga tgattttgag gaggctatta gggtatatgc aaaggtggca cttaggccag    2460
attgcaagta caagatcagc aaacttgtaa atatcaggaa ttgttgctac atttctggga    2520
acggggccga ggtggagata gatacggagg ataggtggc ctttagatgt agcatgataa     2580
atatgtggcc gggggtgctt ggcatggacg gggtggttat tatgaatgta aggtttactg    2640
gccccaattt tagcggtacg gttttcctgg ccaataccaa ccttatccta cacggtgtaa    2700
gcttctatgg gtttaacaat acctgtgtgg aagcctggac cgatgtaagg gttcggggct    2760 gtgccttta ctgctgctgg aagggggtgg tgtgtcgccc caaaagcagg gcttcaatta     2820
agaaatgcct ctttgaaagg tgtaccttgg gtatcctgtc tgagggtaac tccagggtgc    2880
gccacaatgt ggcctccgac tgtggttgct tcatgctagt gaaaagcgtg gctgtgatta    2940
agcataacat ggtatgtggc aactgcgagg acagggcctc tcagatgctg acctgctcgg    3000
acggcaactg tcacctgctg aagaccattc acgtagccag ccactctcgc aaggcctggc    3060
cagtgtttga gcataacata ctgacccgct gttccttgca tttgggtaac aggagggggg    3120
tgttcctacc ttaccaatgc aatttgagtc acactaagat attgcttgag cccgagagca    3180
tgtccaaggt gaacctgaac ggggtgtttg acatgaccat gaagatctgg aaggtgctga    3240
ggtacgatga gacccgcacc aggtgcagac cctgcgagtg tggcggtaaa catattagga    3300
accagcctgt gatgctggat gtgaccgagg agctgaggcc cgatcacttg gtgctggcct    3360
gcacccgcgc tgagtttggc tctagcgatg aagatacaga ttgaggtact gaaatgtgtg    3420
ggcgtggctt aagggtggga aagaatatat aaggtggggg tcttatgtag ttttgtatct    3480
gttttgcagc agccgccgcc gccatgagca ccaactcgtt tgatggaagc attgtgagct    3540
catatttgac aacgcgcatg cccccatggg ccggggtgcg tcagaatgtg atgggctcca    3600
gcattgatgg tcgccccgtc ctgcccgcaa actctactac cttgacctac gagaccgtgt    3660
ctggaacgcc gttggagact gcagcctccg ccgccgcttc agccgctgca gccaccgccc    3720
gcgggattgt gactgacttt gctttcctga gcccgcttgc aagcagtgca gcttcccgtt    3780
catccgcccg cgatgacaag ttgacggctc ttttggcaca attggattct ttgacccggg    3840
aacttaatgt cgtttctcag cagctgttgg atctgcgcca gcaggtttct gccctgaagg    3900
cttcctcccc tcccaatgcg gtttaaaaca taaataaaaa accagactct gtttggattt    3960
ggatcaagca agtgtcttgc tgtctttatt taggggtttt gcgcgcgcgg taggcccggg    4020
accagcggtc tcggtcgttg agggtcctgt gtattttttc caggacgtgg taaaggtgac    4080
tctggatgtt cagatacatg ggcataagcc cgtctctggg gtggaggtag caccactgca    4140
gagcttcatg ctgcggggtg gtgttgtaga tgatccagtc gtagcaggag cgctgggcgt    4200
ggtgcctaaa aatgtctttc agtagcaagc tgattgccag gggcaggccc ttggtgtaag    4260 tgttacaaa gcggttaagc tgggatgggt gcatacgtgg ggatatgaga tgcatcttgg     4320
actgtatttt taggttggct atgttcccag ccatatccct ccgggattc atgttgtgca     4380 gaaccaccag cacagtgtat ccggtgcact tgggaaattt gtcatgtagc ttagaaggaa    4440
```

-continued

```
atgcgtggaa gaacttggag acgcccttgt gacctccaag attttccatg cattcgtcca   4500
taatgatggc aatgggccca cgggcggcgg cctgggcgaa gatatttctg ggatcactaa   4560
cgtcatagtt gtgttccagg atgagatcgt cataggccat ttttacaaag cgcgggcgga   4620
gggtgccaga ctgcggtata atggttccat ccggcccagg ggcgtagtta ccctcacaga   4680
tttgcatttc ccacgctttg agttcagatg ggggatcat gtctacctgc ggggcgatga   4740
agaaaacggt ttccggggta ggggagatca gctgggaaga aagcaggttc ctgagcagct   4800
gcgacttacc gcagccggtg ggcccgtaaa tcacacctat taccgggtgc aactggtagt   4860
taagagagct gcagctgccg tcatccctga gcagggggc cacttcgtta agcatgtccc   4920
tgactcgcat gttttccctg accaaatccg ccagaaggcg ctcgccgccc agcgatagca   4980
gttcttgcaa ggaagcaaag ttttcaacg gtttgagacc gtccgccgta ggcatgcttt   5040
tgagcgtttg accaagcagt tccaggcggt cccacagctc ggtcacctgc tctacggcat   5100
ctcgatccag catatctcct cgtttcgcgg gttgggcgg ctttcgctgt acggcagtag   5160
tcggtgctcg tccagacggg ccagggtcat gtctttccac gggcgcaggg tcctcgtcag   5220
cgtagtctgg gtcacggtga aggggtgcgc tccgggctgc gcgctggcca gggtgcgctt   5280
gaggctggtc ctgctggtgc tgaagcgctg ccggtcttcg ccctgcgcgt cggccaggta   5340
gcatttgacc atggtgtcat agtccagccc ctccgcggcg tggcccttgg cgcgcagctt   5400
gcccttggag gaggcgccgc acgagggcca gtgcagactt ttgagggcgt agagcttggg   5460
cgcgagaaat accgattccg gggagtaggc atccgcgccg caggcccgc agacggtctc   5520 gcattccacg agccaggtga gctctggccg ttcggggtca aaaaccaggt ttccccatg   5580 cttttttgatg cgtttcttac ctctggtttc catgagccgg tgtccacgct cggtgacgaa   5640
aaggctgtcc gtgtccccgt atacagactt gagaggcctg tcctcgagcg tgttccgcg   5700 gtcctcctcg tatagaaact cggaccactc tgagacaaag gctcgcgtcc aggccagcac   5760
gaaggaggct aagtgggagg ggtagcggtc gttgtccact aggggtcca ctcgctccag   5820 ggtgtgaaga cacatgtcgc cctcttcggc atcaaggaag gtgattggtt tgtaggtgta   5880
ggccacgtga ccgggtgttc ctgaaggggg gctataaaag ggggtggggg gcgcgttcgtc   5940 ctcactctct tccgcatcgc tgtctgcgag ggccagctgt tggggtgagt actccctctg   6000
aaaagcgggc atgacttctg cgctaagatt gtcagtttcc aaaaacgagg aggatttgat   6060
attcacctgg cccgcggtga tgcctttgag ggtggccgca tccatctggt cagaaaagac   6120 aatcttttg ttgtcaagct tggtggcaaa cgacccgtag agggcgttgg acagcaactt   6180
ggcgatggag cgcagggttt ggttttttgtc gcgatcggcg cgctccttgg ccgcgatgtt   6240
tagctgcacg tattcgcgcg caacgcaccg ccattcggga aagacggtgg tgcgctcgtc   6300
gggcaccagg tgcacgcgcc aaccgcggtt gtgcaggta caaggtcaa cgctggtggc   6360 tacctctccg cgtaggcgct cgttggtcca gcagaggcgg ccgcccttgc gcgagcagaa   6420
tggcggtagg gggtctagct gcgtctcgtc cgggggtct gcgtccacgg taaagacccc   6480
gggcagcagg cgcgcgtcga agtagtctat cttgcatcct tgcaagtcta gcgcctgctg   6540
ccatgcgcgg gcgcaagcg cgcgctcgta tgggttgagt gggggacccc atggcatggg   6600
gtgggtgagc gcggaggcgt acatgccgca aatgtcgtaa acgtagaggg gctctctgag   6660
tattccaaga tatgtagggt agcatcttcc accgcggatg ctggcgcgca cgtaatcgta   6720
tagttcgtgc gagggagcga ggaggtcggg accgaggttg ctacgggcgg gctgctctgc   6780
```

| | |
|---|---|
| tcggaagact atctgcctga agatggcatg tgagttggat gatatggttg gacgctggaa | 6840 |
| gacgttgaag ctggcgtctg tgagacctac cgcgtcacgc acgaaggagg cgtaggagtc | 6900 |
| gcgcagcttg ttgaccagct cggcggtgac ctgcacgtct agggcgcagt agtccagggt | 6960 |
| ttccttgatg atgtcatact tatcctgtcc cttttttttc cacagctcgc ggttgaggac | 7020 |
| aaactcttcg cggtctttcc agtactcttg gatcggaaac ccgtcggcct ccgaacggta | 7080 |
| agagcctagc atgtagaact ggttgacggc ctggtaggcg cagcatccct tttctacggg | 7140 |
| tagcgcgtat gcctgcgcgg ccttccgagg cgaggtgtgg gtgagcgcaa aggtgtccct | 7200 |
| gaccatgact ttgaggtact ggtatttgaa gtcagtgtcg tcgcatccgc cctgctccca | 7260 |
| gagcaaaaag tccgtgcgct ttttggaacg cggatttggc agggcgaagg tgacatcgtt | 7320 |
| gaagagtatc tttcccgcgc gaggcataaa gttgcgtgtg atgcggaagg gtcccggcac | 7380 |
| ctcggaacgg ttgttaatta cctgggcggc gagcacgatc tcgtcaaagc cgttgatgtt | 7440 |
| gtggcccaca atgtaaagtt ccaagaagcg cgggatgccc ttgatggaag gcaattttt | 7500 |
| aagttcctcg taggtgagct cttcagggga gctgagcccg tgctctgaaa gggcccagtc | 7560 |
| tgcaagatga gggttggaag cgacgaatga gctccacagg tcacgggcca ttagcatttg | 7620 |
| caggtggtcg cgaaaggtcc taaactggcg acctatggcc atttttttctg gggtgatgca | 7680 |
| gtagaaggta agcgggtctt gttcccagcg gtcccatcca aggttcgcgg ctaggtctcg | 7740 |
| cgcggcagtc actagaggct catctccgcc gaacttcatg accagcatga agggcacgag | 7800 |
| ctgcttccca aaggccccca tccaagtata ggtctctaca tcgtaggtga caaagagacg | 7860 |
| ctcggtgcga ggatgcgagc cgatcgggaa gaactggatc tcccgccacc aattggagga | 7920 |
| gtggctattg atgtggtgaa agtagaagtc cctgcgacgg gccgaacact cgtgctggct | 7980 |
| tttgtaaaaa cgtgcgcagt actggcagcg gtgcacgggc tgtacatcct gcacgaggtt | 8040 |
| gacctgacga ccgcgcacaa ggaagcagag tgggaatttg agccctcgc ctggcgggtt | 8100 |
| tggctggtgg tcttctactt cggctgcttg tccttgaccg tctggctgct cgaggggagt | 8160 |
| tacggtggat cggaccacca cgccgcgcga gcccaaagtc cagatgtccg cgcgcggcgg | 8220 |
| tcggagcttg atgacaacat cgcgcagatg ggagctgtcc atggtctgga gctcccgcgg | 8280 |
| cgtcaggtca ggcgggagct cctgcaggtt tacctcgcat agacgggtca gggcgcgggc | 8340 |
| tagatccagg tgatacctaa tttccagggg ctggttggtg gcggcgtcga tggcttgcaa | 8400 |
| gaggccgcat ccccgcggcg cgactacggt accgcgcggc gggcggtggg ccgcggggt | 8460 |
| gtccttggat gatgcatcta aaagcggtga cgcgggcgag ccccggagg tagggggggc | 8520 |
| tccggacccg ccgggagagg gggcaggggc acgtcgcgc cgcgcgcggg caggagctgg | 8580 |
| tgctgcgcgc gtaggttgct ggcgaacgcg acgacgcggc ggttgatctc ctgaatctgg | 8640 |
| cgcctctgcg tgaagacgac gggcccgtg agcttgagcc tgaaagagag ttcgacagaa | 8700 |
| tcaatttcgg tgtcgttgac ggcggcctgg cgcaaaatct cctgcacgtc tcctgagttg | 8760 |
| tcttgatagg cgatctccgg catgaactgc tcgatctctt cctcctggag atctccgcgt | 8820 |
| ccggctcgct ccacggtggc ggcgaggtcg ttggaaatgc gggccatgag ctgcgagaag | 8880 |
| gcgttgaggc ctccctcgtt ccagacgcgg ctgtagacca cgcccccttc ggcatcgcgg | 8940 |
| gcgcgcatga ccacctgcgc gagattgagc tccacgtgcc gggcgaagac ggcgtagttt | 9000 |
| cgcaggcgct gaaagaggta gttgagggtg gtggcggtgt gttctgccac gaagaagtac | 9060 |
| ataacccagc gtcgcaacgt ggattcgttg atatccccca aggcctcaag gcgctccatg | 9120 |
| gcctcgtaga agtccacggc gaagttgaaa aactgggagt tgcgcgccga cacggttaac | 9180 |

-continued

```
tcctcctcca gaagacggat gagctcggcg acagtgtcgc gcacctcgcg ctcaaaggct      9240 acagggcct cttcttcttc ttcaatctcc tcttccataa gggcctcccc ttcttcttct       9300
tctggcggcg gtgggggagg ggggacacgg cggcgacgac ggcgcaccgg gaggcggtcg      9360
acaaagcgct cgatcatctc cccgcggcga cggcgcatgg tctcggtgac ggcgcggccg      9420
ttctcgcggg ggcgcagttg gaagacgccg cccgtcatgt cccggttatg ggttggcggg     9480
gggctgccat gcggcaggga tacggcgcta acgatgcatc tcaacaattg ttgtgtaggt      9540
actccgccgc cgagggacct gagcgagtcc gcatcgaccg gatcggaaaa cctctcgaga      9600
aaggcgtcta accagtcaca gtcgcaaggt aggctgagca ccgtggcggg cggcagcggg     9660
cggcggtcgg ggttgtttct ggcggaggtg ctgctgatga tgtaattaaa gtaggcggtc      9720
ttgagacggc ggatggtcga cagaagcacc atgtccttgg gtccggcctg ctgaatgcgc      9780
aggcggtcgg ccatgcccca ggcttcgttt tgacatcggc gcaggtcttt gtagtagtct      9840
tgcatgagcc tttctaccgg cacttcttct tctccttcct cttgtcctgc atctcttgca      9900
tctatcgctg cggcggcggc ggagtttggc cgtaggtggc gccctcttcc tcccatgcgt     9960
gtgaccccga agcccctcat cggctgaagc agggctaggt cggcgacaac gcgctcggct     10020
aatatggcct gctgcacctg cgtgagggta gactggaagt catccatgtc cacaaagcgg     10080
tggtatgcgc ccgtgttgat ggtgtaagtg cagttggcca taacggacca gttaacggtc     10140
tggtgacccg gctgcgagag ctcggtgtac ctgagacgcg agtaagccct cgagtcaaat     10200
acgtagtcgt tgcaagtccg caccaggtac tggtatccca ccaaaaagtg cggcggcggc     10260
tggcggtaga ggggccagcg tagggtggcc ggggctccgg gggcgagatc ttccaacata     10320
aggcgatgat atccgtagat gtacctggac atccaggtga tgccggcggc ggtggtggag     10380
gcgcgcggaa agtcgcggac gcggttccag atgttgcgca gcggcaaaaa gtgctccatg     10440
gtcgggacgc tctggccggt caggcgcgcg caatcgttga cgctctagcg tgcaaaagga     10500
gagcctgtaa gcgggcactc ttccgtggtc tggtggataa attcgcaagg gtatcatggc     10560
ggacgaccgg ggttcgagcc ccgtatccgg ccgtccgccg tgatccatgc ggttaccgcc     10620
cgcgtgtcga acccaggtgt gcgacgtcag acaacggggg agtgctcctt ttggcttcct     10680
tccaggcgcg gcggctgctg cgctagcttt tttggccact ggccgcgcgc agcgtaagcg     10740
gttaggctgg aaagcgaaag cattaagtgg ctcgctccct gtagccggag ggttatttc      10800 caagggttga gtcgcgggac ccccggttcg agtctcggac cggccggact gcggcgaacg     10860
ggggtttgcc tccccgtcat gcaagacccc gcttgcaaat tcctccggaa acagggacga     10920
gccccttttt tgcttttccc agatgcatcc ggtgctgcgg cagatgcgcc cccctcctca     10980
gcagcggcaa gagcaagagc agcggcagac atgcagggca ccctcccctc ctcctaccgc     11040
gtcaggaggg gcgacatccg cggttgacgc ggcagcagat ggtgattacg aaccccgcg      11100 gcgccgggcc cggcactacc tggacttgga ggagggcgag ggcctggcgc ggctaggagc     11160
gccctctcct gagcggtacc caaggtgca gctgaagcgt gatacgcgtg aggcgtacgt      11220
gccgcggcag aacctgtttc gcgaccgcga gggagaggag cccgaggaga tgcgggatcg     11280
aaagttccac gcagggcgcg agctgcggca tggcctgaat cgcgagcggt tgctgcgcga     11340
ggaggacttt gagcccgacg cgcgaaccgg gattagtccc gcgcgcgcac acgtggcggc     11400
cgccgacctg gtaaccgcat acgagcagac ggtgaaccag gagattaact ttcaaaaaag     11460
ctttaacaac cacgtgcgta cgcttgtggc gcgcgaggag gtggctatag gactgatgca     11520
```

-continued

```
tctgtgggac tttgtaagcg cgctggagca aaacccaaat agcaagccgc tcatggcgca   11580
gctgttcctt atagtgcagc acagcaggga caacgaggca ttcagggatg cgctgctaaa   11640
catagtagag cccgagggcc gctggctgct cgatttgata aacatcctgc agagcatagt   11700
ggtgcaggag cgcagcttga gcctggctga caaggtggcc gccatcaact attccatgct   11760
tagcctgggc aagttttacg cccgcaagat ataccatacc ccttacgttc ccatagacaa   11820
ggaggtaaag atcgaggggt tctacatgcg catggcgctg aaggtgctta ccttgagcga   11880
cgacctgggc gtttatcgca acgagcgcat ccacaaggcc gtgagcgtga gccggcggcg   11940
cgagctcagc gaccgcgagc tgatgcacag cctgcaaagg gccctggctg cacgggcag    12000 cggcgataga gaggccgagt cctactttga cgcgggcgct gacctgcgct gggccccaag   12060
ccgacgcgcc ctggaggcag ctggggccgg acctgggctg gcggtggcac ccgcgcgcgc   12120
tggcaacgtc ggcggcgtgg aggaatatga cgaggacgat gagtacgagc cagaggacgg   12180
cgagtactaa gcggtgatgt ttctgatcag atgatgcaag acgcaacgga cccggcggtg   12240
cgggcggcgc tgcagagcca gccgtccggc cttaactcca cggacgactg cgccaggtc    12300 atggaccgca tcatgtcgct gactgcgcgc aatcctgacg cgttccggca gcagccgcag   12360
gccaaccggc tctccgcaat tctggaagcg gtggtcccgg cgcgcgcaaa ccccacgcac   12420
gagaaggtgc tggcgatcgt aaacgcgctg ccgaaaaaca gggccatccg gcccgacgag   12480
gccggcctgg tctacgacgc gctgcttcag cgcgtggctc gttacaacag cggcaacgtg   12540
cagaccaacc tggaccggct ggtgggggat gtgcgcgagg ccgtggcgca gcgtgagcgc   12600
gcgcagcagc agggcaacct gggctccatg gttgcactaa acgccttcct gagtacacag   12660
cccgccaacg tgccgcgggg acaggaggac tacaccaact ttgtgagcgc actgcggcta   12720
atggtgactg agacaccgca aagtgaggtg taccagtctg ggccagacta ttttttccag   12780
accagtagac aaggcctgca gaccgtaaac ctgagccagg ctttcaaaaa cttgcagggg   12840
ctgtgggggg tgcgggctcc cacaggcgac cgcgcgaccg tgtctagctt gctgacgccc   12900
aactcgcgcc tgttgctgct gctaatagcg cccttcacgg acagtggcag cgtgtcccgg   12960
gacacatacc taggtcactt gctgacactg taccgcgagg ccataggtca ggcgcatgtg   13020
gacgagcata ctttccagga gattacaagt gtcagccgcg cgctggggca ggaggacacg   13080
ggcagcctgg aggcaaccct aaactacctg ctgaccaacc ggcggcagaa gatcccctcg   13140
ttgcacagtt taaacagcga ggaggagcgc attttgcgct acgtgcagca gagcgtgagc   13200
cttaacctga tgcgcgacgg ggtaacgccc agcgtggcgc tggacatgac cgcgcgcaac   13260
atggaaccgg gcatgtatgc ctcaaaccgg ccgtttatca accgcctaat ggactacttg   13320
catcgcgcgg ccgccgtgaa ccccgagtat ttcaccaatg ccatcttgaa cccgcactgg   13380
ctaccgcccc ctggtttcta caccggggga ttcgaggtgc ccgagggtaa cgatggattc   13440
ctctgggacg acatagacga cagcgtgttt tccccgcaac cgcagaccct gctagagttg   13500
caacagcgcg agcaggcaga ggcggcgctg cgaaaggaaa gcttccgcag gccaagcagc   13560
ttgtccgatc taggcgctgc ggccccgcgg tcagatgcta gtagcccatt tccaagcttg   13620
ataggtctct taccagcac tcgcaccacc cgcccgcgcc tgctgggcga ggaggagtac   13680
ctaaacaact cgctgctgca gccgcagcgc gaaaaaaacc tgcctccggc atttcccaac   13740
aacgggatag agagcctagt ggacaagatg agtagatgga agacgtacgc gcaggagcac   13800
agggacgtgc caggcccgcg cccgcccacc cgtcgtcaaa ggcacgaccg tcagcggggt   13860
ctggtgtggg aggacgatga ctcggcagac gacagcagcg tcctggattt gggagggagt   13920
```

```
ggcaacccgt tgcgcacct tcgccccagg ctggggagaa tgtttttaaaa aaaaaaaagc   13980 atgatgcaaa ataaaaaact caccaaggcc atggcaccga gcgttggttt tcttgtattc   14040
cccttagtat gcggcgcgcg gcgatgtatg aggaaggtcc tcctccctcc tacgagagtg   14100
tggtgagcgc ggcgccagtg gcggcggcgc tgggttctcc cttcgatgct cccctggacc   14160
cgccgtttgt gcctccgcgg tacctgcggc ctaccggggg gagaaacagc atccgttact   14220
ctgagttggc acccctattc gacaccaccc gtgtgtacct ggtggacaac aagtcaacgg   14280
atgtggcatc cctgaactac cagaacgacc acagcaactt tctgaccacg gtcattcaaa   14340
acaatgacta cagcccgggg gaggcaagca cacagaccat caatcttgac gaccggtcgc   14400 actgggcgg cgacctgaaa accatcctgc ataccaacat gccaaatgtg aacgagttca   14460
tgtttaccaa taagtttaag gcgcgggtga tggtgtcgcg cttgcctact aaggacaatc   14520
aggtggagct gaaatacgag tgggtggagt tcacgctgcc cgaggcaac tactccgaga   14580 ccatgaccat agaccttatg aacaacgcga tcgtggagca ctacttgaaa gtgggcagac   14640 agaacgggt tctggaaagc gacatcgggg taaagtttga caccccgcaac ttcagactgg   14700 ggtttgaccc cgtcactggt cttgtcatgc ctggggtata tacaaacgaa gccttccatc   14760
cagacatcat tttgctgcca ggatgcgggg tggacttcac ccacagccgc ctgagcaact   14820
tgttgggcat ccgcaagcgg caacccttcc aggagggctt taggatcacc tacgatgatc   14880
tggagggtgg taacattccc gcactgttgg atgtggacgc ctaccaggcg agcttgaaag   14940
atgacaccga acagggcggg ggtggcgcag gcggcagcaa cagcagtggc agcggcgcgg   15000
aagagaactc caacgcggca gccgcggcaa tgcagccggt ggaggacatg aacgatcatg   15060
ccattcgcgg cgacaccttt gccacacggg ctgaggagaa gcgcgctgag gccgaagcag   15120
cggccgaagc tgccgcccc gctgcgcaac ccgaggtcga gaagcctcag aagaaaccgg   15180
tgatcaaacc cctgacagag gacagcaaga acgcagtta caacctaata agcaatgaca   15240
gcaccttcac ccagtaccgc agctggtacc ttgcatacaa ctacggcgac cctcagaccg   15300
gaatccgctc atggacctg ctttgcactc ctgacgtaac ctgcggctcg gagcaggtct   15360
actggtcgtt gccagacatg atgcaagacc ccgtgacctt ccgctccacg cgccagatca   15420
gcaactttcc ggtggtgggc gccgagctgt tgcccgtgca ctccaagagc ttctacaacg   15480
accaggccgt ctactcccaa ctcatccgcc agtttacctc tctgacccac gtgttcaatc   15540
gctttcccga gaaccagatt ttggcgcgcc cgccagcccc caccatcacc accgtcagtg   15600
aaaacgttcc tgctctcaca gatcacggga cgctaccgct gcgcaacagc atcggaggag   15660
tccagcgagt gaccattact gacgccagac gccgcacctg cccctacgtt tacaaggccc   15720
tgggcatagt ctcgccgcgc gtcctatcga gccgcacttt ttgagcaagc atgtccatcc   15780
ttatatcgcc cagcaataac acaggctggg gcctgcgctt cccaagcaag atgtttggcg   15840
gggccaagaa gcgctccgac caacacccag tgcgcgtgcg cgggcactac cgcgcgccct   15900
ggggcgcgca caaacgcggc cgcactgggc gcaccaccgt cgatgacgcc atcgacgcg   15960 tggtggagga ggcgcgcaac tacacgccca cgccgccacc agtgtccaca gtggacgcgg   16020
ccattcagac cgtggtgcgc ggagcccggc gctatgctaa aatgaagaga cggcggaggc   16080
gcgtagcacg tcgccaccgc cgccgacccg gcactgccgc caacgcgcg cggcggccc   16140 tgcttaaccg cgcacgtcgc accggccgac gggcggccat gcgggccgct cgaaggctgg   16200
ccgcgggtat tgtcactgtg ccccccaggt ccaggcgacg agcggccgcc gcagcagccg   16260
```

-continued

```
cggccattag tgctatgact cagggtcgca ggggcaacgt gtattgggtg cgcgactcgg    16320
ttagcggcct gcgcgtgccc gtgcgcaccc gcccccgcg caactagatt gcaagaaaaa    16380
actacttaga ctcgtactgt tgtatgtatc cagcggcggc ggcgcgcaac gaagctatgt    16440
ccaagcgcaa aatcaaagaa gagatgctcc aggtcatcgc gccggagatc tatggccccc    16500
cgaagaagga agagcaggat tacaagcccc gaaagctaaa gcgggtcaaa agaaaaaga    16560 aagatgatga tgatgaactt gacgacgagg tggaactgct gcacgctacc gcgcccaggc    16620
gacgggtaca gtggaaaggt cgacgcgtaa aacgtgtttt gcgacccggc accaccgtag    16680
tctttacgcc cggtgagcgc tccacccgca cctacaagcg cgtgtatgat gaggtgtacg    16740
gcgacgagga cctgcttgag caggccaacg agcgcctcgg ggagtttgcc tacgaaaagc    16800
ggcataagga catgctggcg ttgccgctgg acgagggcaa cccaacacct agcctaaagc    16860
ccgtaacact gcagcaggtg ctgcccgcgc ttgcaccgtc cgaagaaaag cgcggcctaa    16920
agcgcgagtc tggtgacttg gcacccaccg tgcagctgat ggtacccaag cgccagcgac    16980
tggaagatgt cttggaaaaa atgaccgtgg aacctgggct ggagcccgag gtccgcgtgc    17040
ggccaatcaa gcaggtggcg ccgggactgg gcgtgcagac cgtggacgtt cagataccca    17100
ctaccagtag caccagtatt gccaccgcca cagagggcat ggagacacaa acgtccccgg    17160
ttgcctcagc ggtggcggat gccgcggtgc aggcggtcgc tgcggccgcg tccaagacct    17220
ctacggaggt gcaaacggac ccgtggatgt ttcgcgtttc agccccccgg cgcccgcgcg    17280
gttcgaggaa gtacggcgcc gccagcgcgc tactgcccga atatgcccta catccttcca    17340
ttgcgcctac ccccggctat cgtggctaca cctaccgccc cagaagacga gcaactaccc    17400
gacgccgaac caccactgga acccgccgcc gccgtcgccc tcgccagccc gtgctggccc    17460
cgatttccgt gcgcagggtg gctcgcgaag gaggcaggac cctggtgctg ccaacagcgc    17520
gctaccaccc cagcatcgtt taaaagccgg tctttgtggt tcttgcagat atggccctca    17580
cctgccgcct ccgtttcccg gtgccgggat tccgaggaag aatgcaccgt aggaggggca    17640
tggccggcca cggcctgacg ggcggcatgc gtcgtgcgca ccaccggcgg cggcgcgcgt    17700
cgcaccgtcg catgcgcggc ggtatcctgc ccctccttat tccactgatc gccgcggcga    17760
ttggcgccgt gccggaatt gcatccgtgg ccttgcaggc gcagagacac tgattaaaaa    17820
caagttgcat gtggaaaaat caaaataaaa agtctggact ctcacgctcg cttggtcctg    17880 taactattt gtagaatgga agacatcaac tttgcgtctc tggccccgcg cacggctcg    17940 cgcccgttca tgggaaactg gcaagatatc ggcaccagca atatgagcgg tggcgccttc    18000
agctggggct cgctgtggag cggcattaaa aatttcggtt ccaccgttaa gaactatggc    18060
agcaaggcct ggaacagcag cacaggccag atgctgaggg ataagttgaa agagcaaaat    18120
ttccaacaaa aggtggtaga tggcctggcc tctggcatta gcggggtggt ggacctggcc    18180
aaccaggcag tgcaaaataa gattaacagt aagcttgatc cccgccctcc cgtagaggag    18240
cctccaccgg ccgtggagac agtgtctcca gaggggcgtg gcgaaaagcg tccgcgcccc    18300
gacagggaag aaactctggt gacgcaaata gacgagcctc cctcgtacga ggaggcacta    18360
aagcaaggcc tgcccaccac ccgtccaatc gcgcccatgg ctaccggagt gctgggccag    18420
cacacacccg taacgctgga cctgcctccc cccgccgaca cccagcagaa acctgtgctg    18480
ccaggcccga ccgccgttgt tgtaacccgt cctagccgcg cgtccctgcg ccgcgccgcc    18540
agcggtccgc gatcgttgcg gcccgtagcc agtggcaact ggcaaagcac actgaacagc    18600
atcgtgggtc tgggggtgca atccctgaag cgccgacgat gcttctgaat agctaacgtg    18660
```

```
tcgtatgtgt gtcatgtatg cgtccatgtc gccgccagag gagctgctga gccgccgcgc    18720
gcccgctttc caagatggct accccttcga tgatgccgca gtggtcttac atgcacatct    18780
cgggccagga cgcctcggag tacctgagcc ccgggctggt gcagtttgcc cgcgccaccg    18840
agacgtactt cagcctgaat aacaagttta gaaaccccac ggtggcgcct acgcacgacg    18900
tgaccacaga ccggtcccag cgtttgacgc tgcggttcat ccctgtggac cgtgaggata    18960
ctgcgtactc gtacaaggcg cggttcaccc tagctgtggg tgataaccgt gtgctggaca    19020
tggcttccac gtactttgac atccgcgcg tgctggacag gggccctact tttaagccct    19080
actctggcac tgcctacaac gccctggctc ccaagggtgc cccaaatcct tgcgaatggg    19140
atgaagctgc tactgctctt gaaataaacc tagaagaaga ggacgatgac aacgaagacg    19200
aagtagacga gcaagctgag cagcaaaaaa ctcacgtatt tgggcaggcg ccttattctg    19260
gtataaatat tacaaaggag ggtattcaaa taggtgtcga aggtcaaaca cctaaatatg    19320
ccgataaaac atttcaacct gaacctcaaa taggagaatc tcagtggtac gaaactgaaa    19380
ttaatcatgc agctgggaga gtccttaaaa agactacccc aatgaaacca tgttacggtt    19440
catatgcaaa acccacaaat gaaaatggag ggcaaggcat tcttgtaaag caacaaaatg    19500
gaaagctaga aagtcaagtg gaaatgcaat ttttctcaac tactgaggcg accgcaggca    19560
atggtgataa cttgactcct aaagtggtat tgtacagtga agatgtagat atagaaaccc    19620
cagacactca tatttcttac atgcccacta ttaaggaagg taactcacga gaactaatgg    19680
gccaacaatc tatgcccaac aggcctaatt acattgcttt tagggacaat tttattggtc    19740
taatgtatta caacagcacg ggtaatatgg gtgttctggc gggccaagca tcgcagttga    19800
atgctgttgt agatttgcaa gacagaaaca cagagctttc ataccagctt ttgcttgatt    19860
ccattggtga tagaaccagg tacttttcta tgtggaatca ggctgttgac agctatgatc    19920
cagatgttag aattattgaa atcatggaa ctgaagatga acttccaaat tactgctttc    19980
cactgggagg tgtgattaat acagagactc ttaccaaggt aaaacctaaa acaggtcagg    20040
aaaatggatg ggaaaaagat gctacagaat tttcagataa aaatgaaata agagttggaa    20100
ataattttgc catggaaatc aatctaaatg ccaacctgtg gagaaatttc ctgtactcca    20160
acatagcgct gtatttgccc gacaagctaa agtacagtcc ttccaacgta aaaatttctg    20220
ataacccaaa cacctacgac tacatgaaca agcgagtggt ggctcccggg ttagtggact    20280
gctacattaa ccttggagca cgctggtccc ttgactatat ggacaacgtc aacccattta    20340
accaccaccg caatgctggc ctgcgctacc gctcaatgtt gctgggcaat ggtcgctatg    20400
tgcccttcca catccaggtg cctcagaagt tctttgccat taaaaacctc cttctcctgc    20460
cgggctcata cacctacgag tggaacttca ggaaggatgt taacatggtt ctgcagagct    20520
ccctaggaaa tgacctaagg gttgacggag ccagcattaa gtttgatagc atttgccttt    20580
acgccacctt cttccccatg gcccacaaca ccgcctccac gcttgaggcc atgcttagaa    20640
acgacaccaa cgaccagtcc tttaacgact atctctccgc cgccaacatg ctctaccctt    20700
tacccgccaa cgctaccaac gtgcccatat ccatcccctc ccgcaactgg gcggctttcc    20760
gcggctgggc cttcacgcgc cttaagacta aggaaacccc atcactgggc tcgggctacg    20820
acccttatta cacctactct ggctctatac cctacctaga tggaaccttt tacctcaacc    20880
acacctttaa gaaggtggcc attacctttg actcttctgt cagctggcct ggcaatgacc    20940
gcctgcttac ccccaacgag tttgaaatta gcgctcagt tgacggggag ggttacaacg    21000
```

-continued

```
ttgcccagtg taacatgacc aaagactggt tcctggtaca aatgctagct aactacaaca   21060
ttggctacca gggcttctat atcccagaga gctacaagga ccgcatgtac tccttcttta   21120
gaaacttcca gcccatgagc cgtcaggtgg tggatgatac taaatacaag gactaccaac   21180
aggtgggcat cctacaccaa cacaacaact ctggatttgt tggctacctt gcccccacca   21240
tgcgcgaagg acaggcctac cctgctaact tcccctatcc gcttataggc aagaccgcag   21300
ttgacagcat tacccagaaa aagtttcttt gcgatcgcac cctttggcgc atcccattct   21360
ccagtaactt tatgtccatg ggcgcactca cagacctggg ccaaaacctt ctctacgcca   21420
actccgccca cgcgctagac atgacttttg aggtggatcc catggacgag cccacccttc   21480
tttatgtttt gtttgaagtc tttgacgtgg tccgtgtgca ccggccgcac cgcggcgtca   21540
tcgaaaccgt gtacctgcgc acgcccttct cggccggcaa cgccacaaca taaagaagca   21600
agcaacatca acaacagctg ccgccatggg ctccagtgag caggaactga agccattgt   21660
caaagatctt ggttgtgggc catatttttt gggcacctat gacaagcgct ttccaggctt   21720
tgtttctcca cacaagctcg cctgcgccat agtcaatacg gccggtcgcg agactggggg   21780
cgtacactgg atggcctttg cctggaaccc gcactcaaaa acatgctacc tctttgagcc   21840
ctttggcttt tctgaccagc gactcaagca ggtttaccag tttgagtacg agtcactcct   21900
gcgccgtagc gccattgctt cttcccccga ccgctgtata acgctggaaa agtccaccca   21960
aagcgtacag gggcccaact cggccgcctg tggactattc tgctgcatgt ttctccacgc   22020
cttttgccaac tggccccaaa ctcccatgga tcacaaccccс accatgaacc ttattaccgg   22080
ggtacccaac tccatgctca acagtcccca ggtacagccc accctgcgtc gcaaccagga   22140
acagctctac agcttcctgg agcgccactc gccctacttc cgcagccaca gtgcgcagat   22200
taggagcgcc acttcttttt gtcacttgaa aaacatgtaa aaataatgta ctagagacac   22260
tttcaataaa ggcaaatgct tttatttgta cactctcggg tgattattta cccccaccct   22320
tgccgtctgc gccgtttaaa aatcaaaggg gttctgccgc gcatcgctat gcgccactgg   22380
cagggacacg ttgcgatact ggtgtttagt gctccactta aactcaggca caaccatccg   22440
cggcagctcg gtgaagtttt cactccacag gctgcgcacc atcaccaacg cgtttagcag   22500
gtcgggcgcc gatatcttga agtcgcagtt ggggcctccg ccctgcgcgc gcgagttgcg   22560
atacacaggg ttgcagcact ggaacactat cagcgccggg tggtgcacgc tggccagcac   22620
gctcttgtcg gagatcagat ccgcgtccag gtcctccgcg ttgctcaggg cgaacggagt   22680
caactttggt agctgccttc ccaaaaaggg cgcgtgccca ggctttgagt tgcactcgca   22740
ccgtagtggc atcaaaaggt gaccgtgccc ggtctgggcg ttaggataca gcgcctgcat   22800
aaaagccttg atctgcttaa aagccacctg agcctttgcg ccttcagaga gaacatgcc   22860
gcaagacttg ccggaaaact gattggccgg acaggccgcg tcgtgcacgc agcaccttgc   22920
gtcggtgttg gagatctgca ccacatttcg gccccaccgg ttcttcacga tcttggcctt   22980
gctagactgc tccttcagcg cgcgctgccc gttttcgctc gtcacatcca tttcaatcac   23040
gtgctcctta tttatcataa tgcttccgtg tagacactta agctcgcctt cgatctcagc   23100
gcagcggtgc agccacaacg cgcagcccgt gggctcgtga tgcttgtagg tcacctctgc   23160
aaacgactgc aggtacgcct gcaggaatcg ccccatcatc gtcacaaagg tcttgttgct   23220
ggtgaaggtc agctgcaacc cgcggtgctc ctcgttcagc caggtcttgc atacggccgc   23280
cagagcttcc acttggtcag gcagtagttt gaagttcgcc tttagatcgt tatccacgtg   23340
gtacttgtcc atcagcgcgc gcgcagcctc catgcccttc tcccacgcag acacgatcgg   23400
```

```
cacactcagc gggttcatca ccgtaatttc actttccgct tcgctgggct cttcctcttc   23460
ctcttgcgtc cgcataccac gcgccactgg gtcgtcttca ttcagccgcc gcactgtgcg   23520
cttacctcct ttgccatgct tgattagcac cggtgggttg ctgaaaccca ccatttgtag   23580
cgccacatct tctctttctt cctcgctgtc cacgattacc tctggtgatg gcgggcgctc   23640
gggcttggga aagggcgct tcttttttctt cttgggcgca atggccaaat ccgccgccga   23700
ggtcgatggc cgcgggctgg gtgtgcgcgg caccagcgcg tcttgtgatg agtcttcctc   23760
gtcctcggac tcgatacgcc gcctcatccg cttttttggg ggcgcccggg gaggcggcgg   23820
cgacggggac ggggacgaca cgtcctccat ggttggggga cgtcgcgccg caccgcgtcc   23880
gcgctcgggg gtggtttcgc gctgctcctc ttcccgactg gccatttcct tctcctatag   23940
gcagaaaaag atcatggagt cagtcgagaa gaaggacagc ctaaccgccc cctctgagtt   24000
cgccaccacc gcctccaccg atgccgccaa cgcgcctacc accttccccg tcgaggcacc   24060
cccgcttgag gaggaggaag tgattatcga gcaggaccca ggttttgtaa gcgaagacga   24120
cgaggaccgc tcagtaccaa cagaggataa aaagcaagac caggacaacg cagaggcaaa   24180
cgaggaacaa gtcgggcggg gggacgaaag gcatggcgac tacctagatg tgggagacga   24240
cgtgctgttg aagcatctgc agcgccagtg cgccattatc tgcgacgcgt tgcaagagcg   24300
cagcgatgtg cccctcgcca tagcggatgt cagccttgcc tacgaacgcc acctattctc   24360
accgcgcgta ccccccaaac gccaagaaaa cggcacatgc gagcccaacc cgcgcctcaa   24420
cttctacccc gtatttgccg tgccagaggt gcttgccacc tatcacatct ttttccaaaa   24480
ctgcaagata cccctatcct gccgtgccaa ccgcagccga gcgacaagc agctggcctt   24540
gcggcagggc gctgtcatac ctgatatcgc ctcgctcaac gaagtgccaa aaatctttga   24600
gggtcttgga cgcgacgaga agcgcgcggc aaacgctctg caacaggaaa acagcgaaaa   24660
tgaaagtcac tctggagtgt tggtggaact cgagggtgac aacgcgcgcc tagccgtact   24720
aaaacgcagc atcgaggtca cccactttgc ctacccggca cttaacctac ccccaaggt   24780
catgagcaca gtcatgagtg agctgatcgt gcgccgtgcg cagcccctgg agagggatgc   24840
aaatttgcaa gaacaaacag aggagggcct acccgcagtt ggcgacgagc agctagcgcg   24900
ctggcttcaa acgcgcgagc ctgccgactt ggaggagcga cgcaaactaa tgatggccgc   24960
agtgctcgtt accgtggagc ttgagtgcat gcagcggttc tttgctgacc cggagatgca   25020
gcgcaagcta gaggaaacat tgcactacac ctttcgacag ggctacgtac gccaggcctg   25080
caagatctcc aacgtggagc tctgcaacct ggtctcctac cttggaattt tgcacgaaaa   25140
ccgcctttggg caaaacgtgc ttcattccac gctcaagggc gaggcgcgcc gcgactacgt   25200
ccgcgactgc gtttacttat ttctatgcta cacctggcag acggccatgg gcgtttggca   25260
gcagtgcttg gaggagtgca acctcaagga gctgcagaaa ctgctaaagc aaaacttgaa   25320
ggacctatgg acggccttca acagcgcgctc cgtggccgcg cacctggcgg acatcatttt   25380
ccccgaacgc ctgcttaaaa ccctgcaaca gggtctgcca gacttcacca gtcaaagcat   25440
gttgcagaac tttaggaact ttatcctaga gcgctcagga atcttgcccg ccacctgctg   25500
tgcacttcct agcgactttg tgcccattaa gtaccgcgaa tgccctccgc cgctttgggg   25560
ccactgctac cttctgcagc tagccaacta ccttgcctac cactctgaca taatggaaga   25620
cgtgagcggt gacggtctac tggagtgtca ctgtcgctgc aacctatgca cccgcaccg   25680
ctccctggtt tgcaattcgc agctgcttaa cgaaagtcaa attatcggta cctttgagct   25740
```

```
gcagggtccc tcgcctgacg aaaagtccgc ggctccgggg ttgaaactca ctccggggct  25800
gtggacgtcg gcttaccttc gcaaatttgt acctgaggac taccacgccc acgagattag  25860
gttctacgaa gaccaatccc gcccgccaaa tgcggagctt accgcctgcg tcattaccca  25920
gggccacatt cttggccaat tgcaagccat caacaaagcc cgccaagagt ttctgctacg  25980
aaagggacgg ggggtttact tggaccccca gtccggcgag gagctcaacc caatccccc   26040
gccgccgcag ccctatcagc agcagccgcg ggcccttgct tcccaggatg gcacccaaaa  26100
agaagctgca gctgccgccg ccacccacgg acgaggagga atactgggac agtcaggcag  26160
aggaggtttt ggacgaggag gaggaggaca tgatggaaga ctgggagagc ctagacgagg  26220
aagcttccga ggtcgaagag gtgtcagacg aaacaccgtc ccctcggtc gcattcccct   26280
cgccggcgcc ccagaaatcg gcaaccggtt ccagcatggc tacaacctcc gctcctcagg  26340
cgccgccggc actgcccgtt cgccgaccca accgtagatg ggacaccact ggaaccaggg  26400
ccggtaagtc caagcagccg ccgccgttag cccaagagca caacagcgc caaggctacc   26460
gctcatggcg cgggcacaag aacgccatag ttgcttgctt gcaagactgt ggggcaaca   26520
tctccttcgc ccgccgcttt cttctctacc atcacggcgt ggccttcccc cgtaacatcc  26580
tgcattacta ccgtcatctc tacagcccat actgcaccgg cggcagcggc agcggcagca  26640
acagcagcgg ccacacagaa gcaaaggcga ccggatagca agactctgac aaagcccaag  26700
aaatccacag cggcggcagc agcaggagga ggagcgctgc gtctggcgcc caacgaaccc  26760
gtatcgaccc gcgagcttag aaacaggatt tttcccactc tgtatgctat atttcaacag  26820
agcaggggcc aagaacaaga gctgaaaata aaaaacaggt ctctgcgatc cctcacccgc  26880
agctgcctgt atcacaaaag cgaagatcag cttcggcgca cgctgaaaga cgcggaggct  26940
ctcttcagta aatactgcgc gctgactctt aaggactagt ttcgcgccct ttctcaaatt  27000
taagcgcgaa aactacgtca tctccagcgg ccacacccgg cgccagcacc tgtcgtcagc  27060
gccattatga gcaaggaaat tcccacgccc tacatgtgga gttaccagcc acaaatggga  27120
cttgcggctg gagctgccca agactactca acccgaataa actacatgag cgcgggaccc  27180
cacatgatat cccgggtcaa cggaatccgc gcccaccgaa accgaattct cttggaacag  27240
gcggctatta ccaccacacc tcgtaataac cttaatcccc gtagttggcc cgctgccctg  27300
gtgtaccagg aaagtcccgc tcccaccact gtggtacttc ccagagacgc ccaggccgaa  27360
gttcagatga ctaactcagg ggcgcagctt gcgggcggct ttcgtcacag ggtgcggtcg  27420
cccgggcagg gtataactca cctgacaatc agagggcgag gtattcagct caacgacgag  27480
tcggtgagct cctcgcttgg tctccgtccg gacgggacat tcagatcgg cggcgccggc   27540
cgtccttcat tcacgcctcg tcaggcaatc ctaactctgc agacctcgtc tctgagccg   27600
cgctctggag gcattggaac tctgcaattt attgaggagt ttgtgccatc ggtctacttt  27660
aaccccttct cgggacctcc cggccactat ccggatcaat ttattcctaa ctttgacgcg  27720
gtaaaggact cggcggacgg ctacgactga atgttaagtg gagaggcaga gcaactgcgc  27780
ctgaaacacc tggtccactg tcgccgccac aagtgctttg cccgcgactc cggtgagttt  27840
tgctactttg aattgcccga ggatcatatc gagggcccgg cgcacggcgt ccggcttacc  27900
gcccagggag agcttgcccg tagcctgatt cgggagttta cccagcgccc cctgctagtt  27960
gagcgggaca ggggaccctg tgttctcact gtgatttgca actgtcctaa ccttggatta  28020
catcaagatc tttgttgcca tctctgtgct gagtataata aatacagaaa ttaaaatata  28080
ctggggctcc tatcgccatc ctgtaaacgc caccgtcttc acccgcccaa gcaaaccaag  28140
```

```
gcgaacctta cctggtactt ttaacatctc tccctctgtg atttacaaca gtttcaaccc   28200
agacggagtg agtctacgag agaacctctc cgagctcagc tactccatca gaaaaaacac   28260
caccctcctt acctgccggg aacgtacgag tgcgtcaccg gccgctgcac cacacctacc   28320
gcctgaccgt aaaccagact ttttccggac agacctcaat aactctgttt accagaacag   28380
gaggtgagct tagaaaaccc ttagggtatt aggccaaagg cgcagctact gtggggttta   28440
tgaacaattc aagcaactct acgggctatt ctaattcagg tttctctaga agtcaggctt   28500
cctggatgtc agcatctgac tttggccagc acctgtcccg cggatttgtt ccagtccaac   28560
tacagcgacc caccctaaca gagatgacca acacaaccaa cgcggccgcc gctaccggac   28620
ttacatctac cacaaataca ccccaagttt ctgcctttgt caataactgg gataacttgg   28680
gcatgtggtg gttctccata gcgcttatgt ttgtatgcct tattattatg tggctcatct   28740
gctgcctaaa gcgcaaacgc gcccgaccac ccatctatag tcccatcatt gtgctacacc   28800
caaacaatga tggaatccat agattggacg gactgaaaca catgttcttt tctcttacag   28860
tatgattaaa tgagatctag aaatggacgg aattattaca gagcagcgcc tgctagaaag   28920
acgcagggca gcggccgagc aacagcgcat gaatcaagag ctccaagaca tggttaactt   28980
gcaccagtgc aaaaggggta tcttttgtct ggtaaagcag gccaaagtca cctacgacag   29040
taataccacc ggacaccgcc ttagctacaa gttgccaacc aagcgtcaga aattggtggt   29100
catggtggga gaaaagccca ttaccataac tcagcactcg gtagaaaccg aaggctgcat   29160
tcactcacct tgtcaaggac ctgaggatct ctgcacccct attaagaccc tgtgcggtct   29220
caaagatctt attcccttta actaataaaa aaaataata aagcatcact tacttaaaat   29280
cagttagcaa atttctgtcc agtttattca gcagcacctc cttgccctcc tcccagctct   29340
ggtattgcag cttcctcctg gctgcaaaact ttctccacaa tctaaatgga atgtcagttt   29400
cctcctgttc ctgtccatcc gcacccacta tcttcatgtt gttgcagatg aagcgcgcaa   29460
gaccgtctga agataccttc aaccccgtgt atccatatga cacggaaacc ggtcctccaa   29520
ctgtgccttt tcttactcct cccttttgtat cccccaatgg gtttcaagag agtccccctg   29580
gggtactctc tttgcgccta tccgaaccte tagttacctc caatggcatg cttgcgctca   29640
aaatgggcaa cggcctctct ctggacgagg ccggcaacct tacctcccaa aatgtaacca   29700
ctgtgagccc acctctcaaa aaaccaagt caaacataaa cctggaaata tctgcacccc   29760
tcacagttac ctcagaagcc ctaactgtgg ctgccgccgc acctctaatg gtcgcgggca   29820
acacactcac catgcaatca caggccccgc taaccgtgca cgactccaaa cttagcattg   29880
ccacccaagg acccctcaca gtgtcagaag gaaagctagc cctgcaaaca tcaggccccc   29940
tcaccaccac cgatagcagt acccttacta tcactgcctc acccccctcta actactgcca   30000 ctggtagctt gggcattgac ttgaaagagc ccatttatac acaaaatgga aaactaggac   30060
taaagtacgg ggctcctttg catgtaacag acgacctaaa cactttgacc gtagcaactg   30120
gtccaggtgt gactattaat aatacttcct tgcaaactaa agttactgga gccttgggtt   30180
ttgattcaca aggcaatatg caacttaatg tagcaggagg actaaggatt gattctcaaa   30240
acagacgcct tatacttgat gttagttatc cgtttgatgc tcaaaaccaa ctaaatctaa   30300
gactaggaca gggccctctt tttataaact cagcccacaa cttggatatt aactacaaca   30360
aaggccttta cttgtttaca gcttcaaaca attccaaaaa gcttgaggtt aacctaagca   30420
ctgccaaggg gttgatgttt gacgctacag ccatagccat taatgcagga gatgggcttg   30480
```

-continued

```
aatttggttc acctaatgca ccaaacacaa atcccctcaa aacaaaaatt ggccatggcc      30540
tagaatttga ttcaaacaag gctatggttc ctaaactagg aactggcctt agttttgaca      30600
gcacaggtgc cattacagta ggaaacaaaa ataatgataa gctaactttg tggaccacac      30660
cagctccatc tcctaactgt agactaaatg cagagaaaga tgctaaactc actttggtct      30720
taacaaaatg tggcagtcaa atacttgcta cagtttcagt tttggctgtt aaaggcagtt      30780
tggctccaat atctggaaca gttcaaagtg ctcatcttat tataagattt gacgaaaatg      30840
gagtgctact aaacaattcc ttcctggacc cagaatattg aactttaga aatggagatc       30900
ttactgaagg cacagcctat acaaacgctg ttggatttat gcctaaccta tcagcttatc      30960
caaaatctca cggtaaaact gccaaaagta acattgtcag tcaagtttac ttaaacggag      31020
acaaaactaa acctgtaaca ctaaccatta cactaaacgg tacacaggaa acaggagaca      31080
caactccaag tgcatactct atgtcatttt catgggactg gtctggccac aactacatta      31140
atgaaatatt tgccacatcc tcttacactt tttcatacat tgcccaagaa taaagaatcg      31200
tttgtgttat gtttcaacgt gtttattttt caattgcaga aaatttcaag tcatttttca      31260
ttcagtagta tagccccacc accacatagc ttatacagat caccgtacct taatcaaact      31320
cacagaaccc tagtattcaa cctgccacct ccctcccaac acacagagta cacagtcctt      31380
tctccccggc tggccttaaa aagcatcata tcatgggtaa cagacatatt cttaggtgtt      31440
atattccaca cggtttcctg tcgagccaaa cgctcatcag tgatattaat aaactccccg      31500
ggcagctcac ttaagttcat gtcgctgtcc agctgctgag ccacaggctg ctgtccaact      31560
tgcggttgct taacgggcgg cgaaggagaa gtccacgcct acatgggggt agagtcataa      31620
tcgtgcatca ggatagggcg gtggtgctgc agcagcgcgc gaataaactg ctgccgccgc      31680
cgctccgtcc tgcaggaata caacatggca gtggtctcct cagcgatgat tcgcaccgcc      31740
cgcagcataa ggcgccttgt cctccgggca cagcagcgca ccctgatctc acttaaatca      31800
gcacagtaac tgcagcacag caccacaata ttgttcaaaa tcccacagtg caaggcgctg      31860
tatccaaagc tcatggcggg gaccacagaa cccacgtggc catcatacca caagcgcagg      31920
tagattaagt ggcgacccct cataaacacg ctggacataa acattacctc ttttggcatg      31980
ttgtaattca ccacctcccg gtaccatata aacctctgat taaacatggc gccatccacc      32040
accatcctaa accagctggc caaaacctgc ccgccggcta tacactgcag ggaaccggga      32100
ctggaacaat gacagtggag agcccaggac tcgtaaccat ggatcatcat gctcgtcatg      32160
atatcaatgt tggcacaaca caggcacacg tgcatacact tcctcaggat tacaagctcc      32220
tcccgcgtta gaaccatatc ccagggaaca acccattcct gaatcagcgt aaatcccaca      32280
ctgcagggaa gacctcgcac gtaactcacg ttgtgcattg tcaaagtgtt acattcgggc      32340
agcagcggat gatcctccag tatggtagcg cgggtttctg tctcaaaagg aggtagacga      32400
tccctactgt acggagtgcg ccgagacaac cgagatcgtg ttggtcgtag tgtcatgcca      32460
aatggaacgc cggacgtagt catatttcct gaagcaaaac caggtgcggg cgtgacaaac      32520
agatctgcgt ctccggtctc gccgcttaga tcgctctgtg tagtagttgt agtatatcca      32580
ctctctcaaa gcatccaggc gcccctggcc ttcgggttct atgtaaactc cttcatgcgc      32640
cgctgccctg ataacatcca ccaccgcaga ataagccaca cccagccaac ctacacattc      32700
gttctgcgag tcacacacgg gaggagcggg aagagctgga agaaccatgt ttttttttt       32760
attccaaaag attatccaaa acctcaaaat gaagatctat taagtgaacg cgctcccctc      32820
cggtggcgtg gtcaaactct acagccaaag aacagataat ggcatttgta agatgttgca     32880
```

```
caatggcttc caaaaggcaa acggccctca cgtccaagtg gacgtaaagg ctaaacccct  32940
cagggtgaat ctcctctata aacattccag caccttcaac catgcccaaa taattctcat  33000
ctcgccacct tctcaatata tctctaagca aatcccgaat attaagtccg gccattgtaa  33060
aaatctgctc cagagcgccc tccaccttca gcctcaagca gcgaatcatg attgcaaaaa  33120
ttcaggttcc tcacagacct gtataagatt caaaagcgga acattaacaa aaataccgcg  33180
atcccgtagg tcccttcgca gggccagctg aacataatcg tgcaggtctg cacggaccag  33240
cgcggccact tccccgccag gaaccttgac aaaagaaccc acactgatta tgacacgcat  33300
actcggagct atgctaacca gcgtagcccc gatgtaagct tgttgcatg ggcggcgata  33360
taaaatgcaa ggtgctgctc aaaaaatcag gcaaagcctc gcgcaaaaaa gaaagcacat  33420
cgtagtcatg ctcatgcaga taaggcagg taagctccgg aaccaccaca gaaaaagaca  33480
ccattttct ctcaaacatg tctgcgggtt tctgcataaa cacaaaataa aataacaaaa  33540
aaacatttaa acattagaag cctgtcttac aacaggaaaa acaacccctta taagcataag  33600
acggactacg gccatgccgg cgtgaccgta aaaaaactgg tcaccgtgat taaaaagcac  33660
caccgacagc tcctcggtca tgtccggagt cataatgtaa gactcggtaa acacatcagg  33720
ttgattcatc ggtcagtgct aaaaagcgac cgaaatagcc cggggaata catacccgca  33780
ggcgtagaga caacattaca gcccccatag gaggtataac aaaattaata ggagagaaaa  33840
acacataaac acctgaaaaa ccctcctgcc taggcaaaat agcaccctcc cgctccagaa  33900
caacatacag cgcttcacag cggcagccta acagtcagcc ttaccagtaa aaagaaaac  33960
ctattaaaaa aacaccactc gacacggcac cagctcaatc agtcacagtg taaaaaaggg  34020
ccaagtgcag taatcagcgc tgcctgaaac tcgcgccgcg aggagagggc ggggccgcgg  34080
aaaggaaggg gaggggctgg gagggcccg aggggctgg gccggggacc cgggaggggt  34140
cgggacgggg cgggtccgc gcggaggagg cggagctgga aggtgaaggg gcaggacggg  34200
tgcccgggtc cccagtccct ccgccacgtg ggaagcgcgg tcctgggcgt ctgtgcccgc  34260
gaatccactg ggagcccggc ctggccccga cagcgcagct gctccgggcg gacccggggg  34320
tctgggccgc gcttcccgc ccgcgcgccg ctcgcgctcc cagggtgcag ggacgccagc  34380
gagggcccca gcggagagag gtcgaatcgg cctaggctgt ggggtaaccc gagggagggg  34440
ccatgatgtg gaggccctgg gaacaggtgc gtgcggcgac cctttggccg ctggcctgat  34500
ccggagaccc agggctgcct ccaggtccgg acgcggggcg tcgggctccg ggcaccacga  34560
atgccggacg tgaaggggag gacggaggcg cgtagacgcg gctggggacg aacccgagga  34620
cgcattgctc cctggacggg cacgcgggac ctcccggagt gcctccctgc aacacttccc  34680
cgcgacttgg gctccttgac acaggcccgt catttctctt tgcaggttct caggcggcga  34740
ggggtcccca ccatgagcaa accaccccaa atctgttaat cacccaccgg ggcggtcccg  34800
tcgagaaagg gtgggaaatg gagccaggcg ctcctgctgg ccgcgcaccg ggcgcctcac  34860
accagccaca acgccttga ccctgggccc cggcactctg tctggcagat gaggccaaca  34920
tctggtcaca tcccgcccgc acagggtgga gggcagcctc ggggtccagg cacctggctc  34980
caagcctcgg actgcagagc taggaggccc gacttcagc ccagcagtag aagccacacg  35040
gccactggtc ccctccagac ctggggcccc ggcacaaccg caggacagct gaggacttcc  35100
caggaatcca gactccgggt tgctcaagtt tggatctaag gggcgagaaa cttctgggtc  35160
tcccgaggcc ttgcagggat gctgtagctg aggtcggcaa acactgaaat gctaacaaac  35220
```

-continued

| | |
|---|---|
| gcaaccttaa atgtaacctt tcctactttc agaaactgcc ggaggaaatt gctttattta | 35280 |
| tggagctagc atttgaacag gcctcgcacc ctccctgggc tgtcacgctc gctggaggtt | 35340 |
| agcctcgtct tgtaaatact taggattacg ggtcgctctt ctagaaatcc ccttagtgat | 35400 |
| ccctaagcct tttaaaggg ctgtgtttgt gaattgtctc tgccactagg gcaaaggggc | 35460 |
| ggtttggaaa atttgttcca acaaaagtta agttgtagct tacactggtt ctctgcagag | 35520 |
| aagccaacat agaaaacaca attttaaaag agggaagaga agaaatggaa gcagaagatt | 35580 |
| atgctggagt aattaacacc atgtgcatgg cgaggaaacg cctcccggca ttcaatgaag | 35640 |
| atcgctgata cccagaagac accccagtat tatgggtgca gttagtgtgt ctttgaaaag | 35700 |
| ctgatgatta cttcccatt taagaaaact acaattccca acacatacaa gttactccgc | 35760 |
| cctaaaacct acgtcacccg ccccgttccc acgcccgcg ccacgtcaca aactccaccc | 35820 |
| cctcattatc atattggctt caatccaaaa taaggtatat tattgatgat g | 35871 |

<210> SEQ ID NO 3
<211> LENGTH: 1677
<212> TYPE: DNA
<213> ORGANISM: Adenovirus

<400> SEQUENCE: 3

| | |
|---|---|
| atcagcgctg cctgaaactc gcgccgcgag gagagggcgg ggccgcggaa aggaagggga | 60 |
| ggggctggga gggcccggag ggggctgggc cggggacccg ggaggggtcg ggacggggcg | 120 |
| gggtccgcgc ggaggaggcg gagctggaag gtgaaggggc aggacgggtg cccgggtccc | 180 |
| cagtccctcc gccacgtggg aagcgcggtc ctgggcgtct gtgcccgcga atccactggg | 240 |
| agcccggcct ggccccgaca gcgcagctgc tccggcgga cccgggggtc tgggccgcgc | 300 |
| ttccccgccc gcgcgccgct cgcgctccca gggtgcaggg acgccagcga gggccccagc | 360 |
| ggagagaggt cgaatcggcc taggctgtgg ggtaacccga gggaggggcc atgatgtgga | 420 |
| ggccctggga acaggtgcgt gcggcgaccc tttggccgct ggcctgatcc ggagacccag | 480 |
| ggctgcctcc aggtccggac gcggggcgtc gggctccggg caccacgaat gccgacgtg | 540 |
| aaggggagga cggaggcgcg tagacgcggc tggggacgaa cccgaggacg cattgctccc | 600 |
| tggacgggca cgcgggacct cccggagtgc ctccctgcaa cacttccccg cgacttgggc | 660 |
| tccttgacac aggcccgtca tttctctttg caggttctca ggcggcgagg ggtccccacc | 720 |
| atgagcaaac caccccaaat ctgttaatca cccaccgggg cggtcccgtc gagaaagggt | 780 |
| gggaaatgga gccaggcgct cctgctggcc gcgcaccggg cgcctcacac cagccacaac | 840 |
| ggccttgacc ctgggccccg gcactctgtc tggcagatga ggccaacatc tggtcacatc | 900 |
| ccgcccgcac agggtggagg gcagcctcgg ggtccaggca cctggctcca agcctcggac | 960 |
| tgcagagcta ggaggcccga cttccagccc agcagtagaa gccacacggc cactggtccc | 1020 |
| ctccagacct ggggccccgg cacaaccgca ggacagctga ggacttccca ggaatccaga | 1080 |
| ctccggttg ctcaagtttg gatctaaggg gcgagaaact tctgggtctc ccgaggcctt | 1140 |
| gcagggatgc tgtagctgag gtcggcaaac actgaaatgc taacaaacgc aaccttaaat | 1200 |
| gtaacctttc ctactttcag aaactgccgg aggaaattgc tttatttatg gagctagcat | 1260 |
| tgaacaggc ctcgcaccct ccctgggctg tcacgctcgc tggaggttag cctcgtcttg | 1320 |
| taaatactta ggattacggg tcgctcttct agaaatcccc ttagtgatcc ctaagccttt | 1380 |
| ttaaagggct gtgtttgtga attgtctctg ccactagggc aaaggggcgg tttggaaaat | 1440 |
| ttgttccaac aaaagttaag ttgtagctta cactggttct ctgcagagaa gccaacatag | 1500 |

```
aaaacacaat tttaaaagag ggaagagaag aaatggaagc agaagattat gctggagtaa    1560
ttaacaccat gtgcatggcg aggaaacgcc tcccggcatt caatgaagat cgctgatacc    1620
cagaagacac cccagtatta tgggtgcagt tagtgtgtct ttgaaaagct gatgatt       1677
```

RECOMBINANT ADENOVIRUS VECTORS THAT ARE REPLICATION-COMPETENT IN TERT-EXPRESSING CELLS

RELATED APPLICATION

This application claims the benefit of the filing date of provisional application Ser. No. 60/233,872, filed on Sep. 20, 2000, entitled "A Method to Restrict the Replication of Replication-competent Adenovirus Vectors to Neoplastic Cells". Provisional application No. 60/233,872 is herein incorporated by reference in its entirety. This application is also a continuation-in-part of U.S. application Ser. No. 09/351,778 filed on Jul. 12, 1999, incorporated by reference herein in its entirety.

REFERENCE TO GOVERNMENT GRANT

This invention was made with government support under a grant from the National Institutes of Health, Grant Number RO1 CA71704. The government has certain rights in this invention.

BACKGROUND OF INVENTION

1. Field of the Invention

This invention relates generally to recombinant adenovirus vectors which overexpress adenovirus death proteins (ADP) and which are replication-restricted to cells expressing telomerase.

2. Description of the Related Art

Cancer is a leading cause of death in the United States and elsewhere. Depending on the type of cancer, it is typically treated with surgery, chemotherapy, and/or radiation. These treatments often fail: surgery may not remove all the cancer; some cancers are resistant to chemotherapy and radiation therapy; and chemotherapy-resistant tumors frequently develop. New therapies are necessary, to be used alone or in combination with classical techniques.

One potential therapy under active investigation is treating tumors with recombinant viral vectors expressing anti-cancer therapeutic proteins. Adenovirus-based vectors contain several characteristics that make them conceptually appealing for use in treating cancer, as well as for therapy of genetic disorders. Adenoviruses (hereinafter used interchangeably with "Ads") can easily be grown in culture to high titer stocks that are stable. They have a broad host range, replicating in most human cancer cell types. Their genome can be manipulated by site-directed mutation and insertion of foreign genes expressed from foreign promoters.

The adenovirion consists of a DNA-protein core within a protein capsid (reviewed by Stewart et al., "Adenovirus structure by x-ray crystallography and electron microscopy." in: *The Molecular Repertoire of Adenoviruses*, Doerfler, W. et al., (ed), Springer-Verlag, Heidelberg, Germany, p. 25–38). Virions bind to a specific cellular receptor, are endocytosed, and the genome is extruded from endosomes and transported to the nucleus. The genome is a linear double-stranded DNA of about 36 kbp, encoding about 36 genes (FIG. 1A). In the nucleus, the "immediate early" E1A proteins are expressed initially, and these proteins induce expression of the "delayed early" proteins encoded by the E1B, E2, E3, and E4 transcription units (reviewed by Shenk, T. "Adenoviridae: the viruses and their replication" in: *Fields Virology*, Fields, B.N. et al., Lippencott-Raven, Philadelphia, p. 2111–2148). E1A proteins also induce or repress cellular genes, resulting in stimulation of the cell cycle. About 23 early proteins function to usurp the host cell and initiate viral DNA replication. Cellular protein synthesis is shut off, and the cell becomes a factory for making viral proteins. Virions assemble in the nucleus at about 1 day post infection (p.i.), and after 2–3 days the cell lyses and releases progeny virus. Cell lysis is mediated by the E3 11.6K protein, which has been renamed "adenovirus death protein" (ADP) (Tollefson et al., *J Virol.* 70:2296–2306, 1996; Tollefson et al., *Virol.* 220:152–162, 1996). The term ADP as used herein in a generic sense refers collectively to ADP's from adenoviruses such as, e.g. Ad type 1 (Ad1), Ad type 2 (Ad2), Ad type 5 (Ad5) or Ad type 6 (Ad6) all of which express homologous ADP's with a high degree of sequence similarity.

The Ad vectors being investigated for use in anti-cancer and gene therapy are based on recombinant Ad's that are either replication-defective or replication-competent. Typical replication-defective Ad vectors lack the E1A and E1B genes (collectively known as E1) and contain in their place an expression cassette consisting of a promoter and pre-mRNA processing signals which drive expression of a foreign gene. (See e.g. Felzmann et al., *Gene Ther.* 4: 1322–1329, 1997; Topf et al., *Gene Ther.* 5:507–513, 1998; Putzer et al., *Proc. Natl. Acad. Sci. USA* 94:10889–10894, 1997; Arai et al., *Proc. Natl Acad. Sci. USA* 94:13862–13867, 1997). These vectors are unable to replicate because they lack the E1A genes required to induce Ad gene expression and DNA replication. In addition, the E3 genes are usually deleted because they are not essential for virus replication in cultured cells.

It is recognized in the art that replication-defective Ad vectors have several characteristics that make them suboptimal for use in therapy. For example, production of replication-defective vectors requires that they be grown on a complementing cell line that provides the E1A proteins in trans. Such cell lines are fastidious, and generation of virus stocks is time-consuming and expensive. In addition, although many foreign proteins have been expressed from such vectors, the level of expression is low compared to Ad late proteins.

To address these problems, several groups have proposed using replication-competent Ad vectors for therapeutic use. Replication-competent vectors retain Ad genes essential for replication and thus, do not require complementing cell lines to replicate. Replication-competent Ad vectors lyse cells as a natural part of the life cycle of the vector. Another advantage of replication-competent Ad vectors occurs when the vector is engineered to encode and express a foreign protein. (See e.g. Lubeck et al., *AIDS Res. Hum. Retroviruses* 10:1443–1449, 1994). Such vectors would be expected to greatly amplify synthesis of the encoded protein in vivo as the vector replicates. For use as anti-cancer agents, replication-competent viral vectors would theoretically also be advantageous in that they should replicate and spread throughout the tumor, not just in the initially infected cells as is the case with replication-defective vectors.

Because many human tissues are permissive for Ad infection, a method should be devised to limit the replication of the virus to the target cells. To specifically target tumor cells, several research laboratories have manipulated the E1B and E1A regions of the adenovirus. For example, Onyx Pharmaceuticals recently reported on adenovirus-based anti-cancer vectors which are replication-deficient in non-neoplastic cells, but which exhibit a replication phenotype in neoplastic cells lacking functional p53 and/or retinoblastoma (pRB) tumor suppressor proteins (U.S. Pat. No. 5,677,178; Heise et al., *Nature Med.* 6:639–645, 1997; Bischoff et al., *Science* 274:373–376, 1996). This phenotype is reportedly accomplished by using recombinant adenoviruses containing a mutation in the E1B region that renders the encoded E1B-55K protein incapable of binding to p53 and/or a mutation(s) in the E1A region which make the encoded E1A protein (p289R or p243R) incapable of binding to pRB and/or p300 and/or p107. E1B-55K has at least two independent functions: it binds and inactivates the tumor suppressor protein p53, and it is required for efficient transport of Ad MRNA from the nucleus. Because these E1B and E1A viral proteins are involved in forcing cells into S-phase, which is required for replication of adenovirus DNA, and because the p53 and pRB proteins block cell cycle progression, the recombinant adenovirus vectors described by Onyx should replicate in cells defective in p53 and/or pRB, which is the case for many cancer cells, but not in cells with wild-type p53 and/or pRB. Onyx has reported that replication of an adenovirus lacking E1B-55K, named ONYX-015, was restricted to p53-minus cancer cell lines (Bischoff et al., supra), and that ONYX-015 slowed the growth or caused regression of a p53-minus human tumor growing in nude mice (Heise et al., supra). Others have challenged the Onyx report claiming that replication of ONYX-015 is independent of p53 genotype and occurs efficiently in some primary cultured human cells (Harada and Berk, *J. Virol* 73:5333–5344, 1999). ONYX-015 does not replicate as well as wild-type adenovirus because E1B-55K is not available to facilitate viral mRNA transport from the nucleus. Also, ONYX-015 expresses less ADP than wild-type virus.

As an extension of the ONYX-015 concept, a replication-competent adenovirus vector was designed that has the gene for E1B-55K replaced with the herpes simplex virus thymidine kinase gene (Wilder et al., *Gene Therapy* 6:57–62, 1999). The group that constructed this vector reported that the combination of the vector plus gancyclovir showed a therapeutic effect on a human colon cancer in a nude mouse model (Wilder et al., *Cancer Res.* 59:410–413, 1999). However, this vector lacks the gene for ADP, and accordingly, the vector will lyse cells and spread from cell-to-cell less efficiently than an equivalent vector that expresses ADP.

To target tumor cells, other research groups have taken advantage of the differential expression of telomerase in dividing cells. Telomerase is a ribonucleoprotein enzyme which is responsible for the maintenance of telomeres. Telomeres are long tandem repetitions of a simple sequence, for example TTAGGG, at both ends of the chromosomes, the very ends of which, because of the nature of DNA replication do not get duplicated (review Blackburn, E. H. *Nature* 350:569–573, 1991). As a result, telomeres shorten by each round of cell division (Harley, C B. et al. *Nature* 345:458–460, 1990), in the long run causing chromosomal instability and cellular senescence (Greider, C. W. *Cell* 67:645–647, 1991). To counteract this effect, embryonic cells, germ cells, stem cells, and hematopoietic cells (Ulaner, G/A. et al. *Cancer Res.* 58:4168–4172, 1998; Broccoli, D. et al. *Proc. Natl. Acad. Sci. USA* 92, 9082–9086, 1995; Kalquist, K. A. et al. *Nature Genetics* 19:182–186, 1998) produce the telomerase enzyme, which maintains the original length of the telomeres. Some epithelial basal cells in the skin and intestine also express low levels of telomerase (Yasumoto, S. et al. *Oncogene* 13:433–439,1996; Härle-Bachor, C. and Boukamp, P. *Proc. Natl. Acad. Sci. USA* 93:6476–6481, 1996). Cancerous cells, on the other hand, are continuously dividing, without going into senescence. After an initial period of shortening in these dividing cells, the lengths of the telomeres stabilize. Further research proved that this stabilization was due to the reactivation of telomerase (Blasco, M. A. et al. *Nature Genetics* 12:200–204, 1996). A systematic search showed that late stage tumors exhibit high levels of telomerase activity (Kim, N. W. et al. *Science* 266:2011–2015, 1994; Shay, J. W. and Bachetti, S. *Eur. J. Cancer,* 33:787–791, 1997; Yan, P. et al. *Cancer Res.* 59:3166–3170, 1999).

The telomerase holoenzyme consists of two subunits: an RNA molecule and a protein (Morin, G. B. *Cell* 59:521–529, 1989). The RNA serves as the template for the telomere sequences (Feng, J. et al. *Science* 269:1236–1241, 1995), while the protein (human Telomerase Reverse Transcriptase or "hTERT") harbors reverse transcriptase activity (Harrington, L. et al. *Science* 275:973–977, 1997). The expression of hTERT is tightly regulated (Meyerson, M. et al. *Cell* 90:785–789, 1997). The regulatory role of hTERT in telomerase activity is further evidenced by the fact that introducing hTERT into telomerase-negative cells results in telomerase activation (Bodnar, A. G. et al. *Science* 279:349–352, 1998).

The regulation occurs mainly at the transcriptional level, though other mechanisms-alternative splicing (Ulaner, G. A. et al. *Int. J Cancer* 85:330–335, 2000)—have been implicated, too. The promoter of hTERT was cloned and sequenced by several groups (Cong, Y-S. et al *Hum. Mol. Genet.* 8:137–142, 1999, Horikawa, I. et al. *Cancer Res.* 59:826–830, 1999; Takakura, M. et al *Cancer Res.* 59:551–559, 1999; Wick, M. et al. *Gene* 232:97–106, 1999). It was shown that the isolated hTERT promoter was unable to direct the transcription of a reporter gene in cells with no telomerase activity, but it worked effectively in established telomerase positive cell lines (Horikawa et al.). The hTERT promoter binds various transcription factors (review Poole, J. C. et al. *Gene* 269:1–12, 2001). Of these, the cMyc/Max/ Mad1 factors seem to be the most important for regulation. The promoter contains two binding sites (E-boxes) that can bind either the cMyc/Max or the Mad 1/Max heterodimer. While the former one activates, the latter represses hTERT transcription. The distribution of cMyc and Mad1 in adult organs/tissues coincides with the activity —or lack of activity— of the hTERT promoter in those tissues (Günes, C. et al. *Cancer Res.* 60:2116–2121, 2000). In certain organs (endometrium, ovary) estrogen (Misiti, S. et al. *Molec. Cell. Biol.* 20:3764–3771, 2000), in others (kidney, spleen) the Wilms' Tumor 1 tumor suppressor (WT1) (Oh, S. et al. *J. Biol. Chem.* 174:37473–37478, 1999), might have a regulatory role.

By using the hTERT promoter, any protein can be expressed selectively in telomerase positive, that is—at least in adult human-neoplastic cells. Researchers have expressed pro-apoptotic proteins (Koga, S. et al. *Hum. Gene. Ther.* 11: 1397–1406, 2000), bacterial toxins (Abduol-Ghani, R. et al. *Molecular Therapy* 2:539–544, 2000), and prodrug converting enzymes (Majumdar, A. S. et al. *Gene Therapy* 8:568–578, 2001) using various hTERT promoter containing vectors. Though limited to telomerase positive cells, these expression vectors do not effectively deliver the anti-cancer agent to neighboring tumor cells. Instead, to be effective, the vector would need to be introduced into each tumor cell.

Thus, there is a continuing need for an efficient and effective anti-cancer adenovirus vector that could specifically target neoplastic cells, while replicating poorly or not at all in normal tissue, and efficiently spreading to neighboring neoplastic cells, thereby maximizing the cancer-killing ability of the adenovirus vector.

SUMMARY OF THE INVENTION

Briefly, therefore, the present invention is directed to novel adenovirus vectors which overexpress an adenovirus death protein ("ADP") and which are replication-restricted to cells expressing telomerase. Overexpression of ADP by a recombinant adenovirus allows the construction of a replication-competent adenovirus that kills cells expressing telomerase and spreads from cell-to-cell at a rate similar to or faster than that exhibited by adenoviruses expressing wild-type levels of ADP, even when the recombinant adenovirus contains a mutation that would otherwise reduce its replication rate in non-neoplastic cells. The work herein demonstrates that substitution of the human telomerase reverse transcriptase promoter ("hTERT") for the adenovirus E4 promoter allows restriction of replication of the adenovirus to cells expressing telomerase without the need for complementation to achieve replication competence in these cells.

In one embodiment of the invention, the recombinant adenovirus vector comprises an ADP gene, a hTERT promoter, and at least one mutation in the E3 region. In a preferred embodiment, the hTERT-ADP-expressing vector comprises a recombinant adenovirus vector lacking expression of at least one E3 protein selected from the group consisting of: gp19K; RIDα (also known as 10.4K); RIDβ (also known as 14.5K) and 14.7K. Because wild-type E3 proteins inhibit immune-mediated inflammation and/or apoptosis of Ad-infected cells, it is believed that a recombinant adenovirus lacking one or more of these E3 proteins will stimulate infiltration of inflammatory and immune cells into a tumor treated with the adenovirus and that this host immune response will aid in destruction of the tumor as well as tumors that have metastasized. A mutation in the E3 region would impair its wild-type function, making the viral-infected host susceptible to attack by the host's immune system. Such a vector is identified as GZ3-TERT and its sequence is represented in SEQ ID NO. 1.

In still another embodiment of the invention, the recombinant adenovirus vector comprises an ADP gene, a hTERT promoter, and at least one inactivating mutation in the E1A region, resulting in a loss of transformation of resting cells by E1A without inhibiting its function in the targeted cells. The mutation in the E1A region disrupts E1A protein binding to p300 and/or members of the Rb family. Without this binding, E1A cannot provoke $G_0$ exit and subsequent entry into S phase, an essential progression for synthesis of molecules necessary for adenoviral replication. Thus, a resting cell (i.e. one in $G_0$ state) cannot support replication of the recombinant adenovirus vector of the present invention. Such a vector is identified as KD3-TERT and its sequence is represented in SEQ ID NO. 2.

Another embodiment of the invention involves a pharmaceutical composition comprising the recombinant adenovirus vector of the present invention in association with a pharmaceutically acceptable carrier.

Yet another embodiment of the invention is directed at an in vitro method and kit for promoting death of cells expressing telomerase comprising contacting said cell with an effective amount of KD3-TERT, GZ3-TERT, or both.

Still another embodiment of the invention is directed at a method for promoting death of neoplastic cells in a patient comprising administering an effective amount of the adenovirus vector(s) of the present invention to said patient.

Among the several advantages found to be achieved by the present invention, therefore, may be noted the provision of replication-competent adenovirus vectors, which rapidly kill cancer cells and spread from cell-to-cell in a tumor; the provision of such vectors whose replication can be restricted to cells expressing telomerase; the provision of pharmaceutical compositions for anti-cancer therapy which cause little to no side effects in normal tissues; and the provision for methods and kits for promoting death in cells expressing telomerase, such as neoplastic cells.

Figure 1:
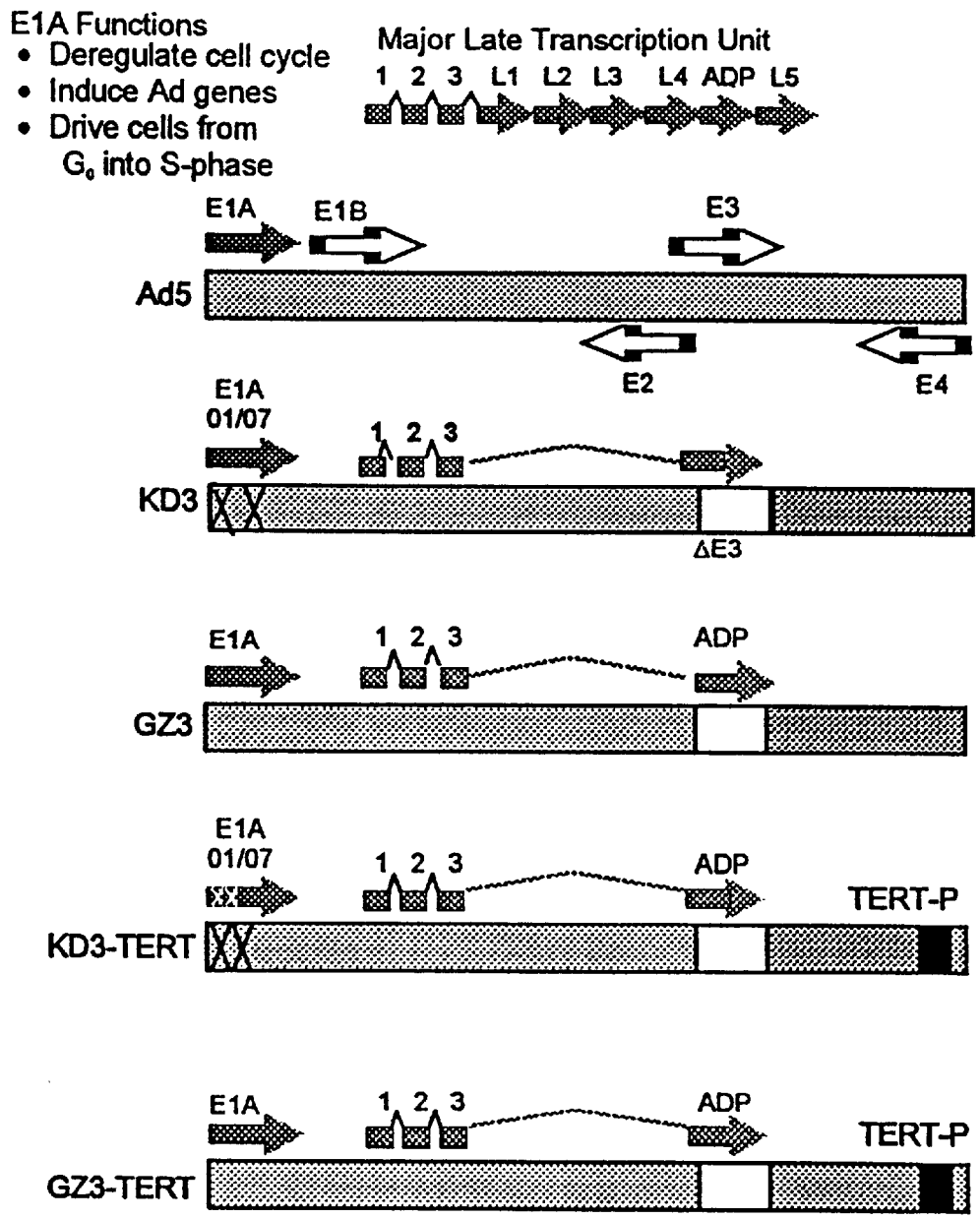
FIG. 1 is a schematic diagram of the adenovirus type 5 (Ad5) and the adenovirus vectors, respectively.

Ad5. The horizontal bar indicates the duplex DNA genome of 36 kbp encoding ca. 34 genes. The arrows indicate transcription units. The "immediate early" E1A proteins induce expression of the "delayed early" proteins coded by the E1B, E2, E3, and E4 transcription units. Viral DNA begins to replicate at about 7 h postinfection (p.i.), then "late" proteins derived from the major late transcription unit are synthesized. The major late mRNAs are formed by alternative splicing and polyadenylation of a large pre-mRNA initiated at the single major late promoter and extending to the right end of the genome. All late mRNAs have a tripartite leader (leaders 1, 2, and 3) at their 5' termini that facilitates translation. Beginning at 20–24 h p.i., virions begin to assemble in the cell nucleus, then after 2–3 days the cells begin to lyse and release virions, with lysis complete by about 5–6 days. Efficient cell lysis is mediated by ADP. ADP is a late protein derived from the major late transcription unit.

KD3. KD3 lacks all E3 genes but the 12.5K gene. The adp gene is reinserted into the deletion such that the ADP major late mRNA will be formed abundantly with the tripartite leader at its 5'-terminus.

GZ3. This is identical to KD3 except it has wild-type E1A.

KD3-TERT. Identical to KD3 except it has the E4 promoter replaced by the cancer-specific TERT promoter.

GZ3-TERT. Identical to GZ3 except it has the E4 promoter replaced by the cancer-specific TERT promoter.

FIG. 2 shows the cytopathic effect caused by GZ3-TERT and GZ3 in SW480 cells. SW480 colon cancer cells were grown in monolayers and infected with 10 pfu per cell of GZ3-TERT or GZ3 and were visualized by phase contrast microscopy and then photographed.

FIG. 3 shows the cytopathic effect caused by GZ3-TERT and GZ3 in LNCaP cells. LNCaP prostate cancer cells were grown in monolayers and infected with 10 pfu per cell of GZ3-TERT or GZ3 and were visualized by phase contrast microscopy and then photographed.

FIG. 4 shows the results of a cell viability assay of LS513 carcinoma (cecum, human) cells, SWI 116 adenocarcinoma (colon, human) cells, LS174T adenocarcinoma (colorectal, human) cells, HepG2 hepatocellular carcinoma (human) cells, SW480 colon cancer cells, and LNCaP prostate cancer cells. These cells were grown in monolayers and were either mock-infected or infected with 10 pfu per cell of dl309, GZ3 or GZ3-TERT. The low molecular weight dye Trypan blue was added. Trypan blue stains cells with compromised membrane integrity, i.e. dead cells. The percent viability was calculated by counting the number of live (non-blue) cells for each test condition, dividing by the total number of cells, and multiplying by 100. The bars show the % viability.

FIG. 5 shows the result of a cell viability assay of HT29 adenocarcinoma (colon, human) cells, NCI-H441 bronchio-alveolar carcinoma (human, lung) cells, and MCF-7 adenocarcinoma (breast, human) cells. The cells were grown in monolayers and were either mock-infected or infected with 10 pfu per cell of GZ3 or GZ3-TERT. The low molecular weight dye Trypan blue was added, and the percent of viable cells was calculated.

Figure 6:
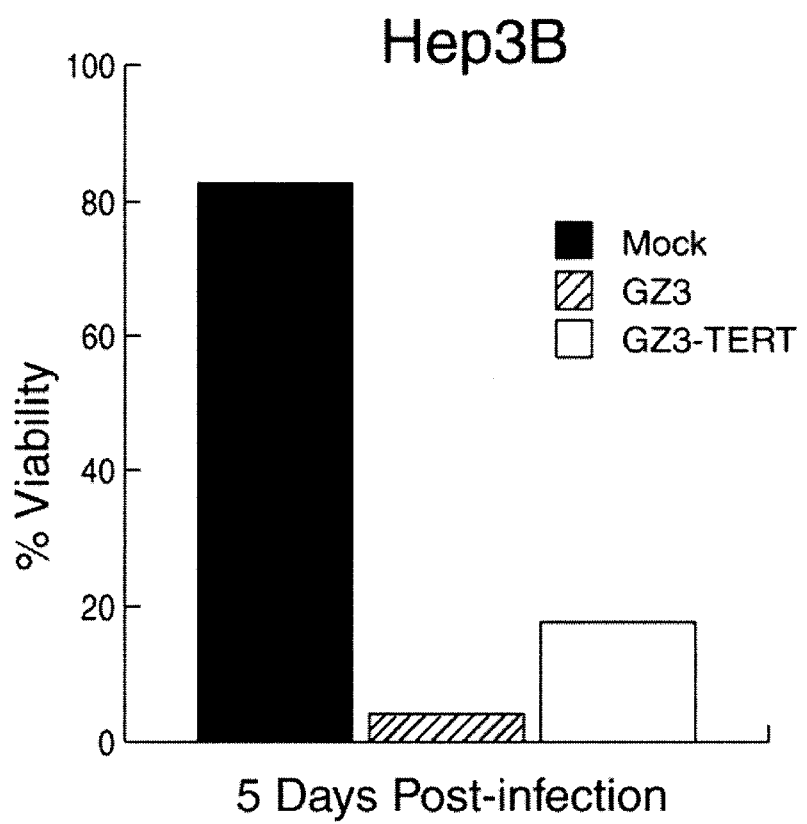
Figure 7A:
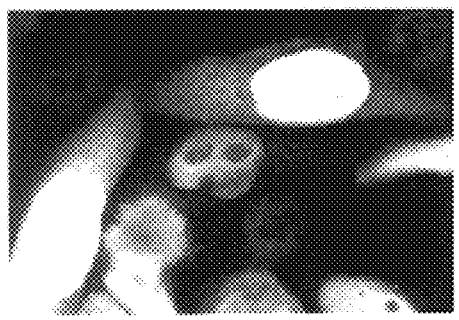
Figure 7B:
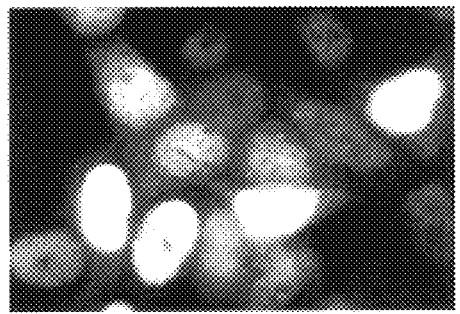
Figure 7C:
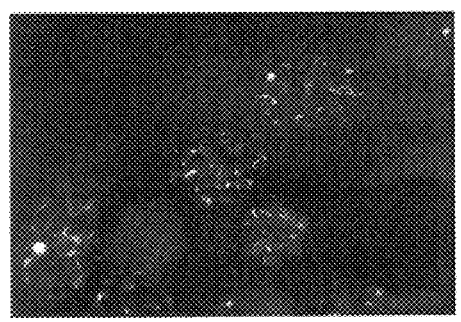
Figure 7D:
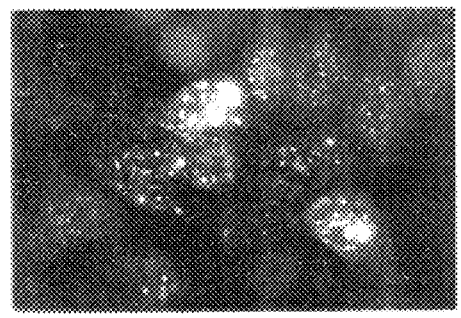
Figure 8A:
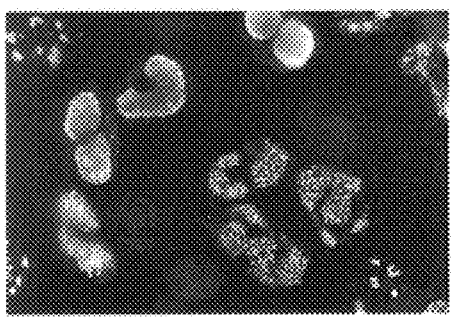
Figure 8B:
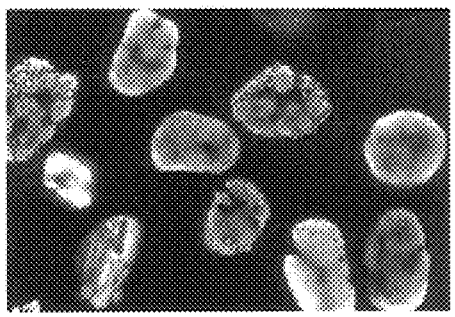
Figure 8C:
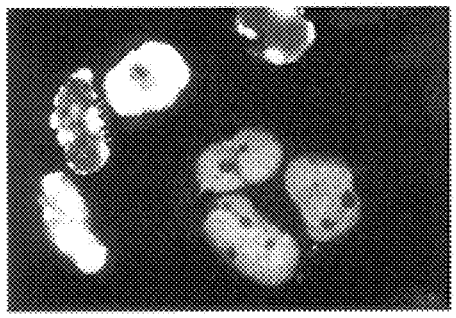
Figure 8D:
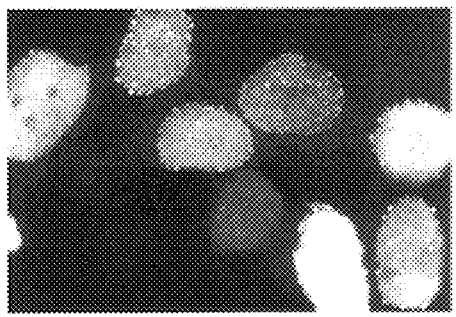
Figure 9A:
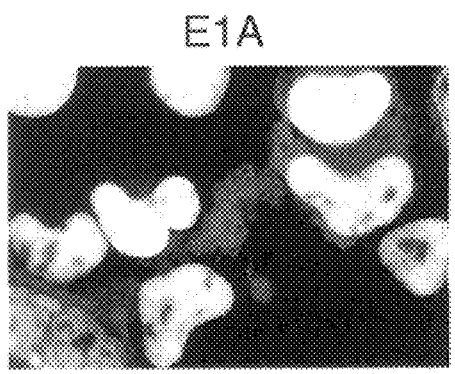
Figure 9B:
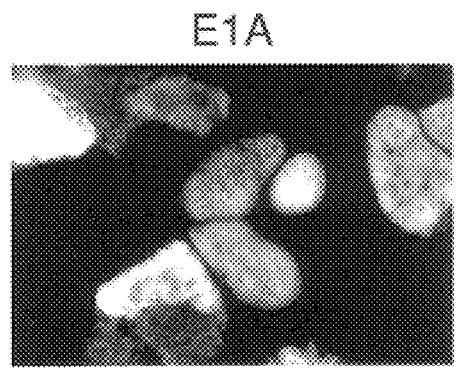
Figure 9C:
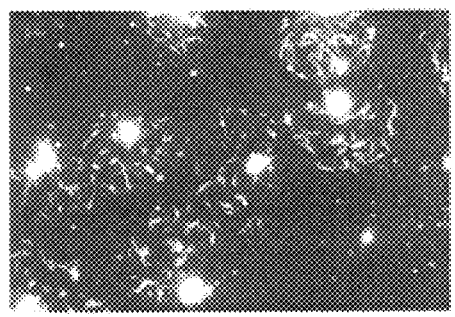
Figure 9D:
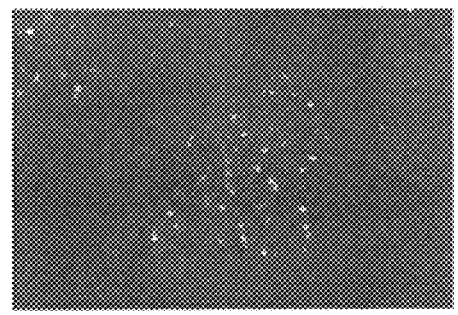

FIG. 6 shows the result of a cell viability assay in Hep3B liver cancer cells. These cells were grown in monolayers and were either mock-infected or infected with 10 pfu per cell of GZ3 or GZ3-TERT. The low molecular weight dye Trypan blue was added, and the percent viability was calculated.

FIG. 7 shows the result of an indirect immunofluorescence assay for E1A and E4ORF3 adenovirus proteins in HeLa cervical cancer cells. The cells were grown in monolayers and infected with 10 pfu per cell of GZ3 (Panels A, C) or GZ3-TERT (Panels B, D). At approximately 2 days postinfection, cells were incubated with primary antibodies against the Ad5 E1A protein (Panels A, B) (mouse monoclonal antibody) or the Ad5 E4ORF3 protein (Panels C, D) (rabbit antiserum). Cells were washed incubated with secondary antibodies (goat anti-rabbit IgG-FITC conjugate and goat anti-mouse IgG-RITC conjugate) to visualize expression and localization of the Ad5 E1A and E4ORF3 proteins. Panels A and C show the same field of cells. Panels B and D show the same field of cells.

FIG. 8 shows the result of an indirect immunofluorescence assay for the DBP (DNA binding protein) (Panels A, B) and fiber (Panels C, D) adenovirus proteins in HeLa cervical cancer cells. The cells were grown in monolayers and infected with 10 pfu per cell of GZ3 (Panels A, C) or GZ3-TERT (Panels B, D). At approximately 2 days postinfection, the cells were incubated with primary antibodies against the Ad5 DBP (rabbit antipeptide antiserum) or against the Ad5 fiber protein (mouse monoclonal antibody). Cells were washed and incubated with secondary antibodies (goat anti-rabbit IgG-FITC conjugate and goat anti-mouse IgG-RITC conjugate) to visualize expression and localization of the Ad5 proteins. Panels A and C show the same field of cells as do Panels B and D.

FIG. 9 shows the result of an indirect immunofluorescence assay of E1A (Panels A, B) and E4ORF3 (Panels C, D) proteins in A549 lung alveolar cancer cells infected with GZ3 (Panels A, C) or GZ3-TERT (Panels B, D). The methods for infection and immunostaining were similar to those described in the legend to FIG. 7. Panels A and C show the same field of cells as do Panels B and D.

FIG. 10 shows the result of a indirect immunofluorescence assay for DBP (Panels A, B) and fiber (Panels C, D) in A549 cells infected with GZ3 (Panels A,C) or GZ3-TERT (Panels B, D). The methods for infection and immunostaining were similar to those described in the legend for FIG. 8. Panels A and C show the same field of cells as do Panels B and D.

FIG. 11 shows an indirect immunofluorescence assay for E1A (Panels A, B) and E4ORF3 (Panels C, D) proteins in Hep3B liver cancer cells infected with GZ3 (Panels A, C) or GZ3-TERT (Panels B, D). The methods for infection and immunostaining were similar to those described for FIG. 7. Panels A and C show the same filed of cells as do Panels B and D.

FIG. 12 shows an indirect immunofluorescence assay for DBP (Panels A, B) and fiber (Panels C, D) in Hep3B cells infected with GZ3 (Panels A, C) or GZ3-TERT (Panels B, D). The methods for infection and immunostaining were similar to those described for FIG. 8. Panels A and C show the same field of cells as do Panels B and D.

Figure 13A:
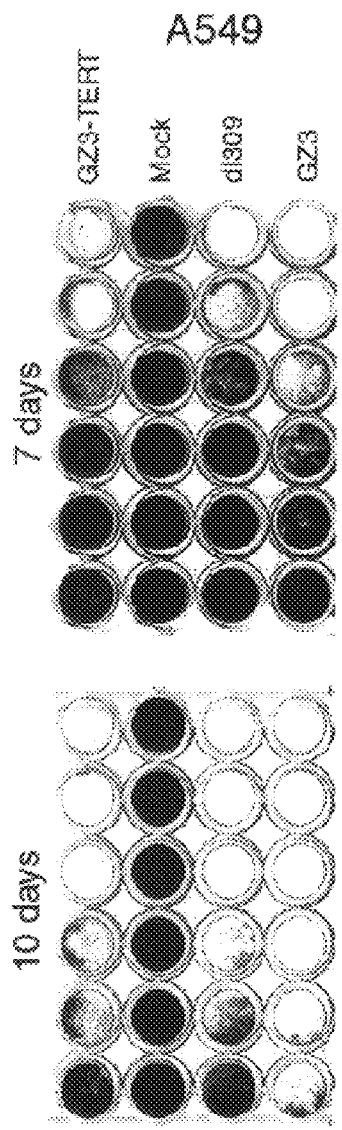

FIG. 13 shows the ability of GZ3, GZ3-TERT and dl309 to replicate within and destroy A549, SW480, or LS513 cancer cell lines. Cells were grown to 70 to 80% confluency in 48 well plates. These cell lines, growing in monolayers, were either mock-infected or infected with various multiplicities (serial dilutions ranging from $10^1$ to $10^{-4}$ pfu/cell) of dl309, GZ3, or GZ3-TERT in duplicate. The cells were stained with crystal violet dye (1% crystal violet, 10% formaldehyde, 20% methanol) at 7 or 10 days postinfection, or 12 or 13 days postinfection, depending on the cell line. The crystal violet stain was aspirated from the cell surface after 15 minutes and the plates were washed. Cells attached to the surface stained blue.

Figure 14:
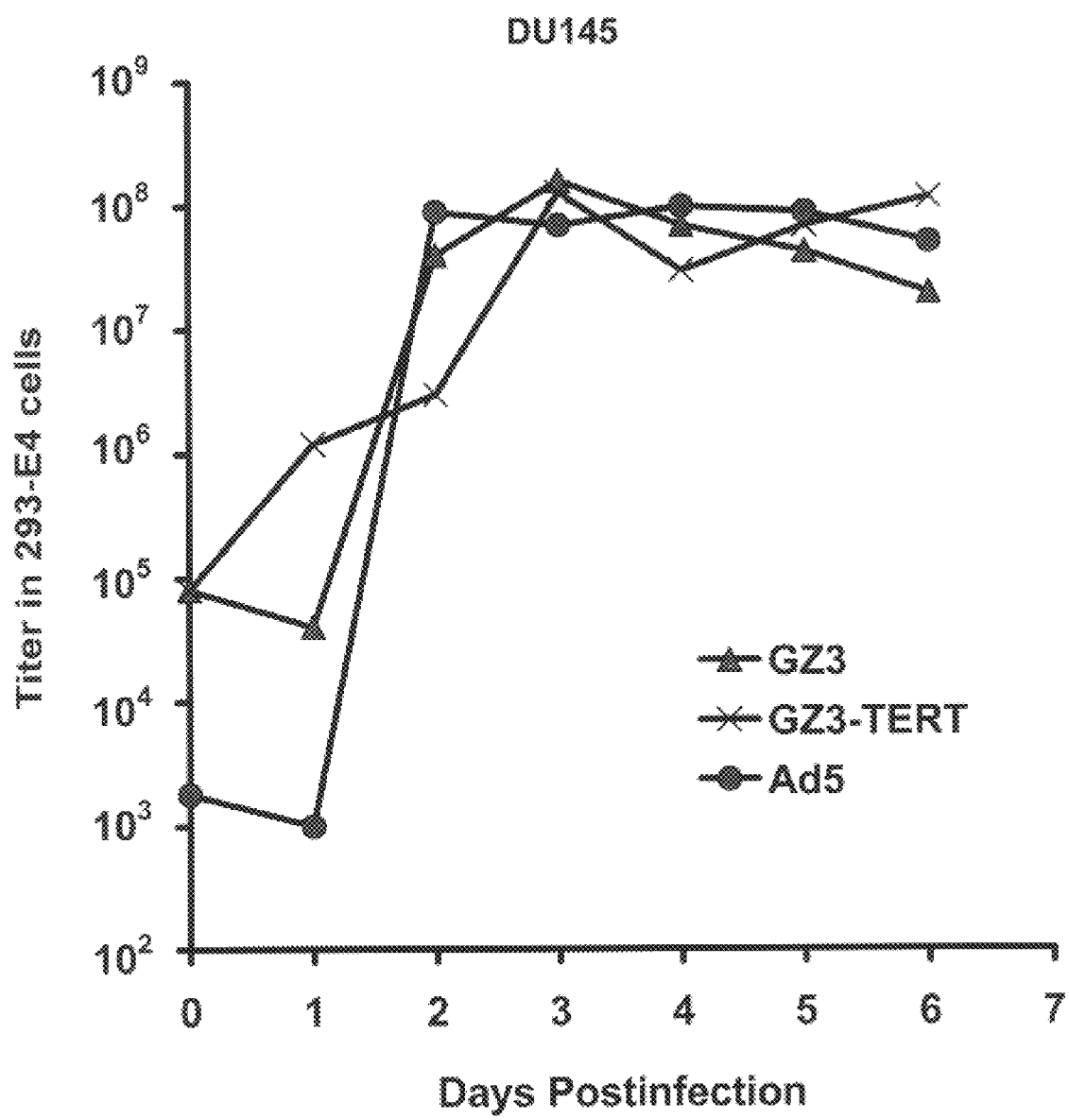

FIG. 14 shows a single step growth curve for GZ3-TERT, GZ3, and Ad5 in DU145 human prostate cancer cells. The cells were grown to about 60–70% confluency in 35 mm Petri dishes. The cells were infected at a multiplicity of 10 pfu/cell with Ad5, GZ3, or GZ3-TERT (8 dishes per virus). After 1 hour, cells were washed with medium three times to clear away any non-attached virus. Complete medium (2 ml) was added back to the dishes. One dish was frozen from each set of eight at this time, and then every day for 7 consecutive days. The cells were freeze-thawed three times, and then the lysates were cleared by low speed centrifugation. The virus yield was determined by titering the supernatants on 293 E4 cells. 293 E4 cells are a human embryonic kidney cell line that contains the Ad5, E1A, E1B, and E4 genes (Krougliak and Graham, *Hum Gene Ther* 6:1575–1586, 1995).

Figure 15:
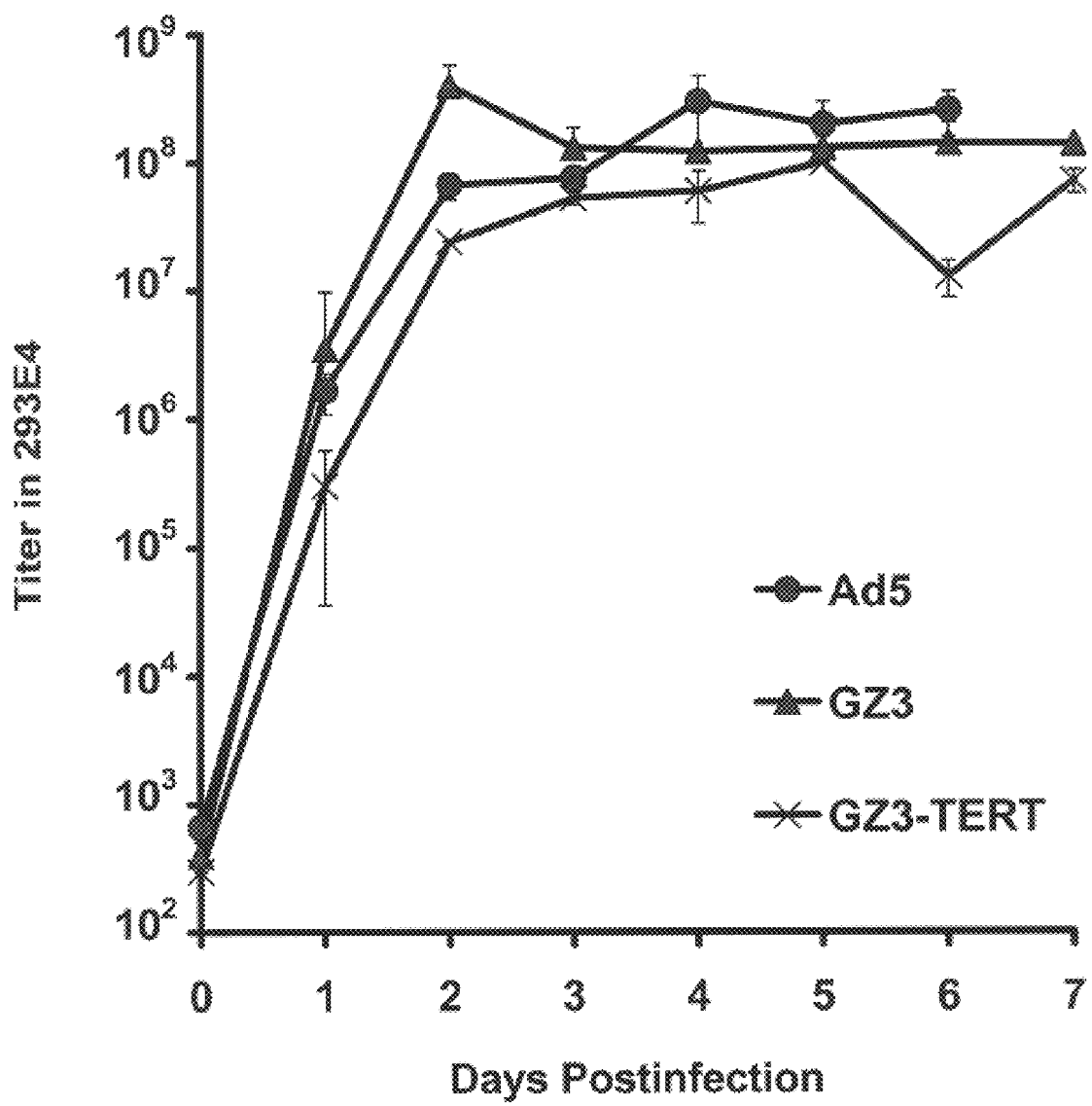

FIG. 15 shows a single step growth curve for GZ3-TERT, GZ3, and Ad5 in A549 human lung cancer cells. The methods used were identical to those used for FIG. 14.

Figure 16:
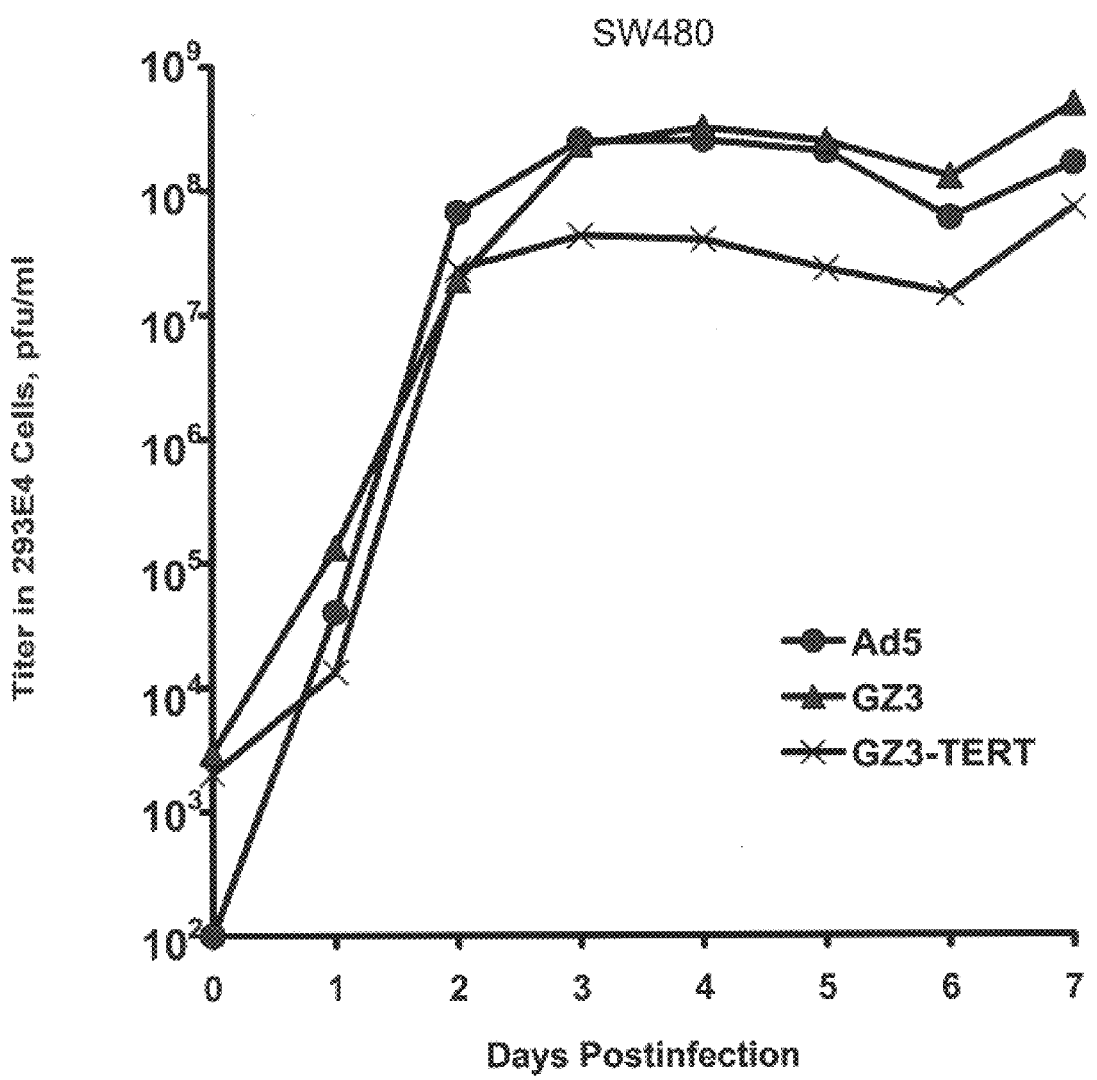

FIG. 16 shows a single step growth curve for GZ3-TERT, GZ3, and Ad5 in SW480 human colon cancer cells. The methods used were identical to those for FIG. 14.

DETAILED DESCRIPTION OF INVENTION

Definitions

"Acceptable carrier" refers to a carrier that is compatible with the other ingredients of the formulation and is not deleterious to the recipient thereof.

"Adenovirus" refers to human adenovirus serotype 5 (Ad5).

"Adenovirus vector" or "vector" refers to a recombinant molecular vehicle of adenoviral origin that can effectively deliver an anti-cancer agent to a susceptible host cell.

"Overexpress" or "overexpression" refers to the ability of the recombinant adenovirus vector to express more ADP molecules per viral genome present in a host cell infected by the vector than expressed by a nonrecombinant adenovirus vector.

"Replication-competent" refers to vectors that can replicate in a host cell without the need for complementation.

"Replication-restricted" refers to vectors that replicate exclusively or almost exclusively in dividing cells, preferably cells that express telomerase, more preferably in dividing neoplastic cells.

Description

Unless otherwise indicated, the practice of the present invention employs conventional techniques of cell culture, molecular biology, microbiology, recombinant DNA manipulation, immunology science, which are within the skill of the art. Such techniques are explained fully in the literature. See, e.g., DNA CLONING, Volumes I and II (D. N. Glover, ed., 1985); OLIGONUCLEOTIDE SYNTHESIS (M. J. Gait ed., 1984); NUCLEIC ACID HYBRIDIZATION (B. D. Harnes and S. J. Higgins, eds., 1984); B. Perbal, A PRACTICAL GUIDE TO MOLECULAR CLONING (1984); the series, METHODS IN ENZYMOLOGY (Academic Press, Inc.); VECTORS: A SURVEY OF MOLECULAR CLONING VECTORS AND THEIR USES (R.L. Rodriguez and D. T. Denhardt, eds., 1987, Butterworths); Sambrook et al. (1989), MOLECULAR CLONING, A LABORATORY MANUAL, second ed., Cold Spring Harbor Laboratory Press; Sambrook et al. (1989), MOLECULAR CLONING, A LABORATORY MANUAL, second ed., Cold Spring Harbor Laboratory Press; and Ausubel et al. (1995), SHORT PROTOCOLS IN MOLECULAR BIOLOGY, John Wiley and Sons.

The present invention is based in part on the discovery that an adenovirus protein, named Adenovirus Death Protein (ADP), could be advantageously overexpressed (expressed in larger amounts than with normal Ad5) in vectors whose replication is specifically targeted to cells expressing telomerase.

As described above, the present invention advantageously provides for replication-competent adenovirus vectors capable of replicating in cells expressing telomerase, preferably replication-restricted to such cells. The adenovirus vectors of the present invention overexpress ADP. The over-abundance of ADP results in lysis of the infected cells, infection of neighboring tumor cells, and eventually elimination of the whole tumor mass.

Replication of the adenovirus could be restricted to cells expressing telomerase without the loss of replication competence. Because E4 gene products are essential for Ad replication, placing their expression under the control of a tumor-specific promoter should restrict replication of the vector to cells in which the promoter is activated. Viruses with deleted E4 region are not viable. The E4 (early region 4) region of Ad5 is comprised of a set of genes, the products of which are involved in viral RNA processing, transcriptional activation and other processes. Viruses that lack the E4 genes can be propagated in cell culture using cell lines that stably express E4 proteins and therefore complement the virus. Either the E4ORF3 or E4ORF6 protein is sufficient for complementation. All E4 open reading frames (ORF's) are transcribed from a single promoter, located close to the right inverted terminal repeat (ITR) of the viral genome (Shenk, T. 1996. *Adenoviridae*: the viruses and their replication, p. 2111–2148. In B. N. Fields, D. M. Knipe, and P. M. Howley (eds.) *Fields Virology*. Lippincott-Raven, Philadelphia). The present invention retains the E4 function. Thus, the adenovirus vector could efficiently and specifically propagate in these cells without the need for complementation. Preferably, the vector restricts its expression to cells expressing telomerase.

Tissue-specific growth of an adenovirus vector can be achieved as demonstrated by the present inventors in pending U.S. application Ser. No. 09/351,778, incorporated by reference herein in its entirety. The present inventors have shown earlier that substitution of the E4 promoter for the SPB (Surfactant Protein B) promoter achieves tissue specific growth of the virus. The properties of the vector with this substitution, named KD1-SPB, have been published in a high quality peer-reviewed journal (Doronin, K., Kuppuswamy, M., Toth, K., Tollefson, A. E., Krajcsi, P., Krougliak, V., and Wold, W. S. M. Tissue-Specific, Tumor-Selective, Replication-Competent Adenovirus Vector for Cancer Gene Therapy. *J. Virol.* 75:3314–3324, 2001). In the present invention, the E4 promoter has been replaced with the human telomerase reverse transcriptase ('hTERT') promoter (SEQ ID NO. 3), thereby preferably restricting replication of the adenovirus to telomerase-expressing cells.

The present invention is based, in part, on the differential expression of telomerase between normal and neoplastic cells. DNA at chromosome ends is maintained in a dynamic balance of loss and addition of telomeric simple sequence repeats. Sequence loss occurs during cell replication, in part from incomplete replication of chromosome termini by DNA-dependent DNA polymerase. Telomeric repeat addition is catalyzed by the enzyme telomerase: a ribonucleoprotein enzyme which uses a short region within the RNA as a template for the polymerase reaction. Although cells can maintain a constant number of telomeric repeats by balancing repeat loss and addition, not all cells do so. Human germline and cancer cells maintain a constant number of telomeric repeats, while normal human somatic cells lose telomeric repeats with each cycle of cell division. Cells which do not maintain stable telomere length demonstrate a limited proliferative capacity; these cells senesce after a number of population doublings correlated with the erosion of telomeres to a critical minimum length.

Because normal somatic cells do not appear to express or require telomerase and do not maintain chromosome ends, and because all or almost all cancer cells express high levels of telomerase activity (see e.g. Koga S. et al., *Hum Gene Ther* 1; 11(10): 1397–406, 2000), the present invention, therefore, provides a recombinant adenovirus vector comprising a hTERT promoter that is replication-competent in cells expressing telomerase, preferably replication-restricted to such cells. Upon infection of a host, the adenovirus overcomes the replication machinery of the cell expressing telomerase and diverts the host's machinery to the synthesis of adenoviral RNA, DNA, and proteins. The adenoviral DNA and certain proteins will be assembled into virions within the cell, and the cell will lyse and release the virion particles. As most tumors express hTERT, this adenovirus vector will be a possible curative agent for the vast majority of human tumors. The adenovirus will be severely restricted in most normal cells that down regulate the activity of the telomerase promoter, thus not causing damage to them.

In one embodiment, the adenovirus vector comprises a gene that overexpresses ADP, that has expression of E4 genes under the control of the hTERT promoter, and has at least one inactivating mutation in the E3 region. To escape the host's immune surveillance, adenoviruses normally express E3, which disrupts antigen presentation by the MHC class I molecules and prevents early apoptosis of the viral-infected host. That disruption allows the virus to persist in the host for a longer period of time. By inactivating the E3 region of the adenovirus vector, the present inventors have removed this viral protective shield, allowing effective destruction and removal of the viral-infected cell by the host's immune system. In a preferred embodiment, the recombinant adenovirus vector of the present invention has a deletion that includes the genes for the Ad5, gp19K, RIDα, RIDβ, and 14.7K proteins in the E3 region. The precise nature of this deletion was described for the vector named KD3 (U.S. application Ser. No. 09/351,778; Doronin et al., *J Virol.* 74:6147–6155, 2000). The vectors named GZ3 and GZ3-TERT have this same deletion in the E3 region. In some examples to be presented later, the Ad5 mutant named dl309 was used as a control. dl309 lacks three genes in the E3 transcription unit (the genes for the RIDα, RIDβ, and 14.7K proteins), but retains and expresses other Ad5 genes, including that for ADP (Tollefson et al, 1996, J. Virol.). The gp19K, RIDα, RIDβ, and 14.7K proteins of the E3 region are not essential for Ad5 replication in cultured cells.

In a still further embodiment, the inventors recognize that neoplastic cells can not only express telomerase, but also enter S (synthesis) phase of the cell cycle on their own. Taking advantage of this characteristic of neoplastic cells, the current invention further limits replication of the vector named KD3-TERT to neoplastic cells by targeting cells that are in the S phase. The inventors have advantageously manipulated the E1A region to disrupt E1A's ability to interact with p300 and/or RB proteins, while not affecting its transactivation function. Without this interaction, E1A cannot promote cell progression from Go to S phase. For its replication, the adenovirus vector of the present invention would need enzymes and precursors of macromolecule synthesis that are abundant in cells only in the S phase of cell cycle. Most normal tissues in an adult human consist of resting (Go) cells. Neoplastic cells, in contrast, can enter S phase on their own. Accordingly, the adenovirus vector of the present invention targets neoplastic cells that enter S phase, while essentially bypassing normal resting cells.

The present invention also provides for a pharmaceutical composition comprising the adenovirus vector of the invention in association with a pharmaceutically acceptable carrier. While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

In addition, the present invention provides for methods and kits for promoting death of neoplastic cells by contacting said cells with an effective amount of vector(s) of the invention. For example, the inventors envisions that the vector would be injected at multiple sites in a solid tumor in a human patient. One example of a tumor would be a head and neck tumor. However, any type of solid tumor could be injected. The vector would come into contact with the tumor cells and would infect the cells in the normal way that adenovirus infects cells. The adenovirus early genes would be expressed, adenoviral DNA would replicate, adenoviral late genes would be expressed including the gene for ADP, and adenovirions would assemble. The cell would lyse and the adenovirus vector would be released from the cells. The vector would then infect other tumor cells and repeat the process. This process would continue to occur, with the vector spreading from cell to cell throughout the tumor. Preferably, all the cells in the tumor would be destroyed. Theoretically, the vector would be able to infect some non-cancerous cells in the body, and certain adenovirus early genes would be expressed. However, the E4 genes would not be expressed because their expression is controlled by the TERT promoter in the vector and the TERT promoter is not expressed in the vast majority of non-cancerous cells. Since the E4 genes are not expressed, vector DNA synthesis and late gene expression will not occur, and the non-cancerous cell will not be harmed.

Some non-cancerous cells, e.g. hematopoietic precursor cells, do express telomerase and, therefore, could be affected by the vector. However, hematopoietic cells are not infected efficiently by adenovirus, so it is expected that most hematopoietic cells will not be harmed by the vector.

Another use envisioned for the vectors is to inject them into the blood stream or into cavities, e.g. the peritoneal cavity, in which the tumor is located. As described above, the vector would infect and destroy the tumor cells but would spare the vast majority of non-tumor cells.

The inventors envision multiple therapeutic uses for the present invention. For example, the vector may be used in combination with radiation therapy for the treatment of cancer. The radiation therapy can be any form of radiation therapy used in the art such as for example, external beam radiation such as x-ray treatment, radiation delivered by insertion of radioactive materials within the body near or at the tumor site such as treatment with gamma ray emitting radionuclides, particle beam therapy which utilizes neutrons or charged particles and the like. In addition, use of more than one of the vectors of the present invention in a cocktail in combination with radiation therapy is also contemplated.

The inventors further contemplate use of the vector of the present invention in combination with chemotherapy as has been disclosed for other adenovirus vectors (U.S. Pat. No. 5,846,945). Chemotherapeutic agents are known in the art and include antimetabolites including pyrimidine-analogue and purine-analogue antimetabolites, plant alkaloids, antitumor antibiotics, alkylating agents and the like. The use of more than one of the vectors of the present invention with a chemotherapeutic agent or agents is also contemplated within this embodiment.

EXAMPLES

Example 1

Construction of KD3-TERT and GZ3-TERT.

This example illustrates the construction of GZ3-TERT and KD3-TERT anti-cancer vectors.

First, the inventors used the plasmid pK111 which contains the ADP overexpressing Ad GZ3 genome beginning from a BamHI site (nucleotide number 21256 in Ad5) to the right end of the genome. In pK111, the E4 promoter was deleted using a PCR-based technique, and a BstZ17I restriction site was inserted into the deletion, resulting in the plasmid pdlE4P. The resulting pdlE4P plasmid provides for easy replacement of the Ad E4 promoter with a foreign promoter. This plasmid will be a valuable tool for producing further vectors, where the E4 promoter will be substituted with a tumor specific promoter. Using pdlE4P, a DNA fragment containing the hTERT promoter sequence, flanked by BstZ17I sites (obtained by PCR amplification from human placental cells genomic DNA), was cloned into this newly created restriction site, resulting in plasmid pdlE4TERT. This plasmid was co-transfected into 293 E4 cells together with EcoRI (nucleotide number 27331 in Ad5) cut dl 1101/1107 or dl327 DNA, resulting in KD3-TERT (SEQ ID NO. 1) or GZ3-TERT (SEQ ID NO. 2), respectively, via homologous recombination of overlapping DNA sequences. The Ad5 mutants named dl 1101/1107 (also referred to as dl01/07) and dl327 were described in U.S. application Ser. No. 09/351,778 and that application describes the general method of constructing the vectors KD3 and GZ3. Mutant dl1101/1107 has the same two small deletions in the E1A gene as do the vectors named KD3 and KD3-TERT. When EcoRI cleaves dl 1101/1107 DNA, a large fragment is produced comprising approximate adenovirus map units 0–59. Again, this fragment contains the small E1A deletions. In the method to construct KD3-TERT as described above, this large fragment undergoes homologous recombination with plasmid pdlE4TERT. Mutant dl327 has wild type (normal, non-mutated) Ad5 sequences in the region from DNA map positions 0–59. As is the case with dl1101/1107 DNA, when EcoRI cleaves dl327 DNA, the fragment comprising map position 0–59 is generated. In the method to construct GZ3-TERT as described above, this fragment undergoes homologous recombination with the plasmid pdlE4TERT. Plaques expected to be KD3-TERT or GZ3-TERT were picked, and selected plaques were expanded in 293 E4 cells. Viral DNA was extracted from these cells and examined by restriction endonuclease digestion and the polymerase chain reaction for the anticipated E1A mutation (KD3-TERT), E3 deletion and ADP gene presence, and the TERT promoter. One plaque of KD3-TERT and one plaque of GZ3-TERT with the correct properties was plaque purified three times, then grown up to high titers and purified by isopicnic centrifugation. All the methods used are known to a person of ordinary skill in the art.

GZ3-TERT has wild-type E1A; its selective replication relies on the tumor selective activity of the hTERT promoter. KD3-TERT, on the other hand, has deletions in the E1A gene, which offer an additional level of safety. The overexpression of ADP in both vectors will improve the oncolytic properties of the virus.

Example 2

Assays for Cytopathic Effect caused by GZ3-TERT and KD3-TERT.

This example illustrates the ability of GZ3-TERT to replicate within and destroy SW480 adenocarcinoma (colorectal, human) cells.

Various cell lines were grown to about 60–70% confluency in 35 mm Petri dishes. The cells were infected at a multiplicity of 10 pfu/cell with dl309, GZ3 or GZ3-TERT. pfu refers to plaque forming units, i.e. units of infectious vector. The monolayers were visualized by phase contrast microscopy and photographed at certain time points post infection.

The ability of GZ3-TERT to grow within and destroy cancer cells was compared to that of GZ3 and "wild-type" adenovirus by several methods in a variety of human cancer cell lines. As described earlier, and in U.S. application Ser. No. 09/351,778, GZ3 has wild type Ad5 E1A and a large deletion in the E3 region that removes the genes for the ADP, gp19K, RIDα, RIDβ, and 14.7K proteins. The adp gene has been reinserted into the E3 region in such a manner that the ADP protein is overexpressed at late stages of infection. GZ3 has a wild type Ad5 E4 promoter. GZ3-TERT is the same as GZ3, except it has the E4 promoter replaced by the TERT promoter. The Ad5 mutant dl309 serves as the "wild-type" adenovirus control. Mutant dl309 lacks three genes in the E3 transcription unit (the genes for the RIDα, RIDβ, and 14.7K proteins), but retains and expresses other Ad5 genes including that for ADP (Tollefson et al., *J. Virol.* 70:2296–2306, 1996). ADP is synthesized at normal levels, i.e. levels similar to that of Ad5.

Figure 2A:
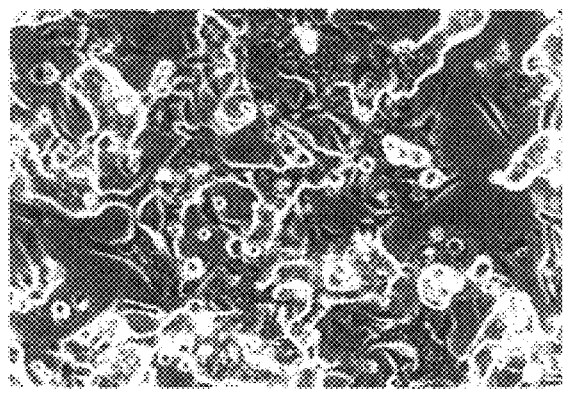
Figure 2B:
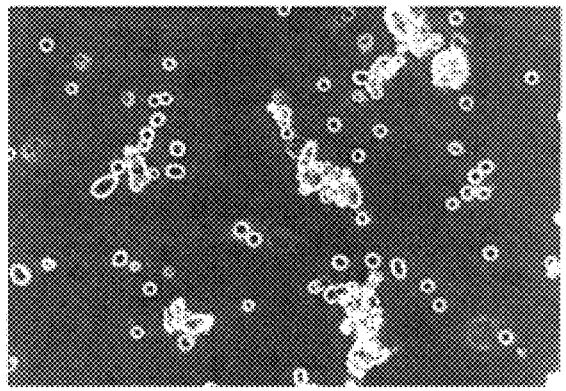
Figure 2C:
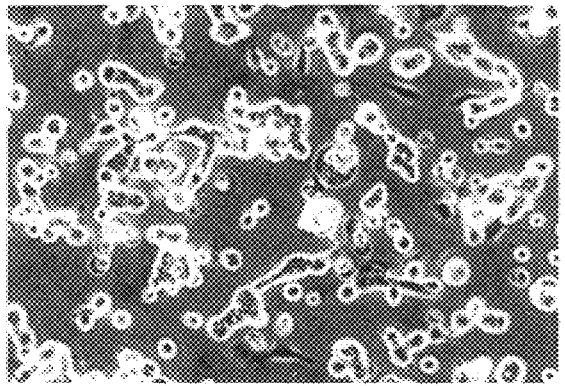

FIG. 2 shows the cytopathic effect (CPE) induced by GZ3-TERT and GZ3 in SW480 cells. CPE is considered to be a strong indicator of virus replication and cell death. Cells growing in monolayers were infected with 10 plaque forming units (pfu) per cell of GZ3-TERT or GZ3, and were visualized by phase contrast microscopy and then photographed. With the mock infection, the cells appeared as a disorganized nearly complete monolayer (FIG. 2A). With the GZ3 infection, the cells had rounded up, shrunk, and detached, and nearly all the cells appeared lysed (FIG. 2B). With the GZ3-TERT infection, most of the cells had rounded up and detached (FIG. 2C). These results indicate that both GZ3 and GZ3-TERT replicate in SW480 cells. The CPE seen with GZ3-TERT was not quite as pronounced as that seen with GZ3, suggesting that the time course of infection with GZ3-TERT is slightly delayed compared to GZ3. Nevertheless, despite the substitution of the E4 promoter with hTERT promoter, GZ3-TERT replicates very well in SW480 cells. This conclusion is consistent with other experiments described below.

Figure 3A:
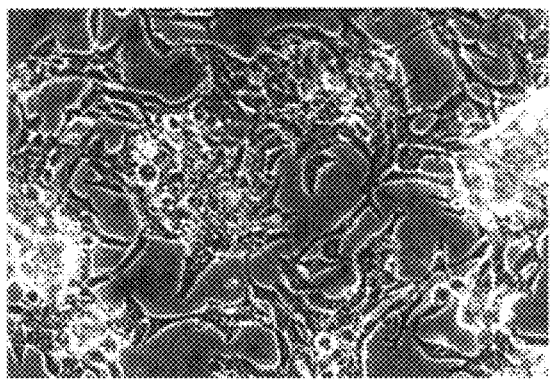
Figure 3B:
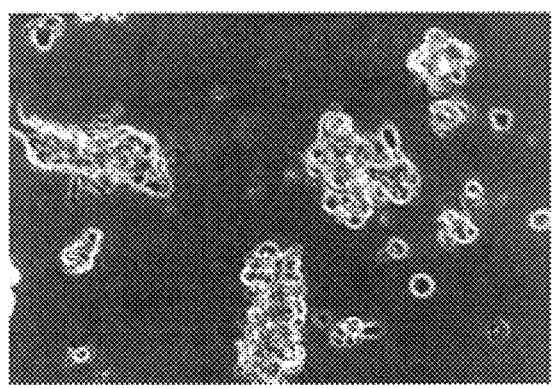
Figure 3C:
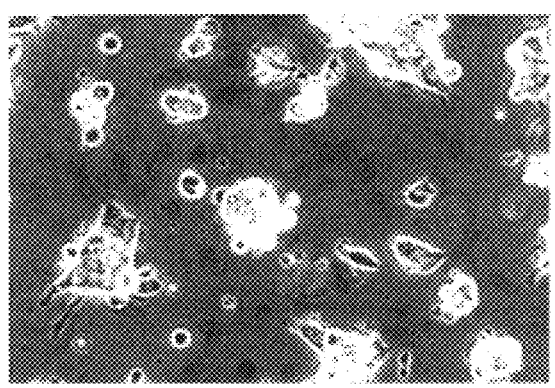

FIG. 3 shows the CPE induced by these vectors in LNCaP carcinoma (prostate, human) cells. As with the SW480 cells, the mock-infected cells appeared as a disorganized monolayer (FIG. 3A). The GZ3-infected cells had rounded up, shrunk, and detached, and nearly all the cells appeared lysed (FIG. 3B). The GZ3-TERT-infected cells were also rounded up and detached with a large number of cells appearing lysed (FIG. 3C), but the CPE was not as extensive as that seen with GZ3. These results indicate that GZ3-TERT also replicates in LNCaP cells, although not quite as efficiently as does GZ3.

Example 3

Assay to Measure Cell Viability After Virus Infection.

The Trypan blue exclusion assay was used to compare the cell destroying effect of GZ3-TERT vs. GZ3 on cancer cells. At the end of the virus replication cycle, cells die and their membranes become porous. Trypan blue enters those cells with a porous cell membrane.

Various cell lines were grown to about 60–70% confluency in 35 mm Petri dishes. Cells growing in monolayers were either mock-infected or infected at a multiplicity of 10 pfu/cell with dl309, GZ3 or GZ3-TERT. Cells were trypsinized at 5 or 10 days post infection, and stained with Trypan blue. Approximately 400 cells were counted in a hemacytometer, and ratios of stained and unstained cells were calculated for each sample.

Figures 4A, 4B:
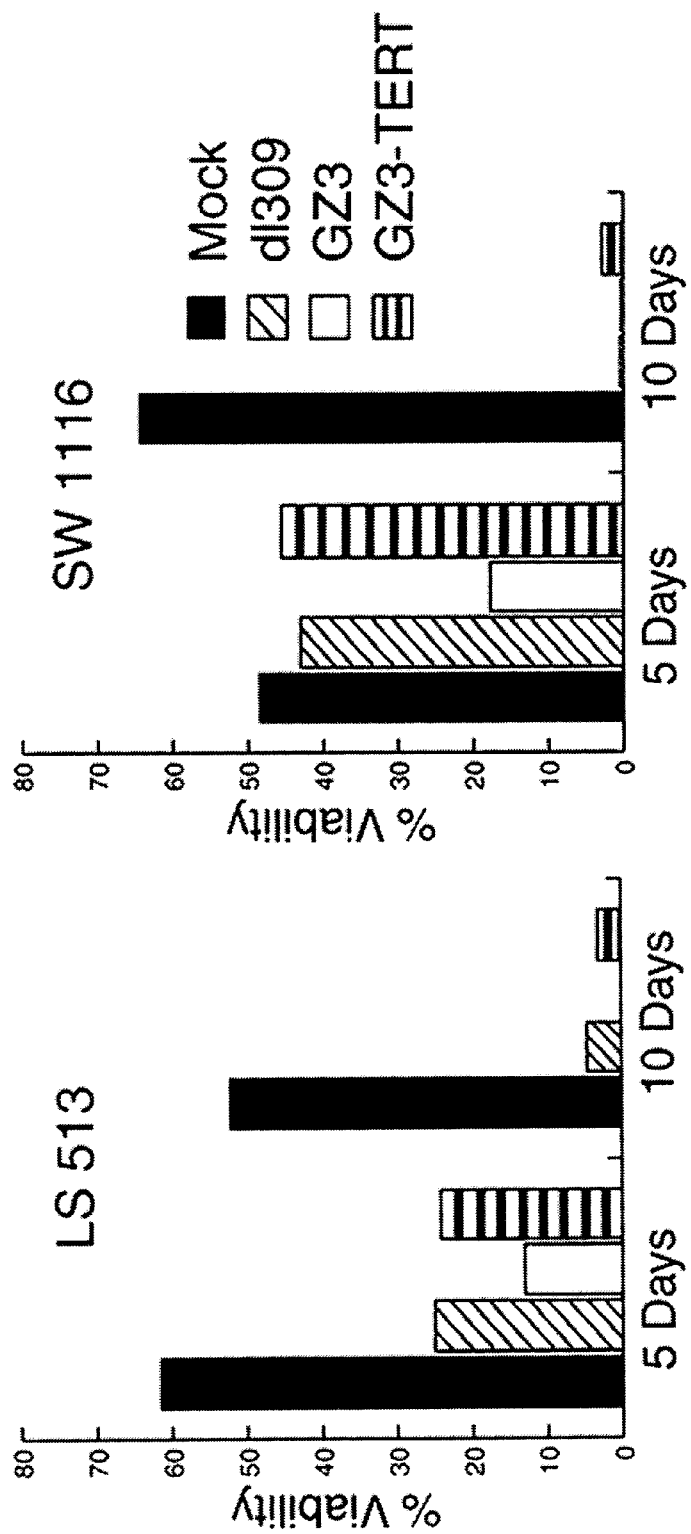

FIG. 4A shows the percentage of viable cells remaining at 5 and 10 days after LS513 carcinoma (cecum, human) cells were infected with mock (i.e. were mock-infected), dl309, GZ3, or GZ3-TERT. Approximately 62% of the mock-infected cells were viable at 5 days post infection as compared to 25% of the dl309-infected cells, 13% of the GZ3-infected cells, and 24% of the GZ3-TERT-infected cells. At 10 days postinfection, 52% of the mock-infected cells were viable, approximately 5% of the d1309-infected cells were viable, no GZ3-infected cells were viable, and only 3% of GZ3-TERT-infected cells remained viable. These results indicate that GZ3-TERT kills LS513 cells at approximately the same rate as does dl309. This very important result attests to the potency of GZ3-TERT because, as discussed above, dl309 is the "wild-type" Ad5 control. Stated another way, GZ3-TERT is as effective as wild-type Ad5 in killing LS513 cancer cells. Cell death is associated with virus replication and late gene expression (including ADP expression at late stages of infection). Although GZ3-TERT was as effective as dl309 killing LS513 cells, it was not as effective as GZ3.

FIG. 4B shows the percentage of viable SW1116 adenocarcinoma (colon, human) cells remaining at 5 and 10 days postinfection with mock, dl309, GZ3, or GZ3-TERT. With the mock infection, 46% of the cells were viable after 5 days. With the dl309 infection, 43% of the cells were viable after 5 days. With the GZ3 infection, 18% of the cells were viable after 5 days. With the GZ3-TERT infection, 46% of cells were viable after 5 days. At 10 days postinfection, 64% of the mock-infected cells were viable, less than 1% of either the dl309 or GZ3-infected cells were viable, and 3% of the GZ3-TERT-infected cells were viable. The results demonstrate that, as was the case with the LS513 cells, GZ3-TERT kills SWI 116 cells as well as dl309, although not as efficiently as GZ3.

Figures 4C, 4D:
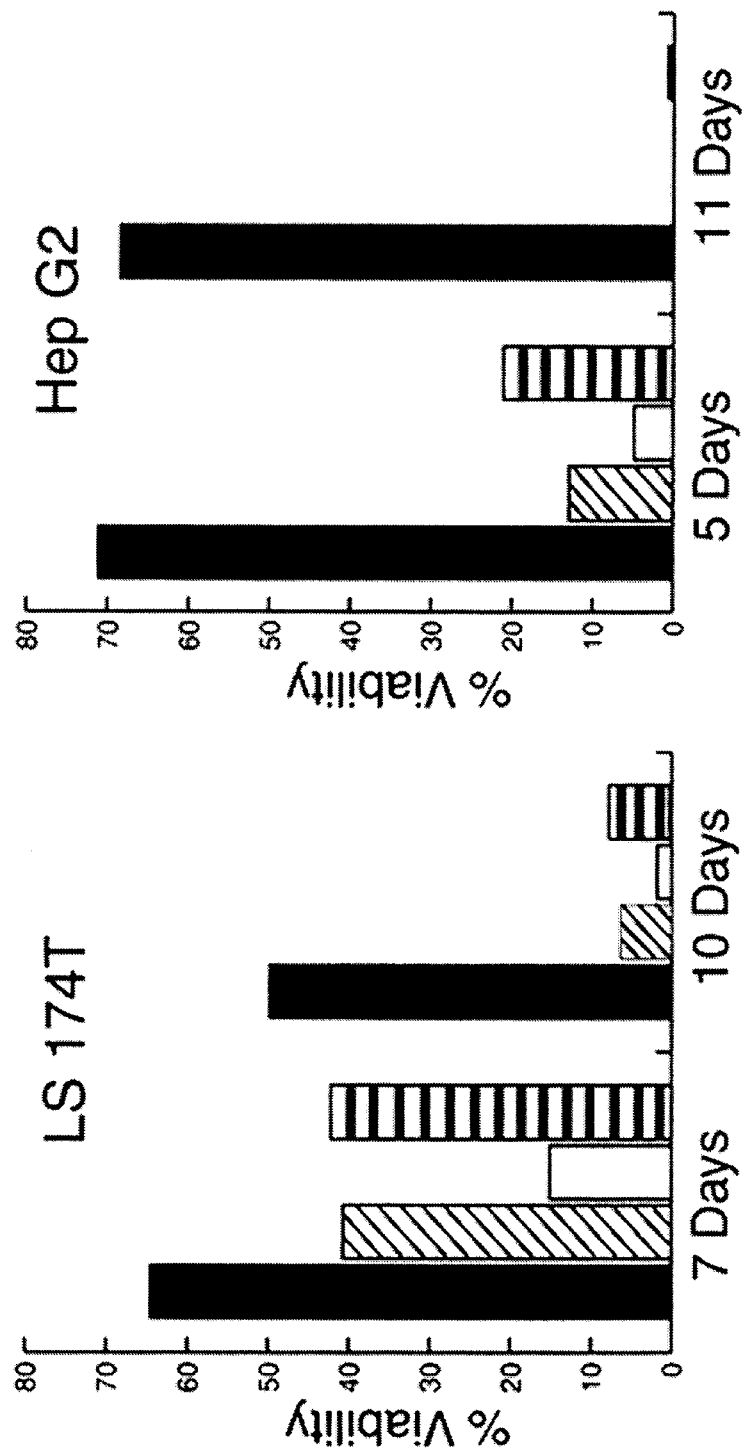

FIG. 4C shows the percentage of viable LS 174T adenocarcinoma (colorectal, human) cells remaining at 7 and 10 days postinfection with mock, dl309, GZ3, or GZ3-TERT. After 7 days, approximately 65% of mock-infected cells were viable, 41% of dl309-infected cells were viable, 15% of GZ3-infected cells were viable, and 42% of GZ3-TERTinfected cells were viable. At 10 days postinfection, 50% of mock-infected cells remained viable, 6% of dl309-infected cells remained viable, 2% of GZ3-infected cells remained viable, and 8% of GZ3-infected cells remained viable. Again, these results indicate that GZ3-TERT kills LS 174T cells as well as does dl309, although not as efficiently as GZ3.

FIG. 4D shows the percentage of viable HepG2 hepatocellular carcinoma (human) cells remaining at 5 and 11 days post-infection with mock, dl309, GZ3, or GZ3-TERT. With the mock infection, 71% of the cells were viable after 5 days. With the dl309, GZ3, and GZ3-TERT infections, 13%, 5%, and 21%, respectively, of the cells were viable after 5 days. At 11 days postinfection, 69% of mock-infected cells were viable and less than 1% of GZ3-TERT-infected cells were viable. There were no dl309 or GZ3-infected cells viable at 11 days postinfection. These results indicate that GZ3-TERT kills HepG2 cells as well as does dl309. Interestingly, GZ3-TERT killed these cells nearly as well as GZ3.

Figures 4E, 4F:
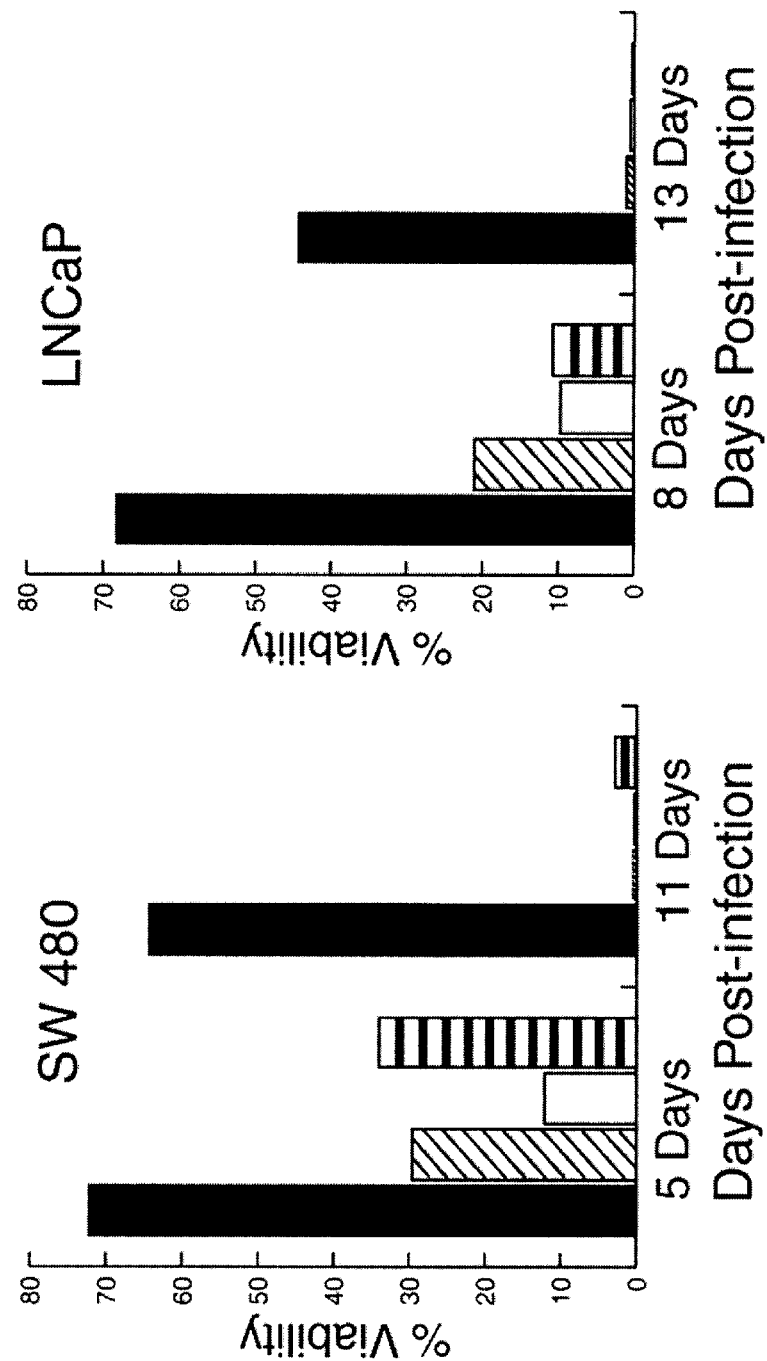

FIG. 4E shows the percentage of viable SW480 colon cancer cells remaining at 5 and 11 days post-infection with mock, dl309, GZ3, or GZ3-TERT. At 5 days post-infection, approximately 72% of the mock-infected cells were viable, 30% of the dl309-infected cells were viable, 12% of the GZ3-infected cells were viable, and 34% of the GZ3-TERT cells were viable. At 11 days postinfection, 64% of the mock-infected cells remained viable, less than 1% of the dl309- or the GZ3-infected cells remained viable, and 3% of the GZ3-TERT-infected cells remained viable. This resembles the phase contrast results described earlier: GZ3-TERT kills SW480 cancer cells, but not as efficiently as GZ3. Importantly, however, GZ3-TERT kills cells as well as does dl309.

FIG. 4F shows the percentage of viable LNCaP prostate cancer cells remaining at 8 and 13 days postinfection with mock, dl309, GZ3, or GZ3-TERT. With the mock infection, 68% of the cells were viable after 8 days. With the dl309, GZ3, and GZ3-TERT infections, 21%, 10%, and 11%, respectively, of the cells were viable after 8 days. At 13 days postinfection, 44% of the mock-infected cells were viable, 1% of the dl309-infected cells were viable, and less than 1% of either the GZ3- or the GZ3-TERT-infected cells were viable. These results indicate that similar to the phase contrast microscopy results discussed previously, GZ3-TERT kills as efficiently as GZ3 in LNCaP cancer cells. GZ3-TERT kills LNCaP as well or better than does dl309.

Figure 5A:
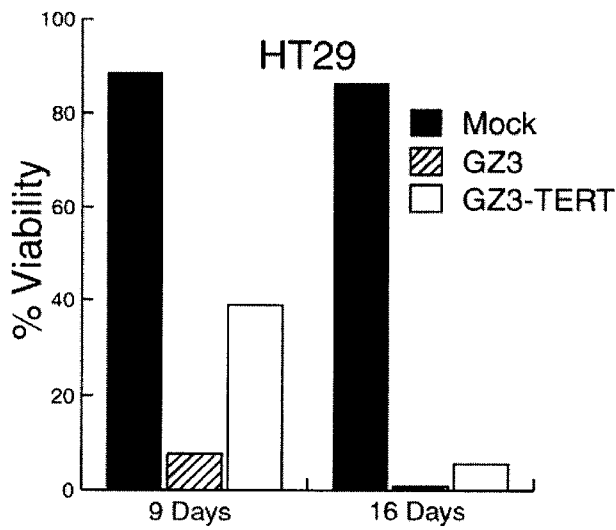
Figure 5B:
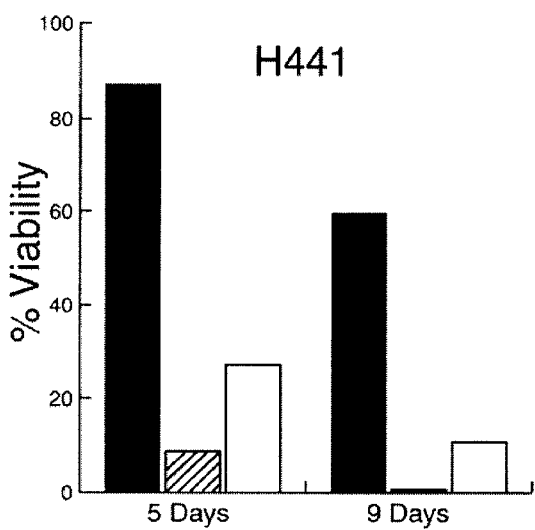
Figure 5C:
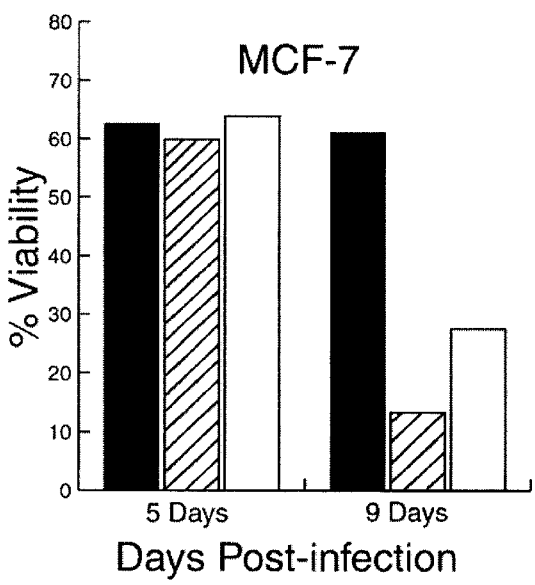

FIGS. 5A, 5B, and 5C show the results of a Trypan blue exclusion assay on additional cancer cell lines that were either mock-infected or infected with 10 pfu per cell of GZ3 or GZ3-TERT. FIG. 5A shows the percentage of viable HT29 adenocarcinoma (colon, human) cells remaining at 9 and 16 days postinfection. With the mock infection, 89% of the cells were viable after 9 days. With the GZ3 infection, 8% of the cells were viable after 9 days. With the GZ3-TERT infection, 39% of the cells were viable after 9 days. At 16 days postinfection, 86% of the mock-infected cells remained viable, less than 1% of the GZ3-infected cells remained viable, and 6% of the GZ3-TERT-infected cells remained viable. These results indicate that both GZ3-TERT and GZ3 kills HT29 cells.

FIG. 5B shows the percentage of viable NCI-H441 bronchioalveolar carcinoma (human, lung) cells remaining at 5 and 9 days postinfection with mock, GZ3, or GZ3-TERT. At 5 days postinfection, approximately 87% of mock-infected cells, 9% of GZ3-infected cells, and 27% of GZ3-TERT-infected cells were viable. At 9 days postinfection, 60% of mock-infected cells, less than 1% of GZ3-infected cells, and approximately 11% of GZ3-TERT-infected cells remained viable. These results indicate that GZ3-TERT kills H441 cells, but not as efficiently as GZ3.

FIG. 5C shows the percentage of viable MCF-7 adenocarcinoma (breast, human) cells remaining at 5 and 9 days postinfection with mock, GZ3, or GZ3-TERT. At 5 days postinfection, 63%, 60%, and 64% of the mock-, GZ3-, and GZ3-TERT-infected cells, respectively, were viable. At 9 days postinfection, 61% of the mock-infected cells, 13% of the GZ3-infected cells, and 27% of the GZ3-TERT-infected cells were viable. These results indicate that both GZ3-TERT and GZ3 show delayed killing in MCF-7 cells.

FIG. 6 shows the results of a Trypan blue exclusion assay on yet another cancer cell line, Hep3B (hepatocellular carcinoma, human) cells. Cells growing in monolayers were mock-infected or infected with 10 pfu per cell of GZ3 or GZ3-TERT. With the mock infection, 83% of the cells were viable after 5 days. With the GZ3 and GZ3-TERT infections, 4% and 18% of cells, respectively, were viable after 5 days. These results indicate that GZ3-TERT kills Hep3B cells, but not as efficiently as GZ3.

Example 4

Immunofluorescence Staining.

The purpose of this example is to show that GZ3 and GZ3-TERT both express the Ad5 E1A, E4ORF3, DNA binding protein (DBP), and fiber proteins in various cancer cell lines. The E1A protein should be expressed in all cells regardless of whether the vector replicates. This is also true for DBP, whose synthesis is induced by the E1A proteins. However, the E4ORF3 protein should only be expressed when the TERT promoter is active. This is also true for the fiber protein which is only expressed at late stages of infection after the E4 proteins have been expressed and the vector DNA has replicated.

Various cell lines were grown to about 60–70% confluency on Corning no. 1 coverglasses in 35 mm Petri dishes. The cells were infected at a multiplicity of 10 pfu/cell with dl309, GZ3 or GZ3-TERT in duplicate. At approximately 2 days postinfection, cells were fixed in 4% paraformaldehyde in PBS, and then permeabilized with methanol at −20° C. After rehydration in PBS, cells were incubated with (A) primary antibodies against the Ad5 E1A protein (mouse monoclonal antibody) or the Ad5 E4ORF3 protein (rabbit antiserum) or, on parallel coverslips, (B) primary antibodies against the Ad5 DBP (rabbit antipeptide antiserum) or against the Ad5 fiber protein (mouse monoclonal antibody). Cells were washed and incubated with secondary antibodies (goat anti-rabbit IgG-FITC conjugate and goat anti-mouse IgG-RITC conjugate) to visualize expression and localization of the Ad5 proteins. Photographs were taken on a Nikon epifluorescence microscope using a 100X Planapo lens and TMAX 400 film (Kodak).

FIGS. 7 and 8 show viral proteins made during virus replication in HeLa epithelioid carcinoma (cervix, human) cells. FIGS. 7A and 7B demonstrate the presence of the Ad E1A proteins in both GZ3-infected cells and GZ3-TERT-infected cells. E1A proteins are the initial proteins made after virus infection and are necessary for the production of the other Ad early proteins, such as the DBP and E4ORF3 proteins. FIGS. 7C and 7D show the expression of the E4ORF3 protein in both the GZ3 and the GZ3-TERT-infected cells. The presence of E4ORF3 proteins in the GZ3-TERT-infected cells demonstrates a sufficient amount of TERT promoter activity in HeLa cells to allow expression of the E4 transcription unit. FIGS. 8A and 8B show the presence of DBP in both GZ3 and GZ3-TERT-infected cells. Although DBP is made at early stages of infection independently of E4 expression, much more DBP is made at late stages of infection following E4 expression and vector DNA replication. Thus, the abundant quantities of DBP seen in FIGS. 8A and 8B suggests that the vectors were able to undergo replication. FIGS. 8C and 8D show the existence of the late protein called fiber which is produced from the major late transcription unit. Transcription of the major late region is only possible after viral DNA replication. Thus, the presence of fiber in both GZ3 and GZ3-TERT-infected cells indicates that viral replication had occurred.

FIGS. 9 and 10 show Ad proteins produced during virus replication in A549 lung carcinoma (human) cells infected with GZ3 or GZ3-TERT. FIGS. 9A and 9B show that the E1A proteins were made. FIGS. 9C and 9D show that the E4ORF3 protein was made. It appears that the amount of the E4ORF3 protein produced in the GZ3-infected cells may be greater than the GZ3-TERT-infected cells, however, the amount of TERT promoter activity in A549 cells is sufficient to allow expression of the E4 transcription unit. FIGS. 10A and 10B show that the E2 protein DBP was made in both GZ3 and GZ3-TERT-infected cells. FIGS. 10C and 10D show the presence of the fiber protein. It appears that there may be more fiber protein present in the GZ3-infected cells than the GZ3-TERT-infected cells. Nevertheless, and more importantly, because the fiber protein is made after viral DNA replication, its presence indicates that GZ3-TERT replicates in A549 cells.

FIGS. 11 and 12 show proteins made during virus replication in Hep3B liver cancer cells infected with GZ3 or GZ3-TERT. FIGS. 11A and 11B show that the E1A proteins were made in both GZ3 and GZ3-TERT-infected cells. FIGS. 11C and 11D show that the E4ORF3 protein was made in both GZ3- and GZ3-TERT-infected cells. FIGS. 12A and 12B show that the protein DBP was made in both GZ3- and GZ3-TERT-infected cells. FIGS. 12C and 12D show the presence of the fiber protein in both the GZ3 and GZ3-TERT-infected cells. Again, the presence of the fiber protein indicates that GZ3 and GZ3-TERT replicate in Hep3B cells.

Example 5

Virus Spread Assays.

An additional method to compare the ability of GZ3-TERT, dl309, and GZ3 to replicate in and destroy cells is the virus spread assay. This assay measures not only the ability of the vector to replicate in cells, but also its ability to spread from cell to cell at low multiplicities of infection (low pfu/cell) (Doronin et al., *J Virol.* 74:6147–6155, 2000). That is, for example, if only one in ten or one in one hundred cells were initially infected, destruction of the monolayer would not be observed unless the vector replicated in the original cell, lysed it, spread to other cells, replicated in these cells, and lysed these cells.

A549, SW480, and LS513 cells were grown to 70 to 80% confluency in 48 well plates. These cell lines, growing in monolayers, were either mock-infected or infected with various multiplicities (serial dilutions ranging from $10^2$ to $10^{-4}$ pfu/cell) of dl309, GZ3, or GZ3-TERT in duplicate. The cells were stained with crystal violet dye (1% crystal violet, 10% formaldehyde, 20% methanol) at 7 or 10 days post infection, or 12 or 13 days post infection, depending on the cell line. The crystal violet stain was aspirated from the cell surface after 15 minutes and the plates were washed. Cells attached to the surface stained blue.

Figure 10A:
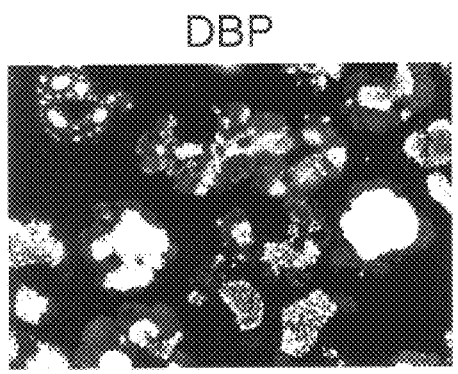
Figure 10B:
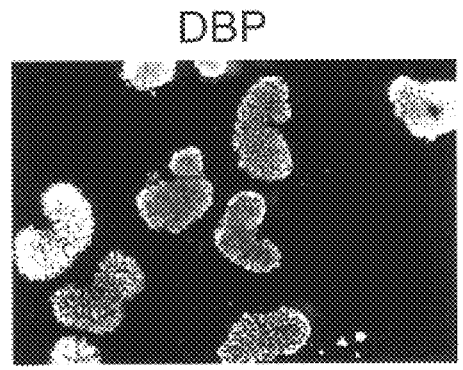
Figure 10C:
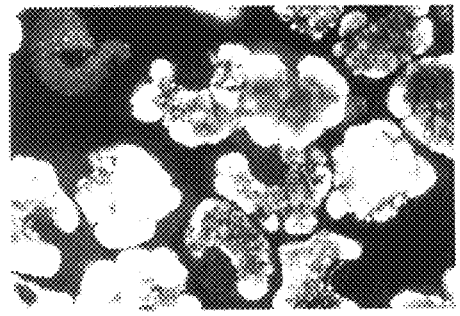
Figure 10D:
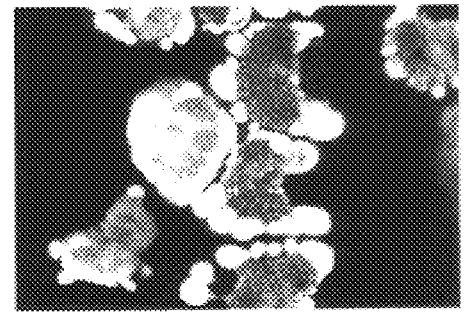
Figure 11A:
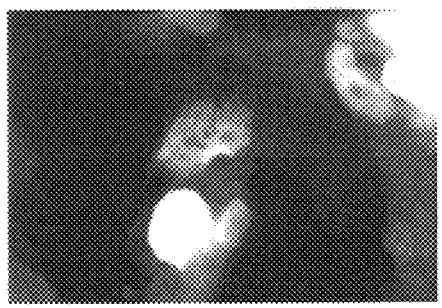
Figure 11B:
Figure 11C:
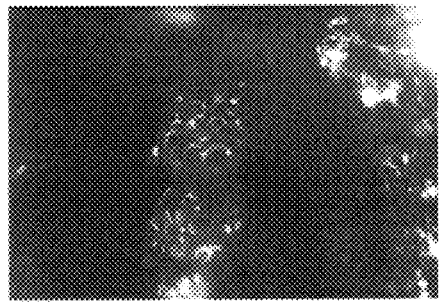
Figure 11D:
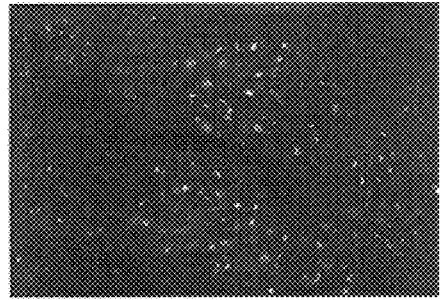
Figure 12A:
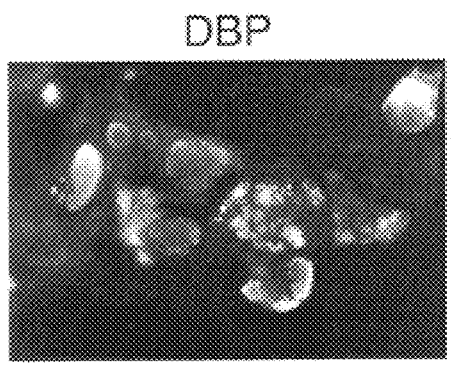
Figure 12B:
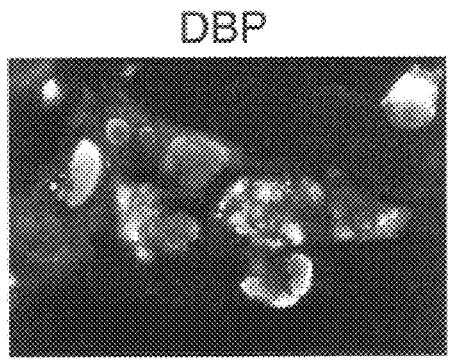
Figure 12C:
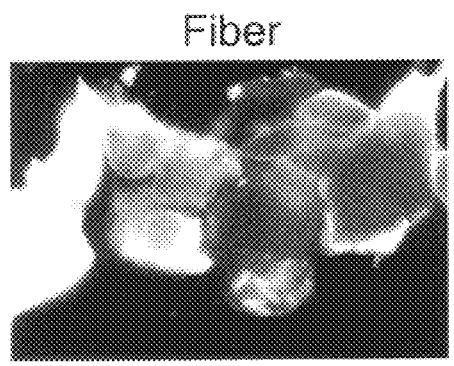
Figure 12D:
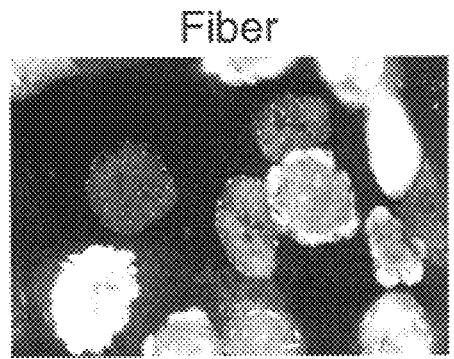

FIG. 13 shows A549, SW480, and LS513 cancer cells at 7 days postinfection. FIG. 10A shows that GZ3-TERT, dl309, and GZ3 killed A549 cells with equal efficiency at $10^1$ pfu/cell initial infection. At $10^0$ pfu/cell infection, GZ3-TERT and GZ3 were equally efficient in killing A549 cells; dl309, however, killed with slightly less efficiency. At $10^{-1}$ pfu/cell infection, only GZ3 appeared to efficiently kill cells, and at $10^{-2}$ pfu/cell or less, GZ3 was also not able to destroy A549 cells. At 10 days postinfection, GZ3-TERT, dl309, and GZ3 were equal in their ability to kill A549 cells between $10^1$ and $10^{-1}$ pfu/cell initial infection. Between $10^{-2}$ and $10^{-3}$ pfu/cell infection, GZ3-TERT and dl309 were less efficient at killing than GZ3. At $10^{-4}$ pfu/cell, only GZ3 was efficient in killing A549 cells. Importantly, GZ3-TERT was at least as effective as dl309, indicating that GZ3-TERT grows and spreads from cell to cell as well as does wild type Ad5. GZ3 was more efficient at killing and spreading than dl309 demonstrating that vectors that overexpress ADP have enhanced ability to kill cells and spread from cell to cell as compared to wild type Ad5. These same results and conclusions were seen and derived with the SW480 and LS513 cells as described below.

Figure 13B:
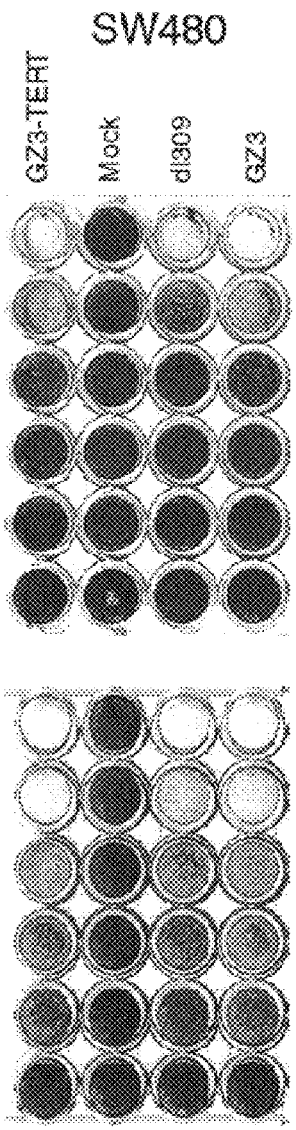

FIG. 13B shows that SW480 colon cells were also killed by GZ3-TERT, dl309, and GZ3 at 7 days postinfection. GZ3-TERT, dl309, and GZ3 appeared to be equally efficient at killing cells infected with $10^1$ pfu/cell; however, at $10^0$ pfu/cell infection, dl309 appeared slightly less efficient than GZ3-TERT or GZ3. At $10^{-1}$ pfu/cell or less, neither GZ3-TERT, dl309, nor GZ3 appeared to kill cells efficiently. At 10 days postinfection, GZ3-TERT, dl309, and GZ3 appeared equal in their ability to kill SW480 cells at $10^1$ pfu/cell. At an initial infection of $10^0$ pfu/cell or less, GZ3-TERT and GZ3 appeared to be more efficient than dl309 in killing SW480 cells.

Figure 13C:
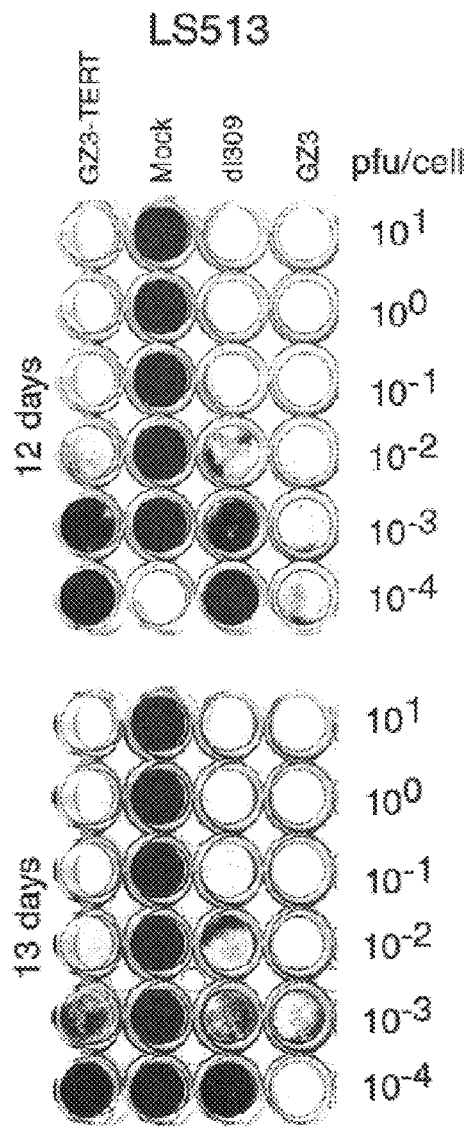

FIG. 13C shows that GZ3-TERT, dl309, and GZ3 were all very efficient at killing LS513 colon cancer cells at 7 and 10 days postinfection. At initial infections between $10^1$ and $10^{-1}$, GZ3-TERT, dl309, and GZ3 were equally efficient at killing cells at 7 days postinfection. However, at $10^{-2}$ pfu/cell, dl309, and GZ3-TERT appeared to be slightly less efficient than GZ3 in killing LS513 cells. At $10^{-3}$ pfu/cell or less, only GZ3 appeared to efficiently kill cells. At 10 days postinfection, GZ3-TERT and GZ3 were equal in their efficiency to kill LS513 cells between $10^1$ and $10^{-2}$ pfu/cell infection, with dl309 showing slightly less efficiency. At initial infections of $10^{-3}$ pfu/cell or less, GZ3 appeared more efficient than either dl309 or GZ3-TERT in killing LS513 cells.

Again, one important conclusion from these experiments is that GZ3-TERT is as effective as wild type Ad5 in replicating in cells and spreading from cell to cell. Since wild type Ad5 (or dl309) cannot (at present) be used for cancer therapy, and since the replication of GZ3-TERT is restricted to cancer cells expressing telomerase, GZ3-TERT should be an effective and practical vector to treat human cancer.

Example 6

Single-step Growth Curves.

The next series of experiments shows that GZ3-TERT replicates to the same quantity and at the same rate as Ad5 or GZ3 in three different cancer cell lines. Stated another way, the experiments show that if every cell in the culture dish is infected at the start of the experiment, approximately the same amount of progeny virus is produced in the culture dish, and at approximately the same rate.

A549, DU145, and SW480 cells were grown to about 60–70% confluency in 35 mm Petri dishes. The cells were infected at a multiplicity of 10 pfu/cell with dl309, GZ3 or GZ3-TERT (8 dishes per virus). After an hour, cells were washed with medium three times to clear away any non-attached virus. Complete medium (2 ml) was added back to the dishes. One dish was frozen from each set of eight at this time, and then every day for 7 consecutive days. The cells were freeze-thawed three times, and then the lysates were cleared up by low-speed centrifugation. The virus yield was determined by titering the supernatants on 293E4 cells.

To determine whether GZ3-TERT grows as well as Ad5 and/or GZ3, DU145 carcinoma (prostate, human) cells, A549 lung cancer cells and SW480 colon cancer cells were infected with 10 pfu per cell of these viruses for 1 hr. Cells were washed and harvested immediately to provide a zero time point and then daily for 7 days. The harvested cells were lysed and titered on 293-E4 cells. FIG. 14 shows the virus yield in DU145 cells of GZ3-TERT, GZ3, and Ad5 titered on 293E4 cells. By day 3 postinfection, the titer of all viruses was similar. This result indicates that while GZ3-TERT may initially be slightly slower growing than Ad5 and GZ3, at 3 days postinfection, the amount of GZ3-TERT produced was equivalent to Ad5 and GZ3.

FIG. 15 shows the virus yield in A549 lung cancer cells of GZ3-TERT, GZ3, and Ad5 titered on 293E4 cells. At 3 days postinfection, it appeared that the virus titer of GZ3-TERT, GZ3, and Ad5 was similar. As with DU145 cells, GZ3-TERT may initially be slower growing than Ad5 or GZ3, but the amount of GZ3-TERT at 3 days postinfection was equivalent to Ad5 or GZ3.

FIG. 16 shows the virus yield in SW480 colon cancer cells of GZ3-TERT, GZ3, and Ad5 titered on 293E4 cells. At 2 days postinfection, GZ3-TERT grew at a rate similar to that of Ad5 or GZ3. The final amount of GZ3-TERT produced was slightly lower than that with Ad5 and GZ3, but it was still very significant.

Example 7
KD3-TERT will Replicate in Cancer Cells.

The vector named KD3 was described in U.S. application Ser. No. 09/351,778 and in Doronin et al. (*J. Virol.* 74:6147–6155, 2000). KD3 has two small deletions in the E1A gene that restrict the replication of KD3 to cancer cells. In fact, KD3 grows well on most cancer cell lines tested (Doronin et al., *J Virol.* 74:6147–6155, 2000). The examples presented for GZ3-TERT show that the E4 promoter can be replaced by the TERT promoter without seriously compromising the ability of the vector to replicate in cancer cells. The vector named KD3-TERT has the same E4 promoter deletion and TERT promoter substitution as GZ3-TERT. The inventors tested the ability of KD3-TERT to replicate in neoplastic cell lines in a series of experiments as described in Examples 1–6 and 8, substituting KD3-TERT for GZ3-TERT. In one experiment, a series of dishes of A549 cells are mock-infected or infected with 10 pfu/cell of KD3-TERT and KD3. Cells are washed, and the cells are collected, one dish of mock, KD3, and KD3-TERT infected cells, and frozen. Cells are similarly collected and frozen each day from day 1 to day 8 following infection. Cells are freeze-thawed three times, and the virus released is titered on 293 E4 cells. For both KD3-TERT and KD3, there is a similar increase in titer at days 1, 2, and 3, reaching a plateau of about $10^8$ pfu after 3 days. The results show that KD3-TERT replicates to approximately the same amount and at approximately the same rate as does KD3.

Example 8
KD3-TERT and GZ3-TERT is Replication-restricted to Neoplastic Cells Expressing Telomerase.

The present inventors envision that GZ3-TERT and KD3-TERT will be replication-restricted to neoplastic cells expressing telomerase. Primary human cells are a good model for normal cells in the body. First, KD3 does not grow (or grows very poorly) in human primary cells. The cells specifically examined were human bronchial epithelial cells, human small airway epithelial cells, and human endothelial cells (Doronin et al., 2000). Since KD3-TERT has the same E1A gene deletion as does KD3, the inventors expect that KD3-TERT will not replicate in primary human cells.

Second, primary human cells are not expected to express telomerase. Therefore, the inventors further predict that KD3-TERT will also be unable to replicate in primary human cells, not only because of the E1A gene mutation, but also because of the E4-TERT promoter substitution. Similarly, the inventors further predict that GZ3-TERT will not be able to replicate (or will replicate very poorly) in primary human cells, because again, replication depends on the ability of the TERT promoter.

These predictions with KD3-TERT and GZ3-TERT in primary cells are tested using methods similar to those described in Doronin et al. (2000). Primary human cells are purchased, placed in tissue culture, and expanded by minimal passages. Cells in culture are mock-infected or infected with KD3-TERT, GZ3-TERT, KD3, GZ3, dl1101/1107, or Ad5 (or dl309), and studies similar to those described in Examples 1–6 are conducted. Human primary bronchial epithelial cells in multiple dishes are mock-infected or infected with 10 pfu per cell of KD3-TERT, GZ3-TERT, KD3, or GZ3. Cells are washed, and cells from one dish of each test condition are collected and frozen. Cells are similarly collected and frozen each day from day 1 to day 8 postinfection. Cells are freeze-thawed three times, and the released virus is titered on 293 E4 cells. Based on previous experiments, the pfu for GZ3 is expected to increase at days 1, 2, and 3 days postinfection. The pfu plateaus at day 3 at $10^8$ pfu per dish. The pfu per dish of GZ3-TERT should increase slowly and gradually by 2 logs at 8 days postinfection. The pfu per dish of KD3 similarly should increase by about one log at day 8. The pfu per dish of KD3-TERT should not increase. These results would indicate that GZ3 grows well in these primary cells, that GZ3-TERT and KD3 grow very poorly, and that KD3-TERT shows little or no growth.

Example 9
Injection of GZ3-TERT and KD3-TERT Vectors in Nude Mice with Tumors.

The inventors envision that GZ3-TERT and KD3-TERT adenovirus vectors will be able to inhibit the growth of human tumors in an animal model, thereby providing a method for promoting death of neoplastic cells in a patient with these novel vectors.

Nude mice are inoculated into each hind flank with $2 \times 10^7$ A549 cells. After 1 week tumors form, ranging in size from about 20 μl to 100 μl. Individual tumors are injected three days later, and at subsequent weeks for 4 weeks (total of 5 injections), with 50 μl of buffer or 50 μl of buffer containing $5 \times 10^8$ pfu of dl309, GZ3-TERT, KD3-TERT, GZ3, KD3, dl01/07, or pm734.1, with a total virus dose per tumor of $3 \times 10^8$ pfu. Higher doses of virus may be used in other experiments; up to a maximum dose of $5 \times 10^8$ pfu per injection. The mutant pm734.1 lacks ADP activity due to two nonsense mutations in the gene for ADP, but all other Ad proteins are expected to be synthesized at wild-type levels (Tollefson et al., *J. Virol.* 70:2296–2306, 1996). The efficacy of each virus (or buffer) is tested on six tumors. At weekly intervals, the length (L) and width (W) of tumors are measured using a Mitutoyo digital caliper. Tumor volumes are calculated by multiplying $(L \times W^2)/2$. This value is divided by the tumor volume at the time of the initial virus injection, the fold-increase in tumor growth is calculated, and the average for the six tumors is graphed.

In co-pending U.S. patent application Ser. No. 09/351,778, the experiments described above were performed using dl309, dl01/07, KD1, KD3, or pm734.1. KD1 and KD3 are adenovirus vectors that comprise ADP, but lack the hTERT promoter. The resulting data showed tumors that received buffer continued to grow, increasing about 14-fold by 5 weeks. In contrast, tumors injected with dl309, which expresses normal amounts of ADP and lacks the E3 RID and 14.7K and proteins, only grew about 2.5-fold by 5 weeks. With pm734.1, which lacks ADP, the tumors grew as well as those that received buffer. Thus, dl309 markedly decreased the rate of tumor growth, and ADP was required for this decrease. Tumors inoculated with dl01/07 grew about 8-fold over 5 weeks. Since dl01/07 is identical to dl309 except for the E1A mutation, this result indicates that the E1 A mutation significantly reduces the ability of Ad to prevent growth of the tumors. This effect is probably due to a reduction in virus replication in the tumors resulting in lower ADP expression, but it could also reflect other properties of E1A in the tumor cells, e.g. the inability of the mutant E1A proteins to induce apoptosis. Most importantly, tumors inoculated with KD1 or KD3 only grew about 2.5-fold. Thus, overexpression of ADP by KD1 and KD3 allows KD1 and KD3 to reduce tumor growth to a rate markedly slower than dl01/07 (their parental control virus), and even to a rate similar to that of dl309. Tumors that received five injections of vectors, but only one dose of vector, in this case $5 \times 10^8$ of each of KD 1 or KD3, are sufficient to significantly reduce the rate of A549 tumor growth.

The inventors have conducted other studies that addressed whether an adenovirus replication-competent ADP-overexpressing vector could suppress the growth of human cancer cells as tumors in nude mice. In those studies, they compared the ability of the vectors KD1-SPB and KD1 to suppress the growth of H441 (lung cancer, human) and Hep3B (liver cancer, human) cells in nude mice (Doronin et al., *J. Virol.* 75:3314–3324, 2001). The vector KD1-SPB is similar to KD3-TERT in that both vectors have the same mutation in the E1A gene, they both overexpress the ADP protein, and they both lack the gene for the gp19K, RIDα, RIDβ, and 14.7K proteins in the E3 region. KD3-TERT, as described, has the E4 promoter deleted and replaced with the TERT promoter. KD1-SPB has the E4 promoter deleted and replaced with the SPB (Surfactant Protein B) promoter. The SPB promoter is active only in type II alveolar cells and Clara cells of the lung. KD1-SPB replicates efficiently only in cells were the SPB promoter is active, e.g. H441 cells, and not in cells where the SPB promoter is not active, e.g. Hep3B cells. As expected from the properties of these vectors, both KD1-SPB and KD1 were effective in suppressing the growth of H441 tumors in nude mice. In the specific experiment reported (Doronin et al, *J. Virol.* 75:3314–3324, 2001), H441 or Hep3B cells were injected into flanks of nude mice and allowed to grow to about 100 μl (H441) or 150 μl or with $5 \times 10^7$ pfu of KD1 or KD1-SPB. Infections of the viruses were repeated twice weekly for 3 weeks to a total dose of $3.0 \times 10^8$ pfu per tumor. Tumors were measured, and the mean fold increase in tumor size was calculated. Mock-infected H441 tumors increased in size by approximately 13-fold over 33 days. Tumors infected with KD1-SPB or KD1 grew only about 4-fold. KD1 similarly suppressed the growth of Hep3B tumors, but KD1-SPB had little or no effect.

The inventors also envision that GZ3-TERT and KD3-TERT can reduce the rate of growth in nude mice of a human colon cancer cell line, SW480. These cells form rapidly growing tumors that are highly vascularized. The hind flank of nude mice are inoculated with $1 \times 10^7$ of SW480 cells. After tumors reach about 100 μl, they are injected twice per week for 3 weeks with 50 μl of buffer or $5 \times 10^7$ pfu of GZ3-TERT, KD3-TERT or dl309. There are typically 8–10 tumors per test virus. The tumor sizes are measured and the fold increase in size at 0 to 3.5 weeks following the initial virus injection is graphed as described above for the A549 tumors. Tumors that receive buffer alone are expected to grow 20-fold over 3 weeks. Tumors that receive GZ3-TERT or KD3-TERT are expected to grow about 4-fold, establishing that GZ3-TERT or KD3-TERT can reduce the growth of SW480 tumors in nude mice.

The results described in the copending U.S. patent application Ser. No. 09/351,778 point to the potency of ADP as an anti-tumor agent when expressed in an Ad vector. It is highly probable that GZ3-TERT or KD3-TERT will provide significant clinical benefits when used to infect tumors growing in humans.

What is claimed is:

1. A recombinant adenovirus vector which overexpresses an adenovirus death protein (ADP) and which is replication-restricted to neoplastic cells expressing telomerase comprising (a) a human telomerase reverse transcriptase (hTERT) promoter, which is operatively linked to an E4 gene, and (b) at least one inactivating mutation in the E3 region.

2. The vector of claim 1 having the sequence as shown in SEQ ID NO:1.

3. The vector of claim 1, further comprising at least one inactivating mutation in the E1A region.

4. The vector of claim 3, wherein at least one inactivating mutation disrupts E1A protein's binding to p300, a member of pRb family, or both.

5. The vector of claim 3 having the sequence as shown in SEQ ID NO:2.

6. A pharmaceutical composition comprising the vector of claim 1 or claim 3 and a pharmaceutically acceptable carrier.

7. An in vitro method for promoting death of a cell expressing telomerase comprising contacting said cell with the vector of claim 1 or claim 3.

8. A kit for promoting death of veils expressing telomerase comprising
  (a) the vector of claim 1 or claim 3;
  (b) a cell line expressing telomerase and having a positive lethal response to the vector selected in (a); and
  (c) a negative control cell line impermissive for replication of the vector selected in (a).

9. A method for promoting death of a neoplastic cell in a mammal, comprising administering an effective amount of the vector of claim 1 or claim 3 to said mammal.

10. The method of claim 9, wherein the vector has the sequence identified by SEQ ID NO:1 or SEQ ID NO:2.

11. The method of claim 9, wherein the neoplastic cell is a human neoplastic cell.

* * * * *